United States Patent
Suwanto et al.

(10) Patent No.: US 11,478,063 B2
(45) Date of Patent: Oct. 25, 2022

(54) CLEANING SYSTEM FOR COSMETIC DISPENSING DEVICE

(71) Applicant: L'OREAL, Paris (FR)

(72) Inventors: Aldina Suwanto, Clichy (FR); Gregoire Charraud, Levallois-Perret (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/139,391

(22) Filed: Dec. 31, 2020

(65) Prior Publication Data

US 2021/0235850 A1 Aug. 5, 2021

Related U.S. Application Data

(60) Provisional application No. 62/968,877, filed on Jan. 31, 2020.

(51) Int. Cl.
  *A45D 44/00* (2006.01)
  *G06Q 30/06* (2012.01)
  (Continued)

(52) U.S. Cl.
  CPC .......... *A45D 44/005* (2013.01); *A45D 34/04* (2013.01); *A45D 34/06* (2013.01); *A61K 8/02* (2013.01);
  (Continued)

(58) Field of Classification Search
  CPC .. A45D 44/005; A45D 44/02; A45D 2200/05; A45D 2200/054; B08B 9/08;
  (Continued)

(56) References Cited

U.S. PATENT DOCUMENTS

| 1,943,647 | A | * | 1/1934 | Weller | .......... A47L 1/15 100/211 |
| 3,263,871 | A | * | 8/1966 | Thompson | .......... B05B 11/3001 222/384 |

(Continued)

FOREIGN PATENT DOCUMENTS

WO  WO 2016/014888 A1  1/2016

OTHER PUBLICATIONS

French Search Report dated Aug. 31, 2022, issued in French Patent Application No. 2100944.

*Primary Examiner* — Patrick M. Buechner
(74) *Attorney, Agent, or Firm* — Oblon, McClelland, Maier & Neustadt, L.L.P.

(57) ABSTRACT

An apparatus is described for dispensing cosmetic material from a cartridge onto a dispensing surface. The apparatus includes a retractable plate disposed beneath the detachable portion, where a dispensing end of the at least one cartridge is configured to penetrate the retractable plate and the detachable portion. When the retractable plate is at a stable highest position, the dispensing end of the at least one cartridge is flush with the surface of the retractable plate. When the retractable plate is moved to a predetermined stable downward position below the highest position, and the detachable portion is placed on the retractable surface, the dispensing end of the at least one cartridge is flush with the dispensing surface and the retractable plate is configured to move even further downward to an unstable position in response to a downward force on the detachable portion.

4 Claims, 49 Drawing Sheets

(51) Int. Cl.
*G06T 11/00* (2006.01)
*A45D 34/04* (2006.01)
*A61Q 1/02* (2006.01)
*A61Q 1/12* (2006.01)
*A61Q 17/00* (2006.01)
*B08B 3/08* (2006.01)
*H04W 4/80* (2018.01)
*A45D 34/06* (2006.01)
*H04W 64/00* (2009.01)
*G06T 7/90* (2017.01)
*A61K 8/02* (2006.01)
*G06V 20/40* (2022.01)
*G06V 40/16* (2022.01)
*G06Q 50/00* (2012.01)
*A45D 34/00* (2006.01)
*G06F 16/9035* (2019.01)

(52) U.S. Cl.
CPC ............ *A61Q 1/02* (2013.01); *A61Q 1/12* (2013.01); *A61Q 17/005* (2013.01); *B08B 3/08* (2013.01); *G06Q 30/0631* (2013.01); *G06T 7/90* (2017.01); *G06T 11/001* (2013.01); *G06V 20/40* (2022.01); *G06V 40/161* (2022.01); *G06V 40/169* (2022.01); *H04W 4/80* (2018.02); *H04W 64/006* (2013.01); *A45D 2034/002* (2013.01); *A45D 2034/005* (2013.01); *A45D 2200/058* (2013.01); *A45D 2200/205* (2013.01); *A61K 2800/59* (2013.01); *G06F 16/9035* (2019.01); *G06Q 30/0643* (2013.01); *G06Q 50/01* (2013.01); *G06T 2207/10016* (2013.01); *G06T 2207/30196* (2013.01)

(58) Field of Classification Search
CPC .... B08B 9/20; B08B 9/28; B08B 9/34; B08B 9/0821; B08B 9/0813; B08B 2209/08; B05B 11/0054; B05B 11/0078
USPC .............................. 222/405; 401/123, 188 R
See application file for complete search history.

(56) References Cited

U.S. PATENT DOCUMENTS

| | | | | |
|---|---|---|---|---|
| 4,844,299 | A * | 7/1989 | Sekiguchi | B05B 11/3069 222/94 |
| 4,946,076 | A * | 8/1990 | Hackmann | B05B 11/3074 222/405 |
| 6,682,246 | B2 * | 1/2004 | Reggiani | B65D 83/285 401/206 |
| 7,004,659 | B1 * | 2/2006 | Goodman | B05C 17/002 401/265 |
| 8,814,002 | B2 * | 8/2014 | Pires | G01F 11/021 222/278 |
| 2001/0031168 | A1 * | 10/2001 | Gueret | A45D 34/04 401/126 |
| 2008/0169312 | A1 * | 7/2008 | Kee | B05B 11/00416 222/405 |
| 2009/0035052 | A1 * | 2/2009 | Goodman | B05C 17/002 401/266 |
| 2017/0208920 | A1 | 7/2017 | Thiebaut et al. | |

* cited by examiner

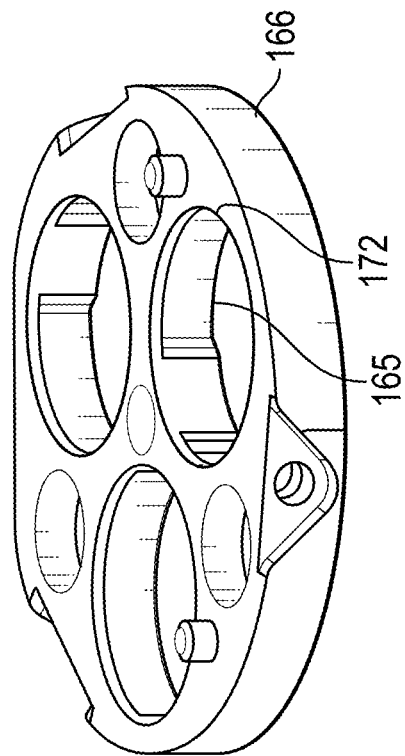
FIG. 7A
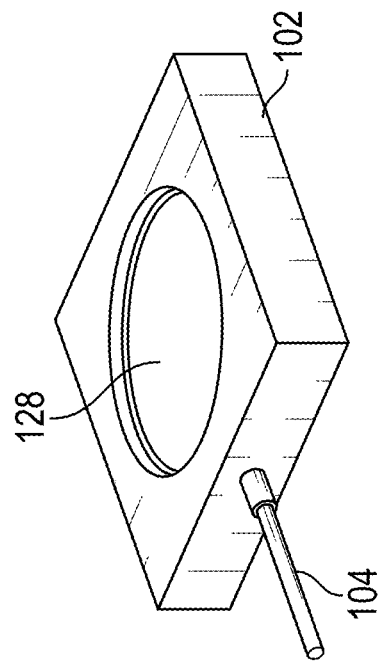
FIG. 8
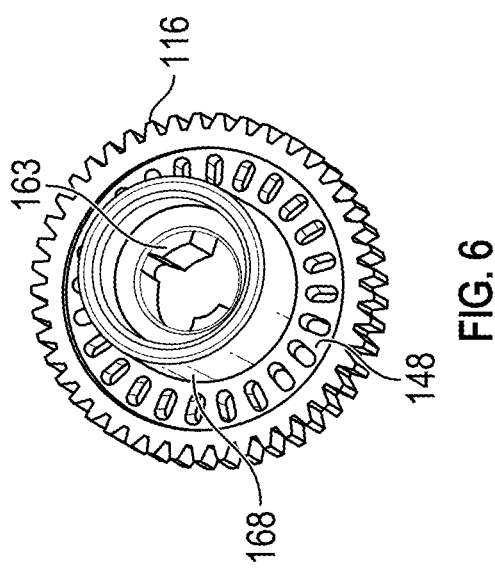
FIG. 6
FIG. 7B

USAGE SETUP
1. The User Selects the Mode for Lipstick Selection:
   - Social Media Trend Recommendation by the AI Algorithms
   - Create my Own Lipstick
   - Match my Look Based on Selfie Picture
2. Shade and Finish Selection on Proposed Picture is Extracted
3. Virtually try on in Real Time, the User can Adjust the Color Presented
4. Click on the Button to Dispense the Formula → an Internal Neural Network will Decompose the Color Requested into Different Color Cartridge Dose.
5. The User can then Apply and Provide a Feedback if he Liked or not the Rendering
6. The User can also Save his Favorite Look and Color to Reuse Later on
7. The User can also Share the Look and Color on the Web.

1720

DISPENSER
- The Device Receives a Command to Dispense a Certain Proportion of each Cartridge
- The Device Dispenses on the Top Part and User can Mix it to Obtain the Desired Color
- The Device Send Back Inventory Left of Formula to the Consumer App to Make Sure Only Dispensable Color are Available in the UI.

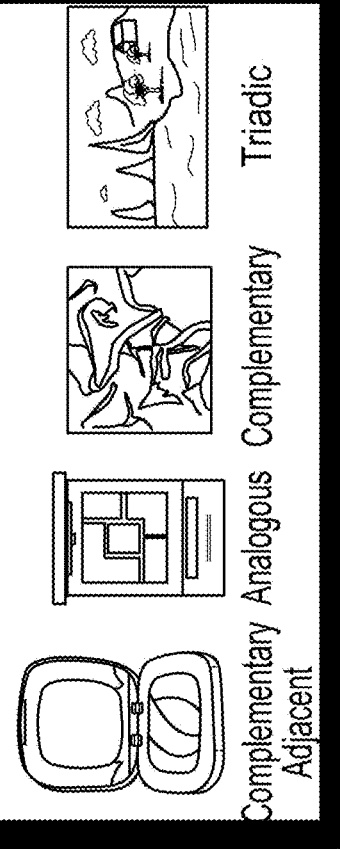
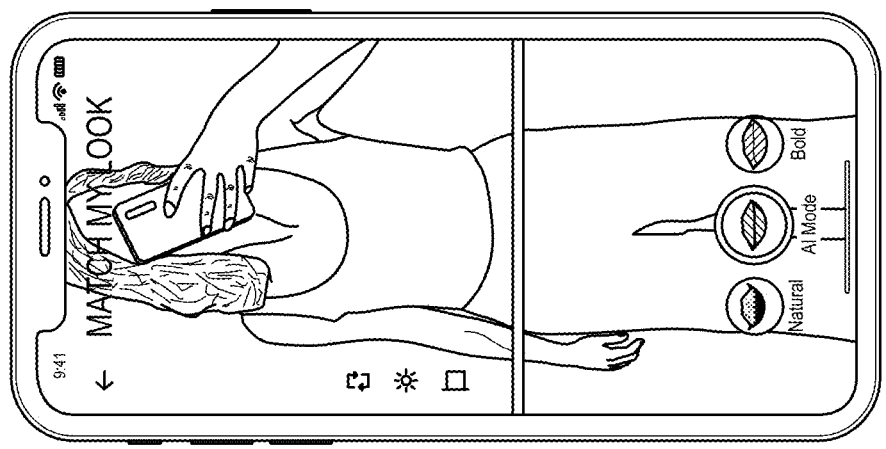
FIG. 18D

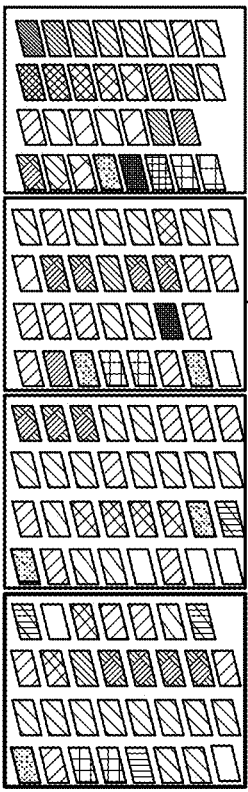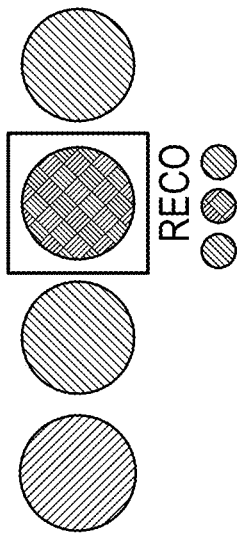
FIG. 18D (Continued)

USAGE SETUP

1. The app collects environmental data based on geolocation and combine it with a smartphone diagnosis assessing clinical signs (wrinkles, dark spots, firmness, pores, fine lines, dullness).
2. The user can also collect data of UV sensor that will actually give precise measurement of the cumulated UV exposure received.
3. Based on historical data of skin assessment and environmental factor, the app will process the ideal formulation to fight against your skin aging signs and prevent from environment.
4. The app send the command to the dispenser
5. The user can feedback his favorite recipes for a specific period of time.

1920

DISPENSER

- The Device Receives a Command to Dispense a Certain Proportion of each Cartridge
- The Device Dispenses on the Top Part and User can Mix it to Obtain the Desired Color
- The Device Send Back Inventory Left of Formula to the Consumer App to Make Sure Only Dispensable Actives are Available in the UI.

USAGE SETUP

1. The app collects environmental data based on geolocation and combine it with a smartphone diagnosis assessing the skin tone of the user.
2. Depending of the condition, the app decides to merge skincare actives with the foundation like SPF when the environmental conditions are not optimal.
3. The app based on the period of the year and the tanning level of the person slightly adjust the foundation color to follow the skintone evolution.
4. When the color is not perfecting matching, the user can send a feedback to the cloud to improve remotely the algorithms.
5. In certain cases, the user may want to use the device to adjust primer color so as to achieve specific make up strategy by layering different colors.

2120

DISPENSER

- The Device Receives a Command to Dispense a Certain Proportion of each Cartridge
- The Device Dispenses on the Top Part and User can Mix it to Obtain the Desired Color
- The Device Send Back Inventory Left of Formula to the Consumer App to Make Sure Only Dispensable Actives are Available in the UI.

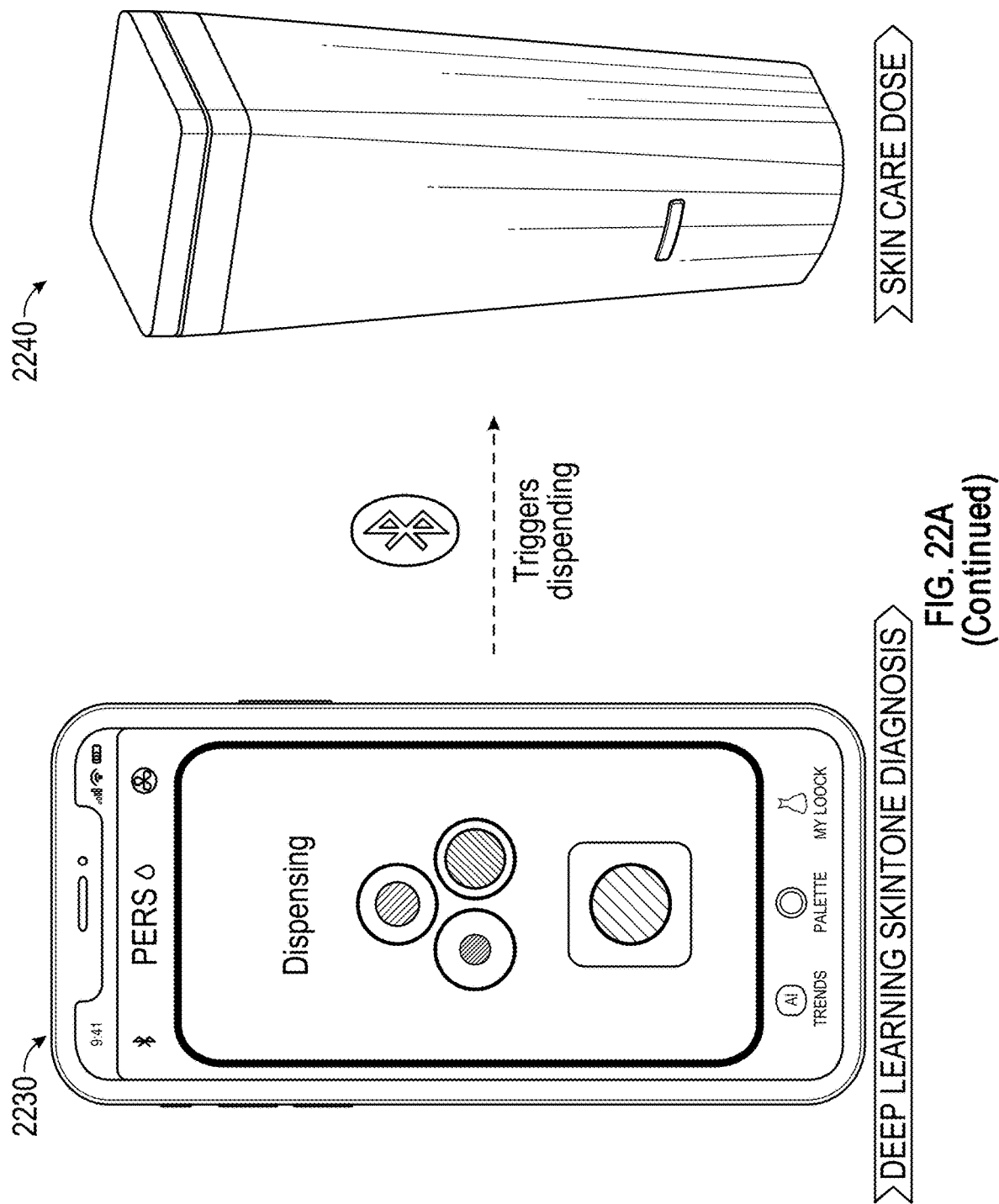

| Off | Page | | | | |
|---|---|---|---|---|---|
| | | Tag ID | | | |
| 0h | 0 | type | sp. | | |
| 4h | 1 | formula _id | | | production information |
| 8h | 2 | | | | |
| Ch | 3 | vol_u | dur _use | | |
| 10h | 4 | batch_id | | | |
| 14h | 5 | | | | |
| 18h | 6 | prodd | expd | | |
| 1Ch | 7 | signature | | | |
| 20h | 8 | sp. | lid | t# | |
| 24h | 9 | device_id | | | usage tracking |
| 28h | A | opened | ened | | |
| 2Ch | B | latest_use | | | |
| 30h | C | error | sp. | | |
| 34h | D | vol_c | urcrc16 | | |
| Size | | 56bytes | | | |

FIG. 24

| Field | Base Type | Length | Page | Responsability | Description |
|---|---|---|---|---|---|
| tagid | u8 | 8 | 0 | tag manufacturer | Unique id of the tag (iso 15693) |
| type | u8 | 1 | 0 | production line | 00h tag for Perso V1 |
| sp. | u8 | 3 | 0 | production line | Spare (default value '000000h) |
| formula_id | alpha_id | 8 | 1 | production line | ID of formula contained in cartridge |
| vol_u | U1e16 | 2 | 3 | production line | Full capacity of the cartridge |
| dur_use | U1e16 | 2 | 3 | production line | How many days cartridge can be used once opened |
| batch_id | alpha_id | 8 | 5 | production line | Id of production batch (factory) |
| prodd | day_t | 2 | 6 | production line | Date of production (factory) |
| expd | day_t | 2 | 6 | production line | Expiration date |
| signature | u1e32 | 4 | 7 | production line | Signature |
| sp. | u8 | 2 | 8 | application | Spare (default value '00h) |
| lid | u8 | 1 | 8 | application | Counter for lid opening |
| tt# | u8 | 1 | 8 | application | Tube id where the cartridge is inserted |
| device_id | u8 | 4 | 9 | application | Device id when the cartridge was inserted |
| opend | day_t | 2 | A | application | Date of first priming |
| endd | day_t | 2 | A | application | Date the cartridge will be not usable |
| latest_use | time_t | 4 | B | application | Timestamp of latest usage |
| error | le16 | 2 | C | application | Error made during dispensing |
| sp. | U1e16 | 2 | C | application | Spare (default value '00h) |
| vol_c | U1e16 | 2 | D | application | Current volume in the cartridge |
| ncrc16 | le16 | 2 | D | application | Crc16 of usage cartridge |

Contact/effect hall sensor that detects and count the lid opening/closing cycle to trigger consumable reading and change detection

2620

Specific NFC antenna for each canal that read and write information onto the consumable integrated circuit at each dispensing

FIG. 26

US 11,478,063 B2

CLEANING SYSTEM FOR COSMETIC DISPENSING DEVICE

CROSS-REFERENCE TO RELATED APPLICATIONS

This application claims the benefit of U.S. Provisional Application No. 62/968,877 filed Jan. 31, 2020, the entire contents of which are incorporated herein by reference.

BACKGROUND

Field

The disclosure herein generally relates to a system, apparatus, and method for determining a combination of cosmetic materials which can be blended and dispensed for a particular user.

SUMMARY

In an embodiment, an apparatus is provide for dispensing cosmetic material, including a dispensing device configured to receive at least one cartridge that contains a cosmetic material and to dispense a specified amount of the cosmetic material from the cartridge onto a dispensing surface; wherein the dispensing surface is configured to be part of a detachable portion of the apparatus, and the dispensing device further includes a retractable plate disposed beneath the detachable portion, wherein a dispensing end of the at least one cartridge is configured to penetrate the retractable plate and the detachable portion, such that (i) when the retractable plate is at a stable highest position, the dispensing end of the at least one cartridge is flush with the surface of the retractable plate, (ii) when the retractable plate is moved to a predetermined stable downward position below the highest position, and the detachable portion is placed on the retractable surface, the dispensing end of the at least one cartridge is flush with the dispensing surface and the retractable plate is configured to move even further downward to an unstable position in response to a downward force on the detachable portion.

In an embodiment, the apparatus further includes a cleaning formula reservoir disposed between a body of the dispensing device and the retractable plate, and the cleaning formula reservoir has a dispensing end that is configured to penetrate the retractable plate and the detachable portion and is configured to dispense a cleaning formula onto the dispensing surface when the retractable plate is configured to move even further downward to the unstable position.

In an embodiment, the apparatus further includes a spring mechanism that is coupled to a bottom surface of the retractable plate at one end and a body of the dispensing device at another end.

In an embodiment, at least one cartridge is configured to dispense a remaining amount of the cosmetic material from the cartridge into the dispensing surface onto the dispensing surface when the retractable plate is configured to move even further downward to the unstable position

BRIEF DESCRIPTION OF THE DRAWINGS

The patent or application file contains at least one drawing executed in color. A more complete appreciation of the disclosure and many of the attendant advantages thereof will be readily obtained as the same becomes better understood by reference to the following detailed description when considered in connection with the accompanying drawings wherein:

FIG. 6 is a perspective view of a cartridge gear, according to one example;

FIG. 7A is a perspective view of a bottom plate, according to one example;

FIG. 7B is a perspective view of the bottom plate, viewed from the bottom, according to one example;

FIG. 8 is a perspective view of a base, according to one example;

FIG. 18D shows how a "match my look" mode may operate on the app in the lipstick ecosystem.

FIG. 20B shows an example of how a combination of different environmental factors determined to be present for a user can lead to different dosage amounts from three different cartridges.

FIG. 24 shows a data format of the data stored on the NFC tag on the cartridge.

FIG. 25 shows a table that includes descriptions of the various fields contained in the data format of the NFC tag.

FIG. 26 shows a structure of the dispensing device that is equipped for a smart swappable cartridge system.

DETAILED DESCRIPTION OF THE EMBODIMENTS

Figure 1:
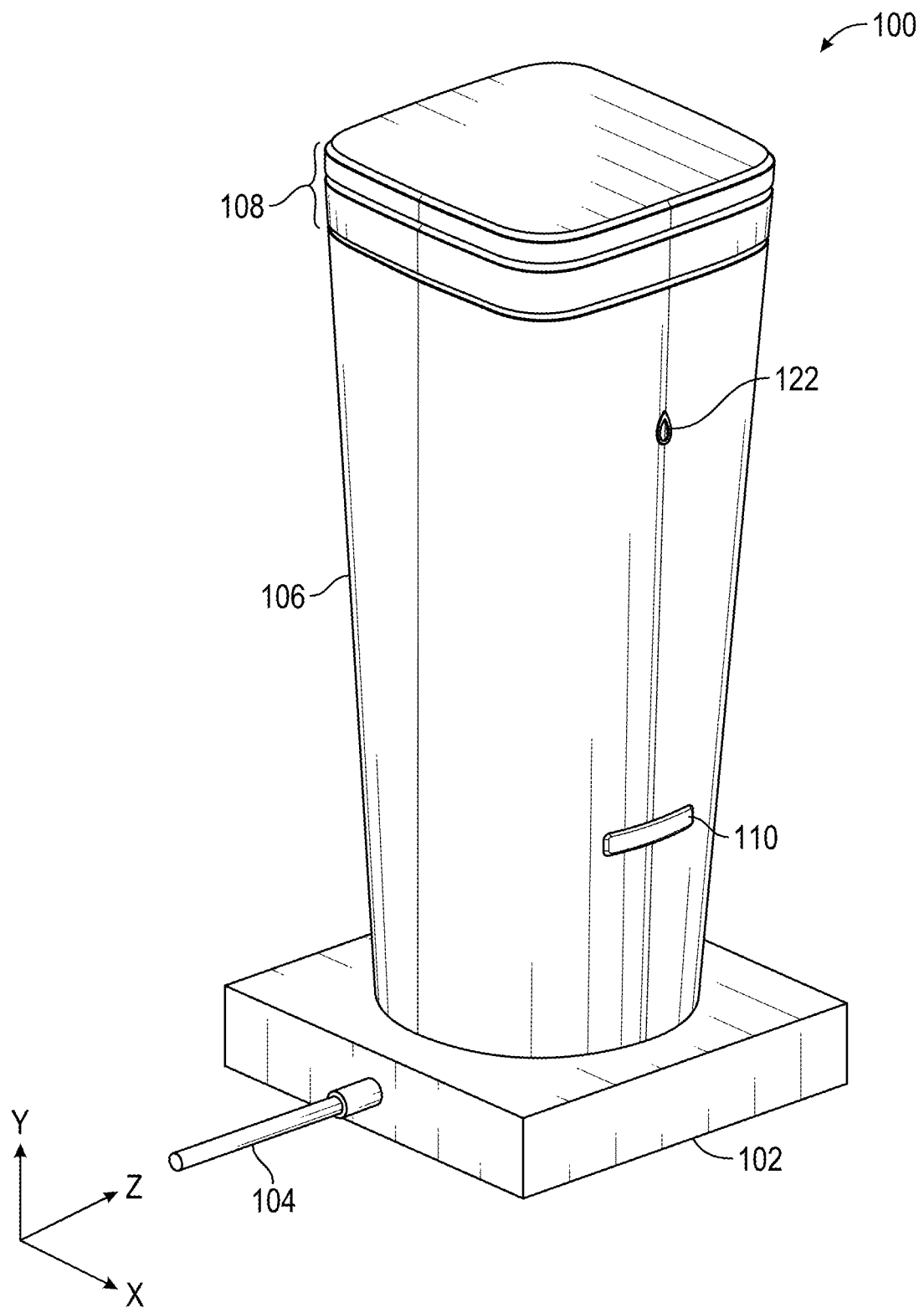
FIG. 1 is an overall perspective view of a cosmetic dispensing device, or a cosmetic dispenser, according to one example.

In the drawings, like reference numerals designate identical or corresponding parts throughout the several views. Further, as used herein, the words "a", "an" and the like generally carry a meaning of "one or more", unless stated otherwise.

Referring now to the drawings, wherein like reference numerals designate identical or corresponding parts throughout the several views.

Selecting cosmetic formulations, and component cosmetic materials to formulate cosmetic formulations, is a common activity often relying on subjective decision making and manual input. There are a wide variety of available cosmetic materials, and countless combinations and permutations of possible cosmetic formulations.

For each occasion where cosmetic formulations are used, subjective decisions are often made by an end user of cosmetics to produce satisfactory cosmetic formulations. Outcomes are generally the result of experimentation, perhaps requiring multiple iterations to produce a satisfactory outcome. Partly due to limited awareness of specific traits of the base cosmetic materials and necessary proportions, resulting cosmetic formulations may lack precision. The repeatability of producing a specific cosmetic formulation is thus difficult to accomplish. The below embodiments address these problems in the conventional art.

Specifically, the below description relates to an ecosystem for enabling skincare and make a formula personalization system for use at home which is based on a specialized dispensing device that allows ingredients for a cosmetic product to be instantly blended into a user's preferred end result and then conveniently transported for portability.

The system shown in the below is a first-of-its-kind, AI-powered 3-in-1 device for personalized at-home skincare, foundation, and liquid lipstick. The device and its corresponding app assess users' individual skin and local environmental data to create and deliver personalized, on-the-spot skincare and cosmetic formulas that optimize for increasing levels of personalization over time.

The overall eco-system features an AI-enabled, motorized cartridge system as described above that creates personalized skincare and cosmetics formulas in four steps. The device creates personalized skin serums through the following process:

1. Personal skin analysis: The user takes a photo with a smartphone camera and opens an app on the smartphone. The app uses AI to analyze the user's overall skin condition, assessing deep wrinkles, fine lines, dark spots, lack of firmness, pore visibility, and lack of radiance.

2. Environmental assessment: The app (and/or a separate cloud computing platform) assesses local environmental conditions that can influence the state of the user's skin, including weather, temperature, humidity, UV index, air quality, and pollen.

3. Product preference: The user then enters specific skincare concerns, like fine lines, wrinkles, dark spots, rough skin texture and dullness into the app.

4. Custom formulation and dispensing: A personalized blend of high-performance skincare is then dispensed in a portioned, single dose at the top of the device.

The motor system, located at the top of the device, moves and compresses the formula from the cartridges at the base of the machine in an upward motion to the dispensing tray above for a clean application.

With regular use, the AI platform can assess the appearance of a user's skin over time, helping users identify what is working, and calibrating future formulas. The AI-powered system can optimize the efficacy of personalized formulas. By taking photos regularly, users enable the smart system to recognize the formulas' effects, and adjust the dosage of active ingredients accordingly. That said, the user can override the system recommendations if they are seeking, for example, additional moisturizer.

The skincare system contains active ingredients including AHAs, Vitamins C and E, hyaluronic acid, ferulic acid, retinol, cucumber, thyme, and mulberry.

The cosmetics offerings—for foundation and liquid lipstick—will have the capability to incorporate real-time trend information as well as color-matching technology into its personalized product offerings as described below.

Using the lipstick system, consumers will be able to create liquid lipstick based on their personal skintone and preferences. The system can shade-match a user's clothing or accessories, or they can even opt to create a particular color that is trending on social media. The device will have three cartridges; collectively, these cartridges will have the capability to create hundreds of shades.

The foundation system described below will contain three cartridges, ranging from light to deep tones. Knowing that foundation is never one-size-fits-all, a selection of these color trios may be offered in order to match the widest variety of shades. Using a shade-matching tool, the three cartridges will dispense varying levels of color to create personalized shades. The device has the capability to create hundreds of custom shades. The device will create a single dose of color, but users can easily double or triple the amount with an additional touch.

There are three dosing settings for the system described herein. There will be a standard-sized dose (0.7 grams; roughly the size of a pistachio) that users can double or triple with an additional touch.

The device features a detachable mirrored compact so you can take a portioned dose of product with you.

From opening the app and taking a photo of one's face to dispensing product, the user experience with the present system takes about three minutes.

[Dispensing Device]

FIG. 1 is an overall perspective view of a cosmetic dispensing device 100, or a cosmetic dispenser, according to one example. The visible portion of the cosmetic dispenser 100 includes a base 102 connected to a power cord 104. The base 102 provides a support for the dispenser body 106. A compact 108 is disposed above the dispenser body 106, a power button 110 may be disposed partly within the dispenser body 106 such that the dispenser body 106 secures placement of the power button 110, and an indicator light and button 122 may be disposed partly within the dispenser body 106 such that the dispenser body 106 secures placement of the indicator light and button 122. The indicator light and button 122 may be a mechanical or capacitive touch-type button.

Figure 2:
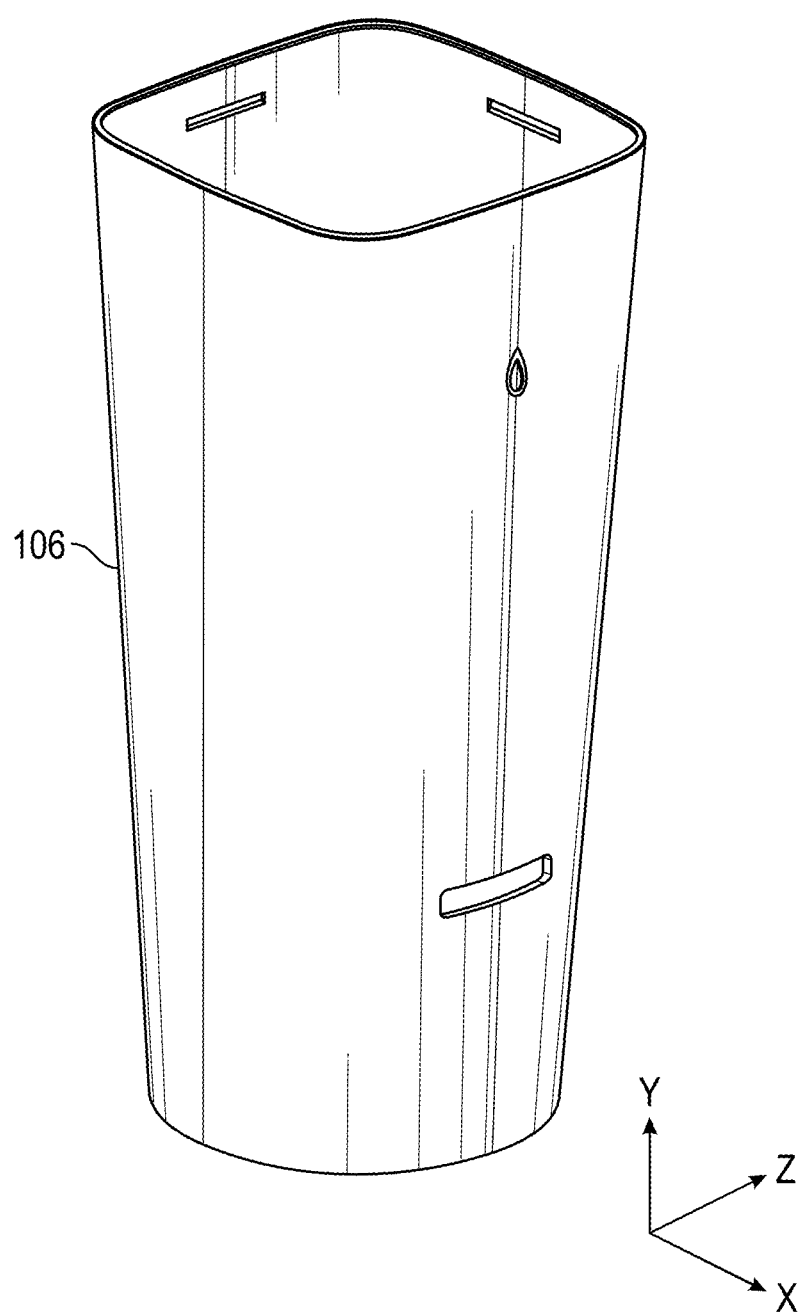
FIG. 2 is a perspective view of a dispenser body, according to one example.

FIG. 2 is a perspective view of the dispenser body 106, according to one example. The dispenser body 106 is a hollow, thin-walled container that serves as a cover for much of the components of the cosmetic dispenser 100. In this example the dispenser body 106 has a first end at the top with an approximately square cross section with rounded corners, while a second end at the bottom has a circular cross section. The dispenser body 106 may provide a base for the compact 108, or other components that serve as a base for the compact 108. The dispenser body 106 may also include a mounting point for the power button 110 and a mounting point for the indicator light and button 122.

Figure 3:
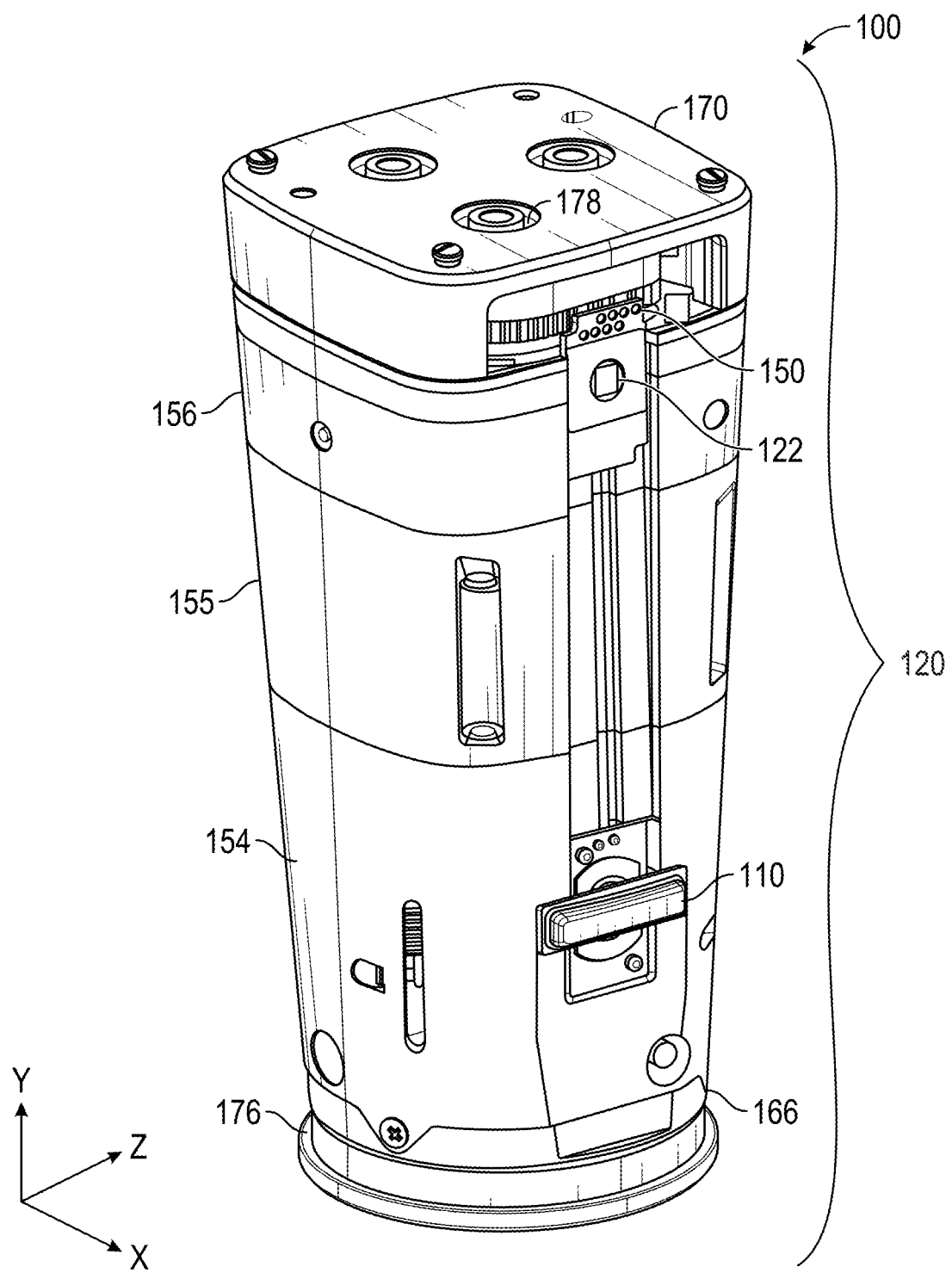
FIG. 3 is a perspective view of the cosmetic dispenser with the dispenser body removed, according to one example.

FIG. 3 is a perspective view of the cosmetic dispenser 100 with the dispenser body 106 removed, according to one example. The power button 110, the indicator light and button 122, a controller 150, a bottom plate 166, an inductive plate 176, and a gearhousing 170 are visible in this view, as are a lower body section 154, a middle body section 155, and an upper body section 156. The power button 110 is electrically connected to the controller 150.

The controller 150 includes circuitry for distributing power received through the power cord 104, controlling one or more motors 112 to dispense cosmetic material, detecting readings of an optical encoder 192, charging one or more batteries 126, operating any indicators such as the indicator light and button 122, chimes, or other audiovisual signals, sensors such as for detecting availability status, type, and quantity of cosmetic material, and communicating wirelessly with external devices, including circuitry to send and receive signals and data, for example through smart phones and other wireless devices, using a variety of communication protocols, such as Radio Frequency (RF), Bluetooth, Wi-Fi, or cellular.

The inductive plate 176 supports the bottom plate 166, aside from the base 102 and the power cord 104, the remainder of the cosmetic dispenser 100 is disposed atop the bottom plate 166. The gearhousing 170 is disposed above, is connected to, and provides support to internal components of the cosmetic dispenser 100 that are further described by FIG. 4 through FIG. 9B. Further, the gearhousing 170 includes a plurality of gearhousing cartridge holes 178, one for each cartridge 114 in the cosmetic dispenser 100. A nozzle 160 of each cartridge 114 is disposed inside one of the gearhousing cartridge holes 178. Various additional substructures and covers may be disposed between the internal components of the cosmetic dispenser 100 and the dispenser body 106.

For example, the upper body section 156 is disposed above the middle body section 155, and the lower body section 154 disposed below the middle body section 155. When connected, the dispenser body 106 attaches to outside of at least one of the lower body section 154, the middle body section 155, and the upper body section 156. The bottom plate 166 is disposed below and connected to the lower body section 154.

Figure 4A:
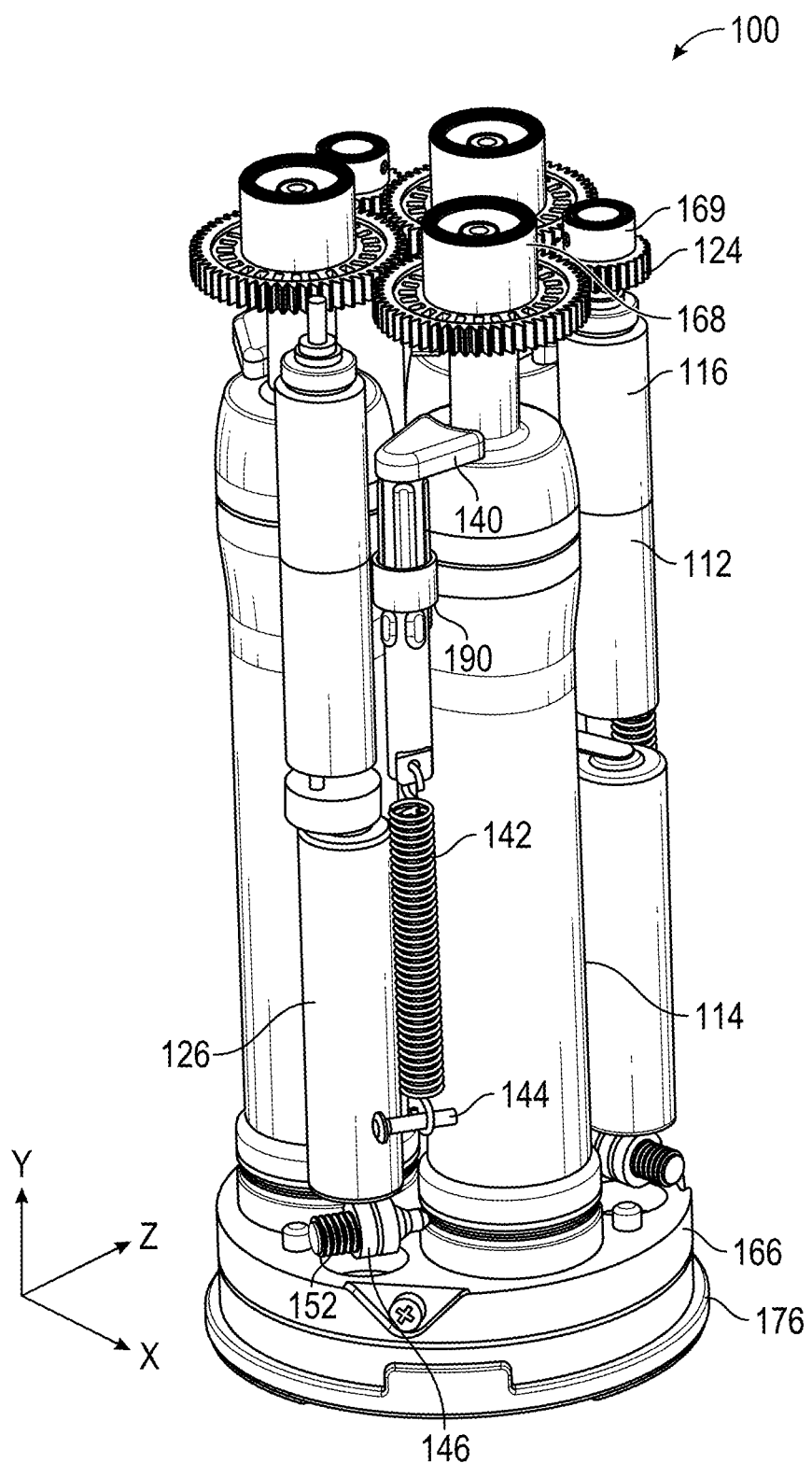
FIG. 4A is a perspective view of internal components of the cosmetic dispenser, according to one example.
Figure 4B:
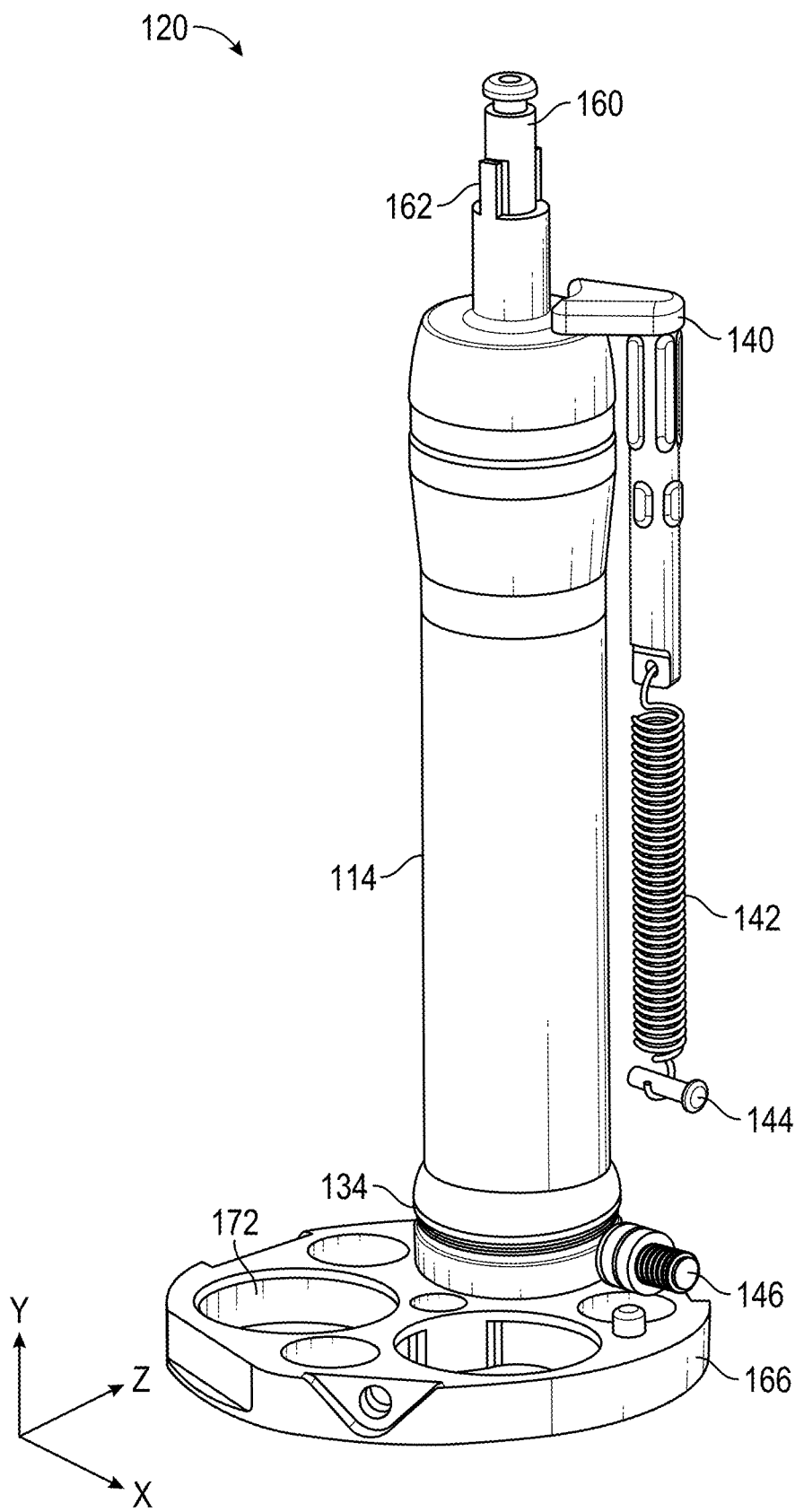
FIG. 4B is a perspective view of internal components of the cosmetic dispenser, according to one example.

FIG. 4A and FIG. 4B are perspective views of internal components of the cosmetic dispenser 100, according to one example. The internal assembly includes a plurality of dispensing assemblies 120, disposed above the bottom plate 166 and the inductive plate 176. Each dispensing assembly 120 comprises a cartridge 114, a cartridge gear 116, a motor 112, a motor gear 124, an ejector 140, an ejector index ring 190, an ejector spring 142, an ejector spring pin 144, a detent plunger 146, and a detent spring 152. The controller 150 controls the operation of each of the dispensing assemblies 120. The cosmetic dispenser 100 includes at least one dispensing assembly 120. The examples described herein contain three dispensing assemblies 120, though a person having ordinary skill in the art will recognize that a cosmetic dispenser 100 may have any number of dispensing assemblies 120.

Further, a plurality of batteries 126 inside the cosmetic dispenser 100 are electrically connected to the plurality of dispensing assemblies 120 to provide electrical power for the operation of the controller 150, the dispensing assembly 120, the motor 112, and various indicators, such as the indicator light and button 122 (further described in FIG. 3), chimes, and other audiovisual signals.

The controller 150 and a connected device 300 (shown in FIG. 14) allow a user to operate the cosmetic dispenser 100 wirelessly. Cosmetic material formulation and recipe commands to the controller 150 may be received from the connected device 300, such as a smart phone, tablet, or personal computer, configured to communicate with the cosmetic dispenser 100. Further, dispensing of cosmetic material may also be triggered by the user by touching the indicator light and button 122 on the cosmetic dispenser 100.

The cartridge 114 also has a cartridge key 162 disposed on or near the nozzle 160, is connected near a first end to the cartridge gear 116, is connected near a second end to the bottom plate 166, with a motor gear 124 connected to the motor 112, and the motor gear 124 drivingly connected to the cartridge gear 116. The cartridge 114 and the cartridge gear 116 are held in position by the gearhousing 170 (shown in FIG. 3). The cartridge 114 may be disposed inside the cosmetic dispenser 100, and secured in place by the ejector 140 connected to an ejector spring 142, the ejector spring pin 144 connected at a first end to the ejector spring 142 and rigidly connected at a second end to an inside surface of at least one of the dispenser body 106, the lower body section 154, the middle body section 155, the upper body section 156, and other internal structure. The dispensing assembly 120 further includes an ejector index ring 190 (shown in FIG. 4A) to guide the movement of the ejector 140 within the cosmetic dispenser 100 during insertion and removal of the cartridge 114, with the ejector index ring 190 disposed against the inside surface of at least one of the dispenser body 106, the lower body section 154, the middle body section 155, and the upper body section 156 to provide a guide for the movement the ejector 140.

Additionally, a detent plunger 146 may be disposed substantially perpendicularly to a longitudinal axis of the cartridge 114 and connected near the second end of the cartridge 114, providing a lateral pressure to a circumferential groove circumferential groove 134 of the cartridge 114, keeping the cartridge 114 in place along the vertical Y-axis, counteracting an opposite force applied by tension to the cartridge 114 by the ejector 140, the ejector spring 142, and an ejector spring pin 144. The ejector 140 is disposed within the cosmetic dispenser 100 and may move substantially parallel to the cartridge 114, and is connected to the ejector spring 142 that is further connected to the ejector spring pin 144. As the cartridge 114 is inserted into the cosmetic dispenser 100, an edge of the ejector 140 contacts an edge near the first end of the cartridge 114. The ejector 140 applies a pressure to the cartridge 114 as the ejector spring 142 stretches with the increasing distance between the stationary ejector spring pin 144 and the ejector 140, as the ejector 140 moves with the cartridge 114 further into the cosmetic dispenser 100. Once the cartridge 114 is inserted to the point that a first end of the detent plunger 146 makes contact with the circumferential groove 134 of the cartridge 114, the motion of the cartridge 114 along the Y-axis is restricted, holding the cartridge 114 in place.

The detent plunger 146 is a mechanism for holding the cartridge 114 in place. The detent plunger 146 moves along an axis substantially perpendicular to that of the major axis of the cartridge 114. A first end of the detent plunger 146 is disposed to make contact with the cartridge 114. A second end is connected to a first end of a detent spring 152, the second end of the detent spring 152 in contact with an inside surface of at least one of the dispenser body 106, the lower body section 154, the middle body section 155, the upper body section 156, or other internal structure. Insertion of the cartridge 114 into the cosmetic dispenser 100 displaces the detent plunger 146 against the detent spring 152, compressing the detent spring 152. Because the contour of the cartridge 114 varies over the length of the cartridge 114, the detent plunger 146, and the detent spring 152 are displaced by varying amounts depending on the position of the cartridge 114 relative to the cosmetic dispenser 100. At a point where the detent plunger 146 contacts the circumferential groove 134 of the cartridge 114, the first end of the detent plunger 146 is able to lock the cartridge 114 in place due to pressure of the detent spring 152 and the geometric relationship between the detent plunger 146 and the circumferential groove 134.

Further, the cartridge 114 is inserted into the cosmetic dispenser 100 through a cartridge through hole 172 of the bottom plate 166. The cartridge through hole 172 has a base key cutout 165 (FIG. 7A) shaped to correspond to the base key 164 such that as the base key 164 and the base key cutout 165 make contact, the cartridge 114 cannot rotate relative to the bottom plate 166. The cartridge 114 is also shaped to fit into the bottom plate 166 and the cartridge gear 116 in a specific orientation. In the position where the cartridge 114 is fully inserted into the cosmetic dispenser 100 and locked in place by the detent plunger 146, the cartridge 114 is seated against the cartridge gear 116. Additionally, the cartridge gear 116 has a collar 168 portion that is rotatably connected to the gearhousing 170, restricting movement of the cartridge gear 116 such that the cartridge gear 116 can rotate about a longitudinal axis but may not move axially or otherwise, and supporting the position of each of the cartridge gears 116 and motor gears 124. Similarly, the motor gear 124 has a motor gear collar 169 portion that is rotatably connected to the gearhousing 170, restricting movement of the motor gear 124 such that the motor gear 124 can rotate about a longitudinal axis but may not move axially or otherwise, preserving the relationship between the cartridge gear 116 and the motor gear 124 such that rotary motion of the motor gear 124 results in rotary motion of the cartridge gear 116 at a fixed ratio.

The motor gear 124 may be a spur gear that includes a key cutout 163 (FIG. 6) that fits the cartridge key 162 of the cartridge 114, as described by FIG. 4B.

Figure 5:
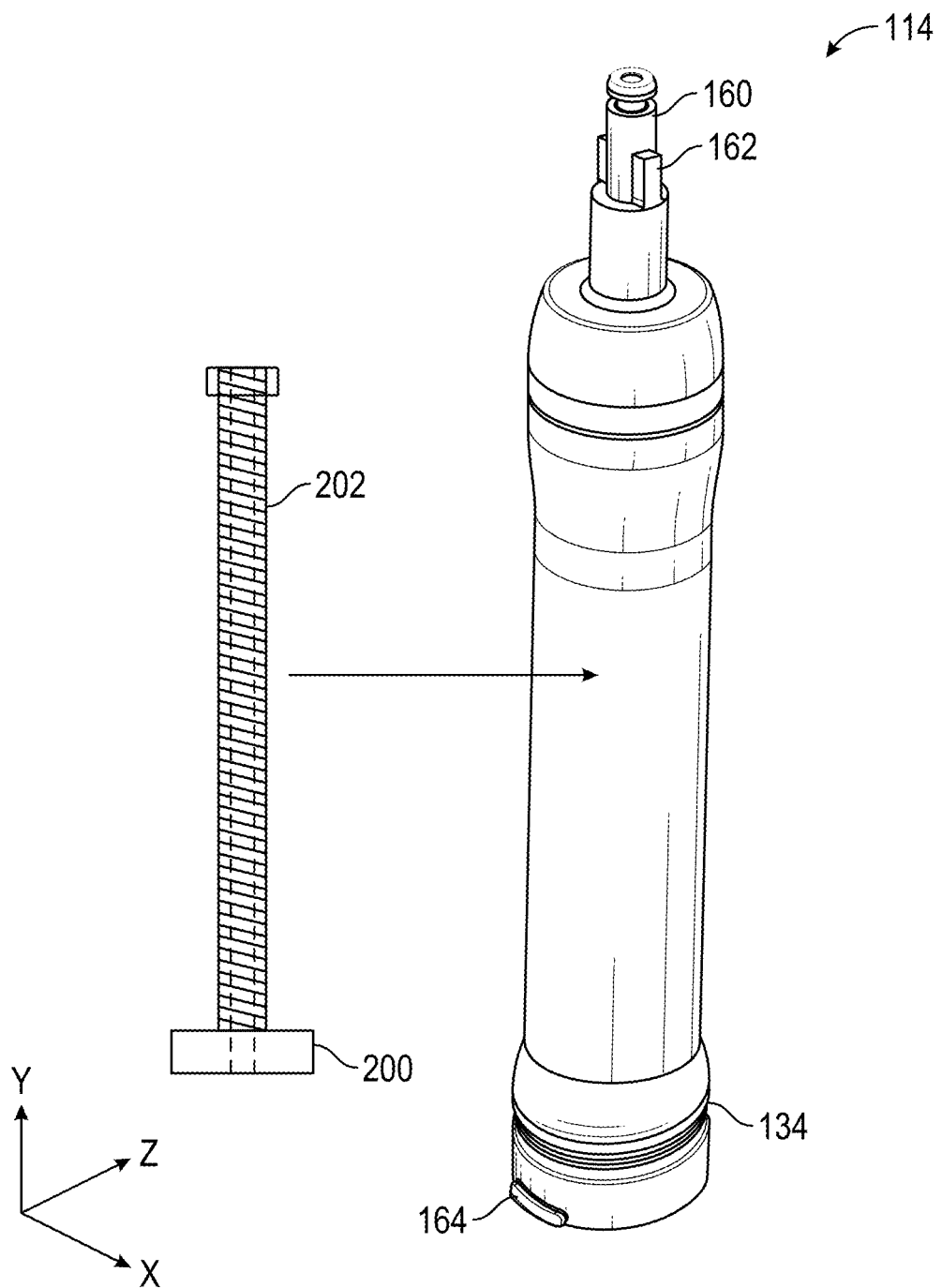
FIG. 5 is a perspective view of a cartridge, according to one example.

FIG. 5 is a perspective view of the cartridge 114, according to one example. The cartridge 114 has a round, cylindrical body and a nozzle 160 at a first end. The nozzle 160 is further disposed near a cartridge key 162. The cartridge key 162 fits inside the opening of the cartridge gear 116, corresponds to the shape of the key cutout 163 of the cartridge gear 116, and locks the rotational motion of the portion near a first end of the cartridge 114 with that of the cartridge gear 116. As the cartridge gear 116 is driven by the motor gear 124 and the motor 112. A second end of the cartridge 114 includes a base key 164. The base key 164 fits inside the base key cutout 165 of the bottom plate 166, secures the second end of the cartridge 114 to the bottom plate 166, and prevents rotational motion of the second end of the cartridge 114 relative to the bottom plate 166. Since the first end of the cartridge 114 is secured to the motion of the cartridge gear 116, actuation of the motor 112 rotates the motor gear 124 and drives the cartridge gear 116, thereby opening and closing the nozzle 160 of the cartridge 114. The first and second ends of the cartridge 114 may rotate relative to one another.

The cartridge 114 contains and dispenses an amount of cosmetic material into the compact 108 as needed (further described by FIG. 9). The cartridge 114 dispenses cosmetic material by rotation of the cartridge gear 116 while the cartridge 114 remains in place substantially vertically along the Y-axis. The cartridge gear 116 is driven by the motor gear 124 that is turned by the rotation of the motor 112. The magnitude of rotation of the motor 112 is controlled by the controller 150.

An amount of cosmetic material is released from the cartridge 114 through the nozzle 160 by a first rotational motion of the first end with respect to the second end of the cartridge 114. Rotational motion of the first end of the cartridge 114 in a second direction, opposite of the first rotational motion, may close the nozzle 160 of the cartridge 114.

The cartridge gear 116 actuates the nozzle 160 of the cartridge 114 that is attached to a hollow cartridge lead screw 202 within the cartridge 114. Rotation of the cartridge lead screw 202 proportionately displaces a cartridge piston 200 that forces an amount of cosmetic material through the cartridge lead screw 202 and out the nozzle 160 of the cartridge 114. The amount of cosmetic material released during an opening and closing operation of the nozzle 160 is a function of the displacement of the cartridge lead screw 202, which is dependent upon the rotational displacement of the cartridge gear 116. Rotation of the motor 112 rotates the respective motor gear 124 and the cartridge gear 116. The controller 150 detects the relative motion of the cartridge gear 116 using the optical encoder 192 to count a number of cartridge gear slots 148 that pass the optical encoder 192 as the cartridge gear 116 rotates, and the direction of rotation of the cartridge gear 116. A specific unit of measure of cosmetic material is a dose unit dose unit 118.

In one example, the pitch of the cartridge lead screw 202 is about 1 mm, with one full rotation of the cartridge lead screw 202 dispensing about 1 mL of cosmetic material from the cartridge 114.

In another example, due to the shape of the cartridge key 162 of the cartridge 114 the circumferential groove 134 may be a notch or a groove about a portion of the circumference of the cartridge 114, rather than extend fully around the perimeter of the cartridge 114 to secure the cartridge 114 to the detent plunger 146 in substantially the same manner.

FIG. 6 is a perspective view of the cartridge gear 116, according to one example. The cartridge gear 116 may be a spur gear that includes a key cutout 163 that corresponds to the shape of the cartridge key 162 of the cartridge 114. The cartridge gear 116 may further have a collar 168 that rotatably connects to an inside surface of the gearhousing 170 to align and support the position of the cartridge gear 116 and the corresponding motor gear 124. The cartridge gear 116 may have a plurality of cartridge gear slots 148 for use with the optical encoder 192 to detect angular position of the cartridge gear 116 and the cartridge lead screw 202.

FIG. 7A is a perspective view of the bottom plate 166, according to one example. The bottom plate 166 is connected to the dispenser body 106 and/or the lower body section 154, restrains the plurality of cartridges 114 disposed inside the cosmetic dispenser 100, and connects the cosmetic dispenser 100 to the inductive plate 176 disposed below the bottom plate 166.

The bottom plate 166 has a plurality of cartridge through holes 172 to allow for the insertion, removal, and securement of the plurality of cartridges 114. Each cartridge through hole 172 includes a base key cutout 165, and the shape of the base key cutout 165 corresponds to the shape of the base key 164 of each cartridge 114 to prevent rotational motion of the second end of the cartridge 114, the portion in contact with the bottom plate 166, when the cartridge 114 is installed in the cosmetic dispenser 100.

Further, the bottom plate 166 has contact pins 174 (shown in FIG. 7B) that contact the inductive plate, providing electricity to the bottom plate 166, allowing the cosmetic dispenser 100 to charge the plurality of batteries 126 through contact or induction.

FIG. 7B is a perspective view of the bottom plate 166, viewed from the bottom, according to one example. The bottom plate 166 includes three cartridges through holes 172 disposed within the plate, and contact pins 174. When the bottom plate 166 is disposed within the cosmetic dispenser and upon the base 102, the contact pins 174 can conduct electricity from the base 102 to the bottom plate 166. The bottom plate 166 can then inductively charge the plurality of batteries 126 disposed above the bottom plate 166.

FIG. 8 is a perspective view of the base 102, according to one example. A power cord 104 is connected at a first end to the base 102. The power cord 104 is connected at a second end to a power source (not shown), providing power for the operation of the cosmetic dispenser 100 and for charging the plurality of batteries 126. The base 102 includes a base indentation 128 for placement of the inductive plate 176 and other portions of the cosmetic dispenser 100. The base indentation 128 may have the ability to inductively charge the plurality of batteries 126 using power supplied by the power cord 104. Further, it may also charge the cosmetic dispenser 100 through contact pins 174 disposed inside the bottom plate 166 when the bottom plate 166 is disposed within the base indentation 128.

Figure 9A:
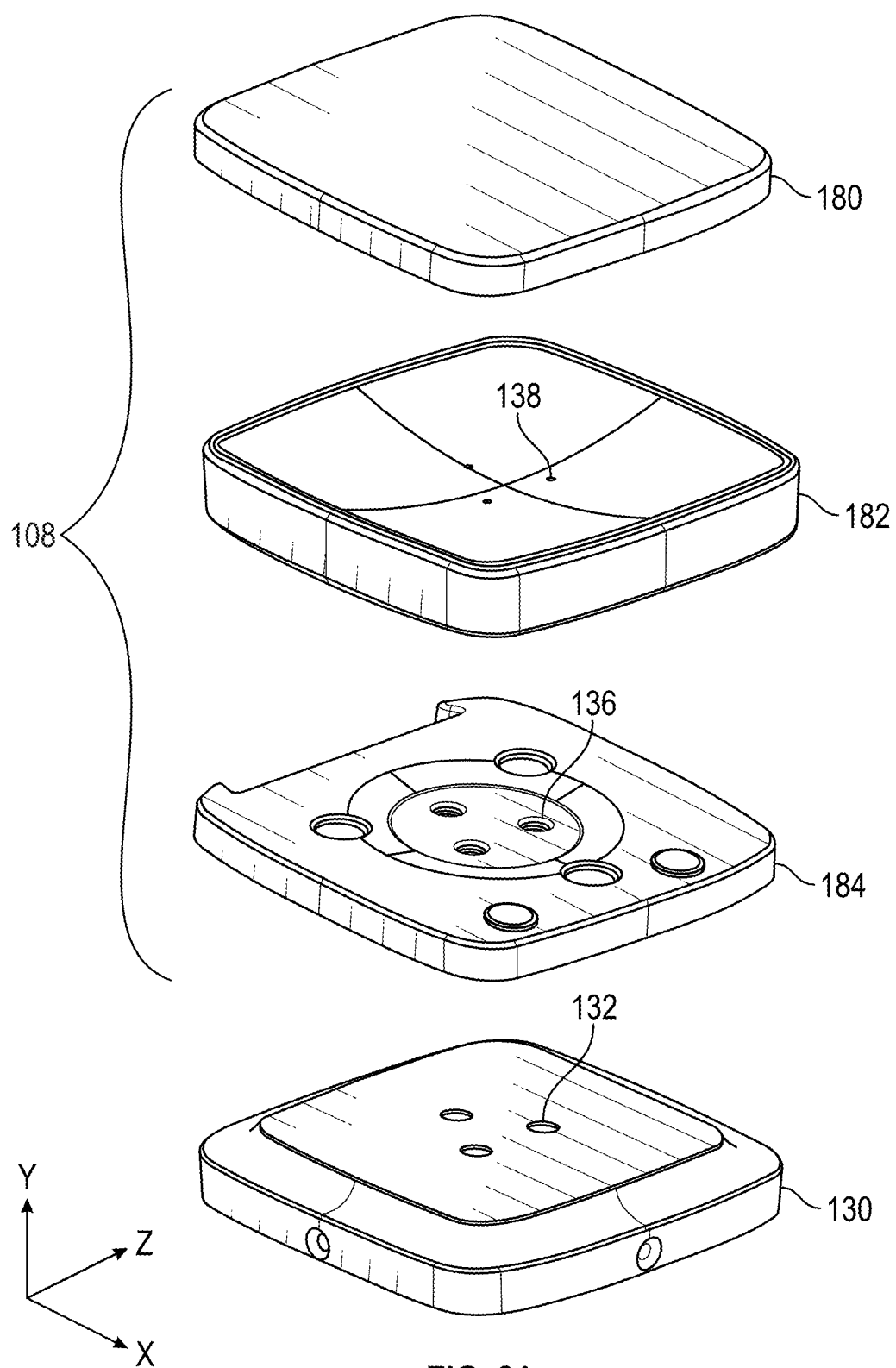
FIG. 9A is an exploded perspective view of a compact, disposed above a manifold, according to one example.

FIG. 9A is an exploded perspective view of the compact 108, disposed above a manifold 130, according to one example. The compact 108 includes a top lid 180, a compact base 182, and a bottom lid 184. The top lid 180 is disposed above the compact base 182, which is disposed above or within the bottom lid 184. The top lid 180 is secured to the compact base 182 by magnets, as described further by FIG. 9B. The compact base 182 includes a plurality of compact base through holes 138. In this example, there is one compact base through hole 138 for each cartridge 114 in the cosmetic dispenser 100. The bottom lid 184, having a plurality of bottom lid through holes 136, is disposed underneath the compact base 182. In this example there is one bottom lid through hole 136 for each cartridge 114 in the cosmetic dispenser 100, and the bottom lid 184 is disposed such that each bottom lid through hole 136 corresponds to and is connected to a compact base through hole 138 of the compact base 182.

The compact 108 is connected to the manifold 130, the manifold 130 connected to and disposed above the gearhousing 170, further disposed within the dispenser body 106 of the cosmetic dispenser 100, and the compact 108 is disposed above both the manifold 130 and the dispenser body 106. The manifold 130 includes one manifold through hole 132 for each cartridge 114 in the cosmetic dispenser 100, and the manifold 130 is disposed such that each manifold through hole 132 corresponds to and is connected to a compact base through hole 136 of the bottom lid 184. Further, each manifold through hole 132 of the manifold 130 corresponds to and is disposed above a gearhousing cartridge hole 178 of the gearhousing 170, providing a passage by which cosmetic material can be dispensed from the nozzle 160 of each cartridge 114 through the manifold 130, the bottom lid 184, and into the compact base 182.

The compact 108 may have a form such that there is only one orientation by which the compact 108 can connect to the cosmetic dispenser 100. In another example, it may be that the form of the compact 108 can connect to the compact 108 in more than one orientation.

Further, cosmetic material dispensed into the compact 108 may be prevented from flowing back out by use of a one way duckbill valve 194 (not shown) disposed within each of the compact base through holes 136 in the bottom lid 184 of the compact 108.

Figure 9B:
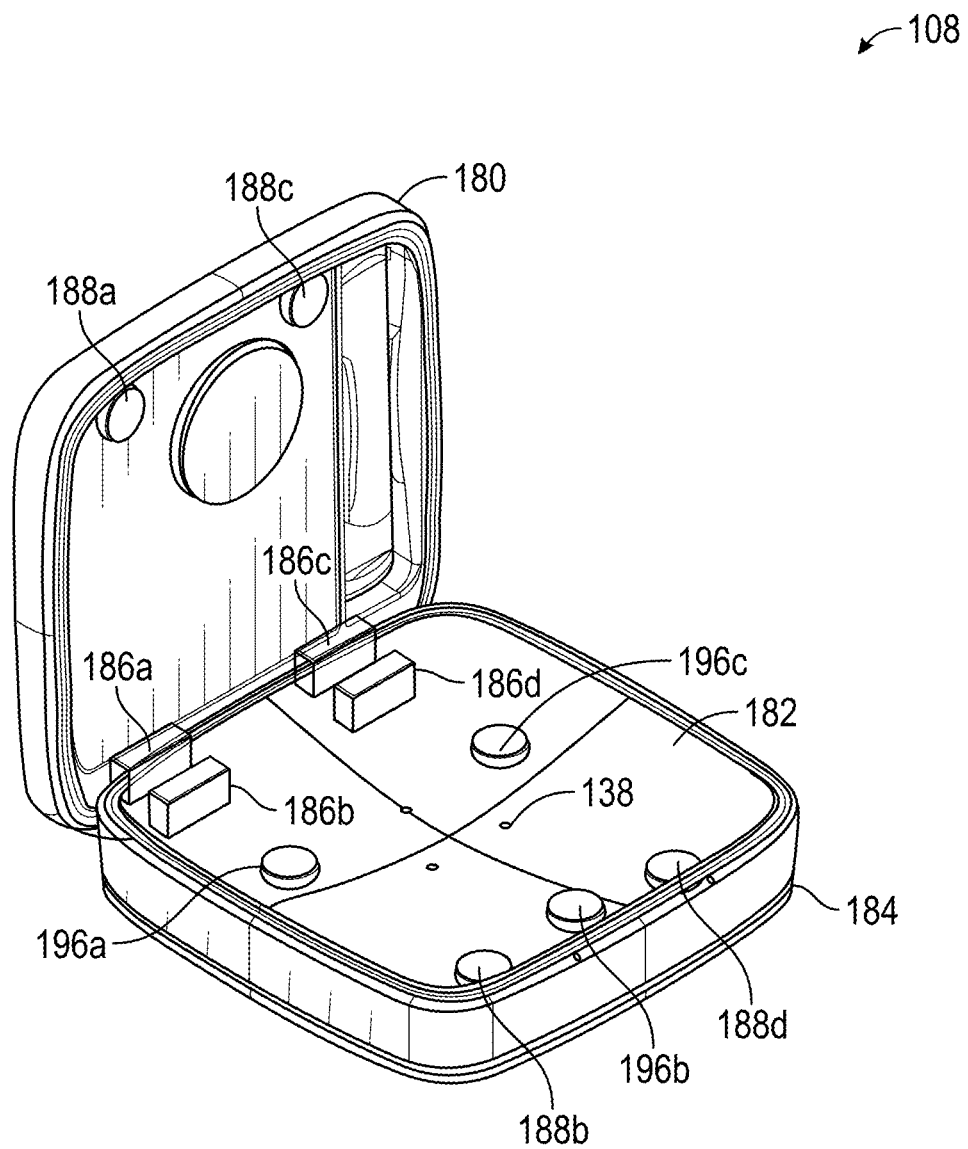
FIG. 9B is a perspective view of the compact in an open position, according to one example.

FIG. 9B is a perspective view of the compact 108 in an open position, according to one example. The compact 108 includes a top lid 180, a compact base 182, a bottom lid 184, a plurality of hinge magnets 186a, 186b, 186c, and 186d, a plurality of lid magnets 188a, 188b, 188c, and 188d, and a plurality of mounting magnets 196a, 196b, and 196c.

In one example, the compact base 182, the plurality of mounting magnets 196a-196c, a first half of the plurality of lid magnets 188b and 188d, and a first half the plurality of hinge magnets 186b and 186d, are disposed within the bottom lid 184, with the compact base 182 disposed above. The plurality of mounting magnets 196a-196c are disposed to magnetically connect the compact 108 to the cosmetic dispensing device 100, for example by connecting to the manifold 130 (FIG. 9A). The manifold 130, or portions of the surface of the manifold 130, may be formed of a ferrous material or contain corresponding magnets to magnetically attach to the plurality of mounting magnets 196a-196c.

A second half of the plurality of lid magnets 188a and 188c are disposed within a side of the top lid 180, and a second half of the plurality of hinge magnets 186a and 186c are disposed within a side of the top lid 180. The hinge magnets 186b and 186d are disposed within a side of the bottom lid 184 such that they may be in contact with corresponding hinge magnets 186a and 186c in at least two planes, depending on a relative position between the top lid 180 and the bottom lid 184. The hinge magnets 186a and 186b have opposite magnetic polarity, as do the respective pairs of hinge magnets 186c and 186d, the lid magnets 188a and 188b, and the lid magnets 188c and 188d.

The plurality of 196 and the plurality of lid magnets 188a-188d may be disposed such that the plurality of bottom lid through holes 138 disposed in the compact base 182 are unobstructed to allow cosmetic material to flow from each of the cartridges 114 into the compact 108 as cosmetic material is dispensed.

In a case where the compact 108 is in an open position, the top lid 180 and the bottom lid 184 are positioned approximately in perpendicular planes, the hinge magnets 186a and 186c magnetically connected to the hinge magnets 186b and 186d, respectively. The magnetic force between each pair of the hinge magnets 186a and 186b and the hinge magnets 186c and 186d is sufficient to hold the top lid 180 in position relative to the bottom lid 184.

In a case where the compact 108 is in a closed position, the top lid 180 and the bottom lid 184 are positioned approximately in parallel planes, the hinge magnets 186a and 186c magnetically connected to the hinge magnets 186b and 186d, respectively, and the lid magnets 188a and 188c are disposed in corresponding positions, and magnetically connected with the lid magnets 188b and 188d, respectively, the magnetic connection between the pairs of hinge magnets 186a and 186b and the hinge magnets 186c and 186d, and between the pair of lid magnets 188a and 188b, and the pair of lid magnets 188c and 188d, sufficient to keep the top lid 180 connected to the bottom lid 184 in a closed position.

Since the top lid 180 is connected to the bottom lid 184 magnetically, the top lid 180 may be entirely removable from the bottom lid 184. Further, it may also be able to connect with the bottom lid 184 in a closed position in more than one orientation about the x-z plane, depending on the disposition of the plurality of the hinge magnets 186a-186d and the lid magnets 188a-188d within the top lid 180 and the bottom lid 184. Further, the top lid 180 may be able to pivot about the bottom lid 184, or vice versa, opening or closing about more than one axis, such as about the x-axis or the z-axis.

Alternatively, the plurality of mounting magnets 196a-196c may be substituted by one mounting magnet 196 of sufficient strength to secure the compact 108 to the cosmetic dispensing device 100.

Alternatively, the plurality of hinge magnets 186a-186d may be substituted by one hinge magnet 186a of sufficient strength in the top lid 180 and by one hinge magnet 186b of sufficient strength in the bottom lid 184 to secure one side of the top lid 180 to the bottom lid 184 with the compact 108 in an open or a closed position.

Alternatively, the plurality of lid magnets 188a-188d may be substituted by one lid magnet 188a of sufficient strength in the top lid 180 and by one lid magnet 188b of sufficient strength in the bottom lid 184 to secure one side of the top lid 180 to the bottom lid 184 with the compact 108 in a closed position.

Figure 10:
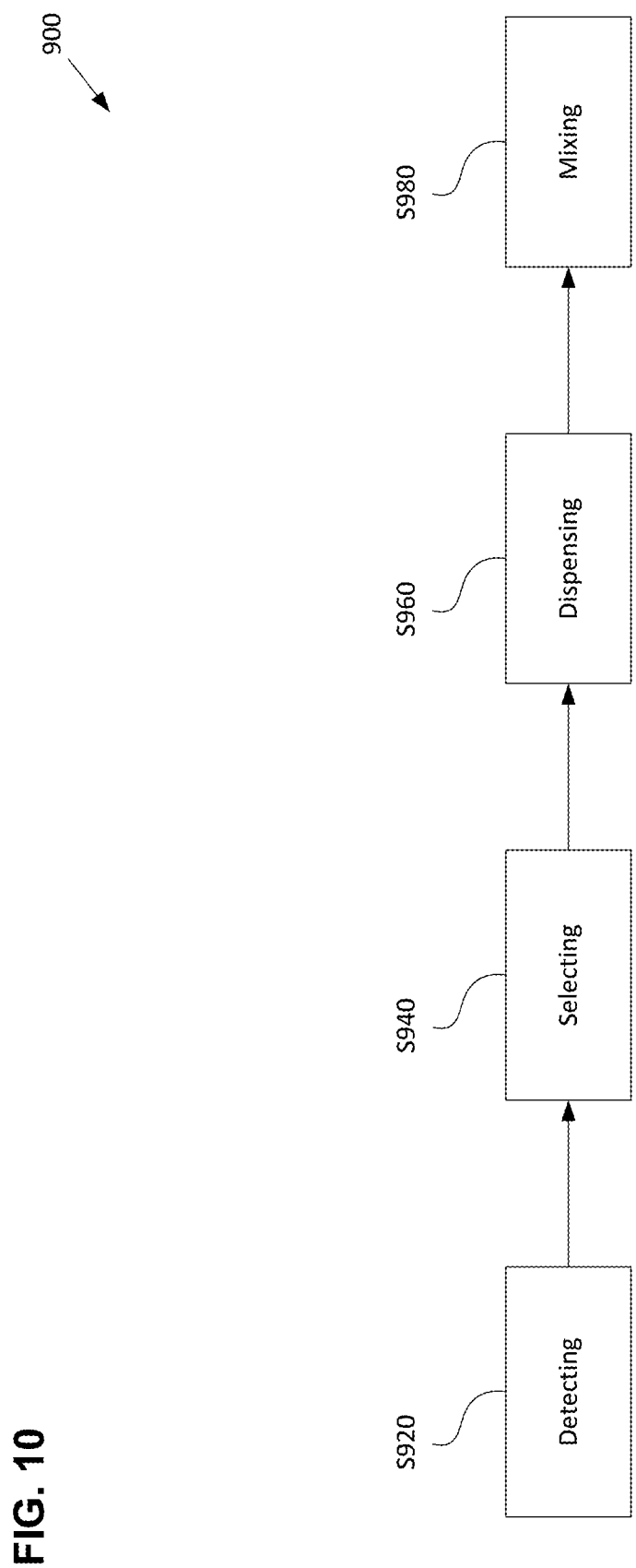
FIG. 10 is a diagram representing an example sequence of primary processes of a cosmetic formulation method 900, according to one example.

FIG. 10 is a diagram representing an example sequence of primary processes of a cosmetic formulation method 900, according to one example. The examples provided herein each have three cartridges, though the same process may be used by cosmetic dispenser 100 equipped with any number of cartridges 114. The cosmetic formulation method 900 includes a detecting process S920, a selecting process S940, and a dispensing process S960. An additional mixing process S980 may be performed by a user. The detecting processes S920, the selecting process S940, and the dispensing process S960 are performed by the cosmetic device 100 based on commands received from the controller 150, the controller 150 sending data to and receiving input from the user through the smart device 300 or by indicators on the cosmetic device 100 itself, as described in FIG. 3 and FIG. 4.

Figure 11:
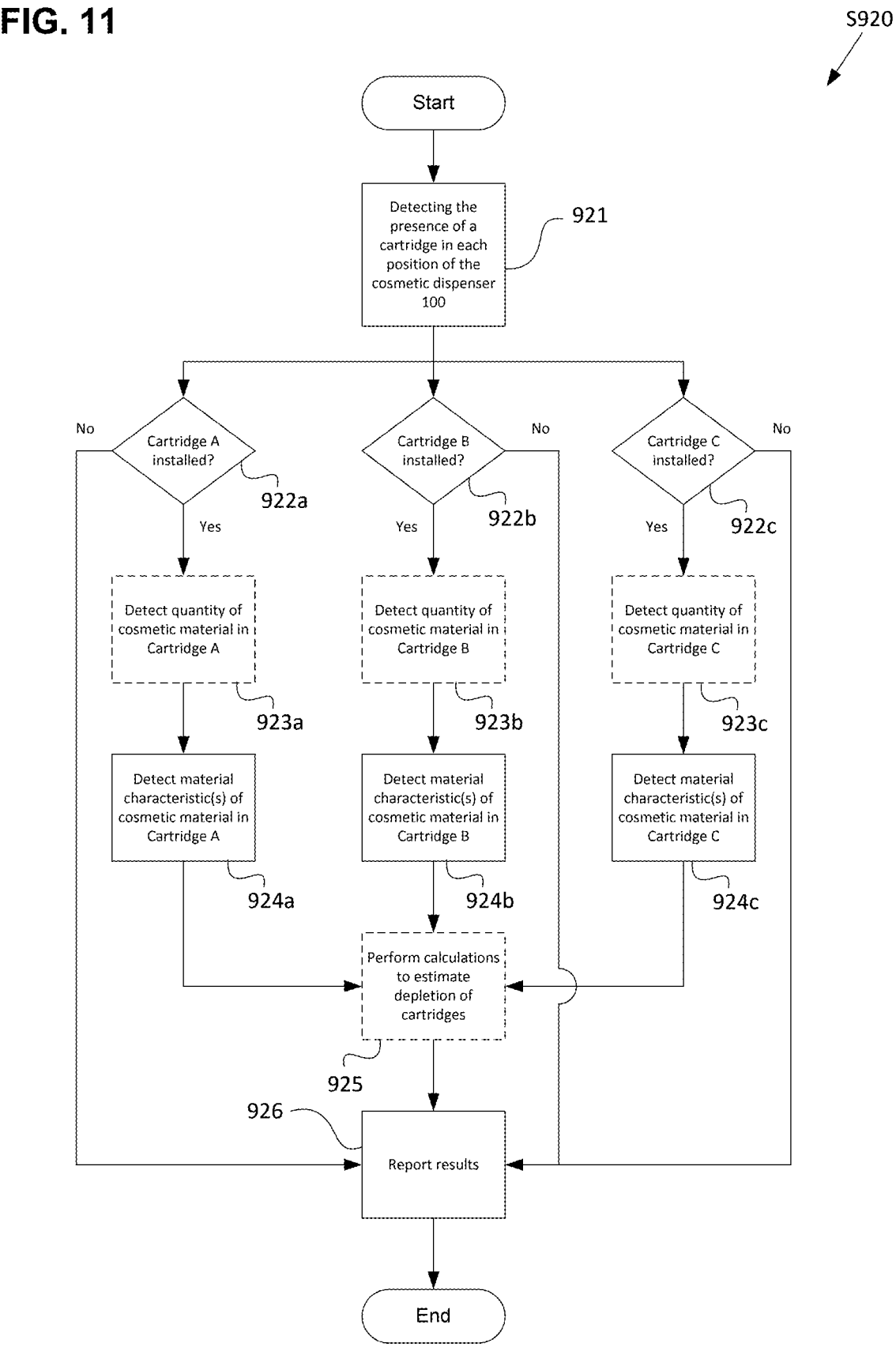
FIG. 11 is a process diagram representing an example a process of detecting cosmetic material in the cosmetic dispenser, according to one example.

FIG. 11 is a process diagram representing an example a process of detecting cosmetic material in the cosmetic dispenser 100, according to one example. S920 represents a process for detecting cosmetic material. The process S920 may include at least one of the steps of step 921 detecting removal and installation of a cartridge 114, step 922 detecting at least one material characteristic of the cartridge 114, an optional step 923 of detecting a quantity of cosmetic material in the cartridge 114, and an optional step 924 to calculate an estimated depletion of the cartridge(s) after a future dispensing operation is performed.

The optional step 923 of detecting a quantity of material in each of a plurality of cartridges 114 may include, for example, step 923a detecting a quantity of material of a cartridge A, step 923b detecting a quantity of material of a cartridge B, and step 923c detecting a quantity of material of a cartridge C, for example based on total net displacement (rotation) of the cartridge gear 116 detected by the optical encoder 192 since installation of each cartridge 114.

The optional step 924 of detecting at least one material characteristic in each of a plurality of cartridges 114 may include, for example, step 924a detecting at least one material characteristic of a cartridge A, step 924b detecting at least one material characteristic of a cartridge B, and step 924c detecting at least one material characteristic of a cartridge C. Material characteristics may include at least one from the set of consisting of color, texture, sheen, moisture, nutrient content, and chemical formulation. This detection may be performed based on a near field sensor disposed in the dispenser 100 which detects an RFID tag on the cartridge that stores information of the contents of the cartridge according to methods well understood in the art. Alternative methods of detection may be used such as bar code detection of a bar code printed on the cartridge, or detection using methods well understood in the art. The step of detecting the at least one material characteristic in each of the cartridges may be performed before the optional step of detecting the quantity of cosmetic material in each cartridge.

Further, process S920 may include optional step 926 for reporting information that may be derived from historical usage data, of the user or aggregated across groups of users, such as which cartridge 114 within the cosmetic dispenser 100 is anticipated to be depleted of cosmetic material first and by when.

Figure 12A:
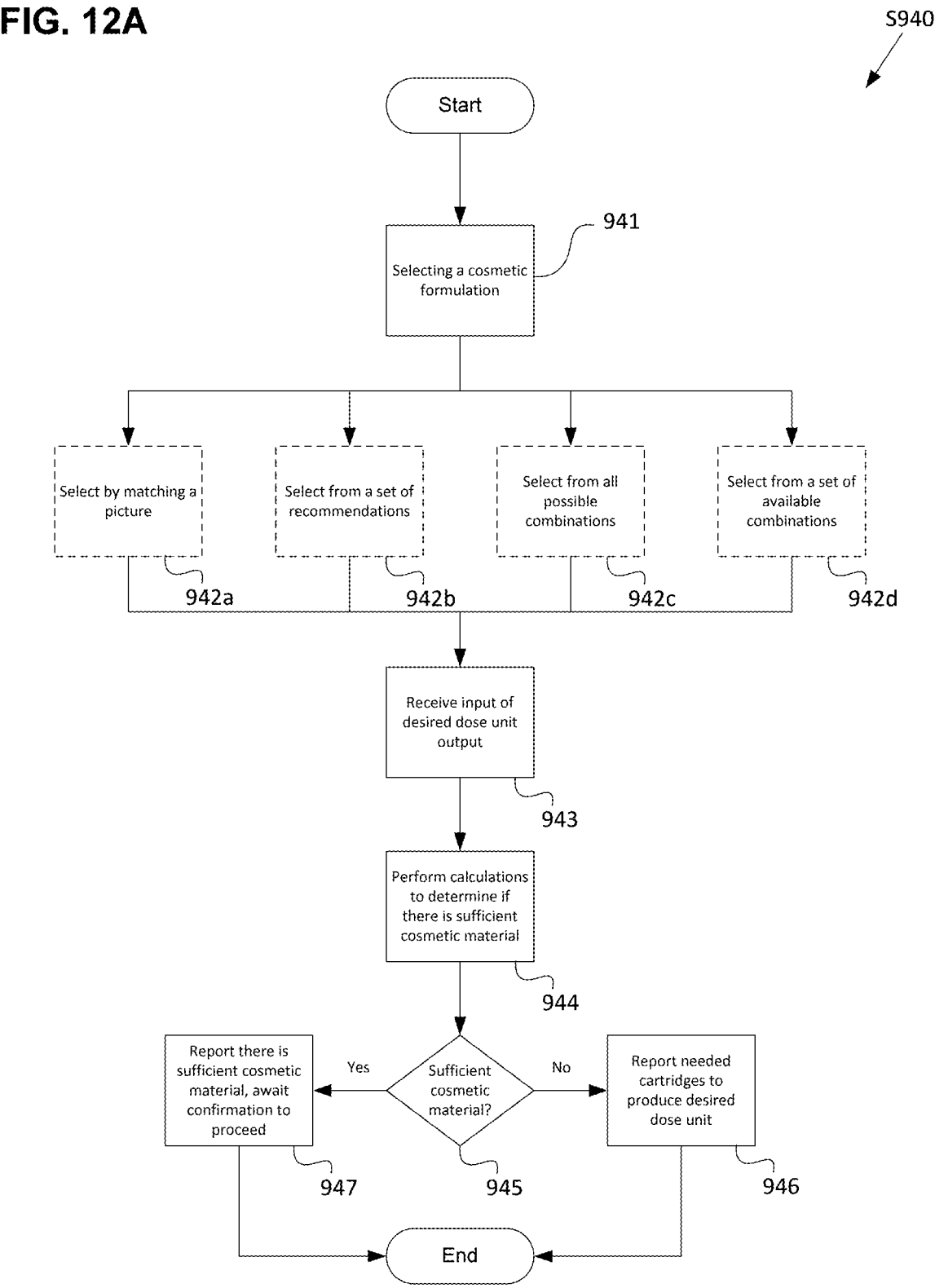
FIGS. 12A and 12B are process diagrams representing examples a process of selecting a cosmetic formulation, according to one example.

FIG. 12A is a process diagram representing an example a process S940 of selecting a cosmetic formulation, according to one example. S940 includes a process for selecting a cosmetic formulation. The process S940 includes steps of identifying combinations of cosmetic formulations possible based on the type and quantities of cosmetic materials present within the cosmetic dispenser 100, as established by the detecting process S920.

A step 942*d* may be based on a user selecting from a set of cosmetic formulations that are possible for the types and quantities of cosmetic material present within the cosmetic dispenser 100, or a step 942*c* allows the user to choose from a larger set of cosmetic material inventory 204 that is possible for types and quantities of cosmetic materials the cosmetic dispenser 100 is capable of using.

In another example, a step 943 of process S940 includes allowing a user to choose a desired dose unit 118. Varying the dose unit 118 can change the set of available cosmetic formulations from within the cosmetic dispenser 100 if a greater amount of one or more cosmetic materials is needed than is available to dispense a specific quantity of dose unit 118 for a specific cosmetic formulation.

For example, if cartridge A contains yellow cosmetic material, cartridge B contains red cosmetic material, and cartridge C contains green cosmetic material, and there is only one dose unit 118 of cartridge A remaining, the user would not be able to choose to dispense any combination of dose units 118 and cosmetic formulation that requires more than one dose unit 118 of yellow cosmetic material.

Further, the process S940 may include a step 942*a* for the user to select a cosmetic formulation based on matching of a photo, a step 942*b* for the user to select a cosmetic formulation based on recommendations, or selecting a cosmetic formulation based on another process. U.S. Pat. No. 8,634,640, describes a method for selecting a color from an image or picture in a camera or electronic device, and using color reference data to substantially match the color, and is hereby incorporated as reference in its entirety.

In another embodiment, a skin diagnosis (sometimes referred herein as a skin profile) may be performed for providing a recommended plurality of predetermined colors for the user to select based on an analysis of the user's skin features. The skin diagnosis determines an appropriate color for the user based on an imaging operation performed on the user's face. Examples of known skin diagnosis tools in the art are: Lancome Diagnos ABS, HR Skinscope, Biotherm Bluesmart, Kiehl's Skinprofiler V.0, CA Dermanalyzer, and the Vichy Vichyconsult.

For cosmetic formulations that are possible but not available based on the results of the detecting process S920, the cosmetic dispenser 100 may communicate to the user what cosmetic materials are necessary to dispense such cosmetic formulations.

In one example, in step 944 the user selects a dose unit 118 of a cosmetic formulation presently unavailable. Step 944 may determine what cosmetic materials, such as what type of cartridges 114 are needed to mix and dispense the selected cosmetic formulation.

In another example, step 944 may determine what additional cosmetic formulations may become available if a specific cartridge 114 is replaced with a full but otherwise identical cartridge 114.

In another example, step 944 may determine what additional cosmetic formulations may become available if a cartridge 114 is replaced with another cartridge 114 containing different cosmetic material.

Step 945 determines whether to proceed to step 947 to prompt the user to confirm and proceed with dispensing a cosmetic formulation or to proceed to step 946 to report what cartridge or cartridges 114 are needed to dispense the desired cosmetic formulation, based on the outcome of step 944.

Figure 12B:
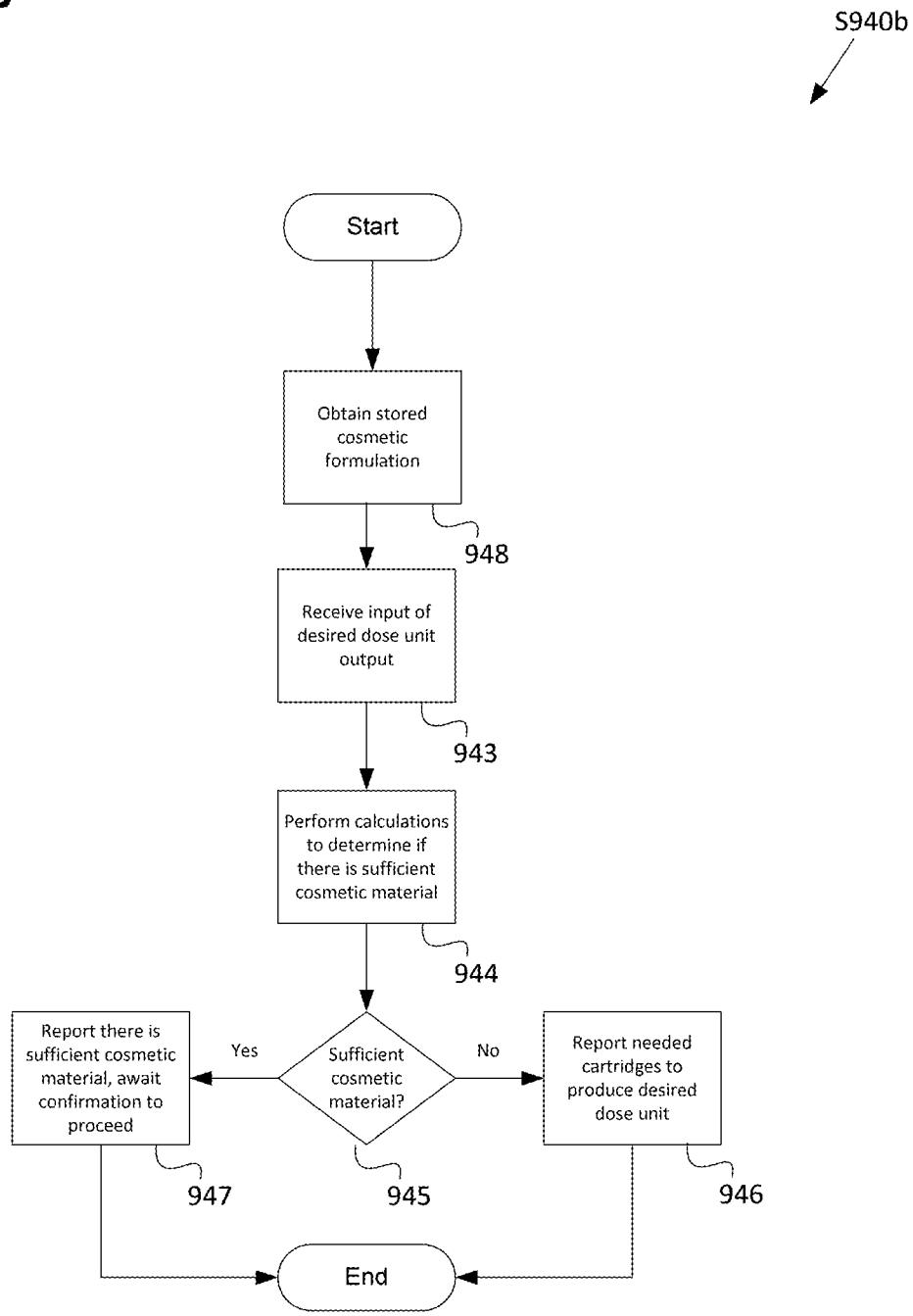

FIG. 12B shows an optional process S940*b* that is performed by the dispenser apparatus 100 alone after a cosmetic formulation has been previously received and is currently stored on the dispenser apparatus 100 in a step 948. The remaining steps 943 through 947 of S940*b* are identical to those of S940 described by FIG. 12A. The process of FIG. 12B may be performed without an existing connection being established between the dispenser apparatus 100 and device 300.

Figure 13:
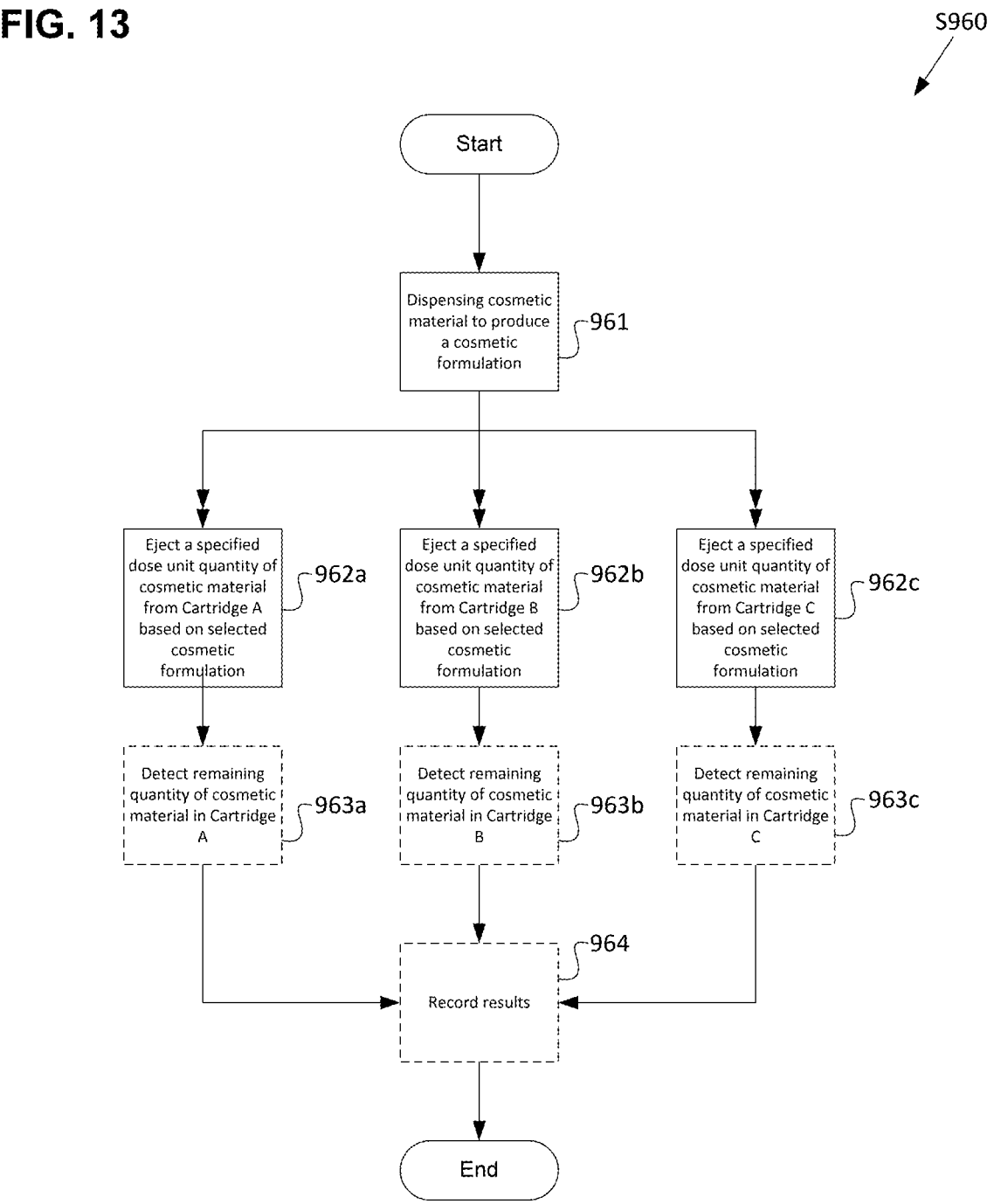
FIG. 13 is a process diagram representing an example a process of dispensing cosmetic material in the cosmetic dispenser, according to one example

FIG. 13 is a process diagram representing an example of a process S960 of dispensing cosmetic material in a cosmetic dispenser 100, according to one example. Step 961 represents a step for dispensing at least one dose unit of a cosmetic formulation. The process S960 includes steps 962*a* through 962*c* of ejecting a requested quantity of cosmetic material from at least one cartridge 114 to produce a cosmetic formulation selected by the user in process S940, such that the cosmetic formulation may be applied, transported in a container, or is otherwise available to the user. The process S960 includes optional steps 963*a* through 963*c* of detecting the remaining quantity of cosmetic material in each of the cartridges and optional step 964 of recording the results in a memory of the dispensing apparatus.

After the dispensing process S960 is completed, the user may perform the process S980 of mixing the released cosmetic material manually, producing the requested cosmetic formulation.

Figure 14:
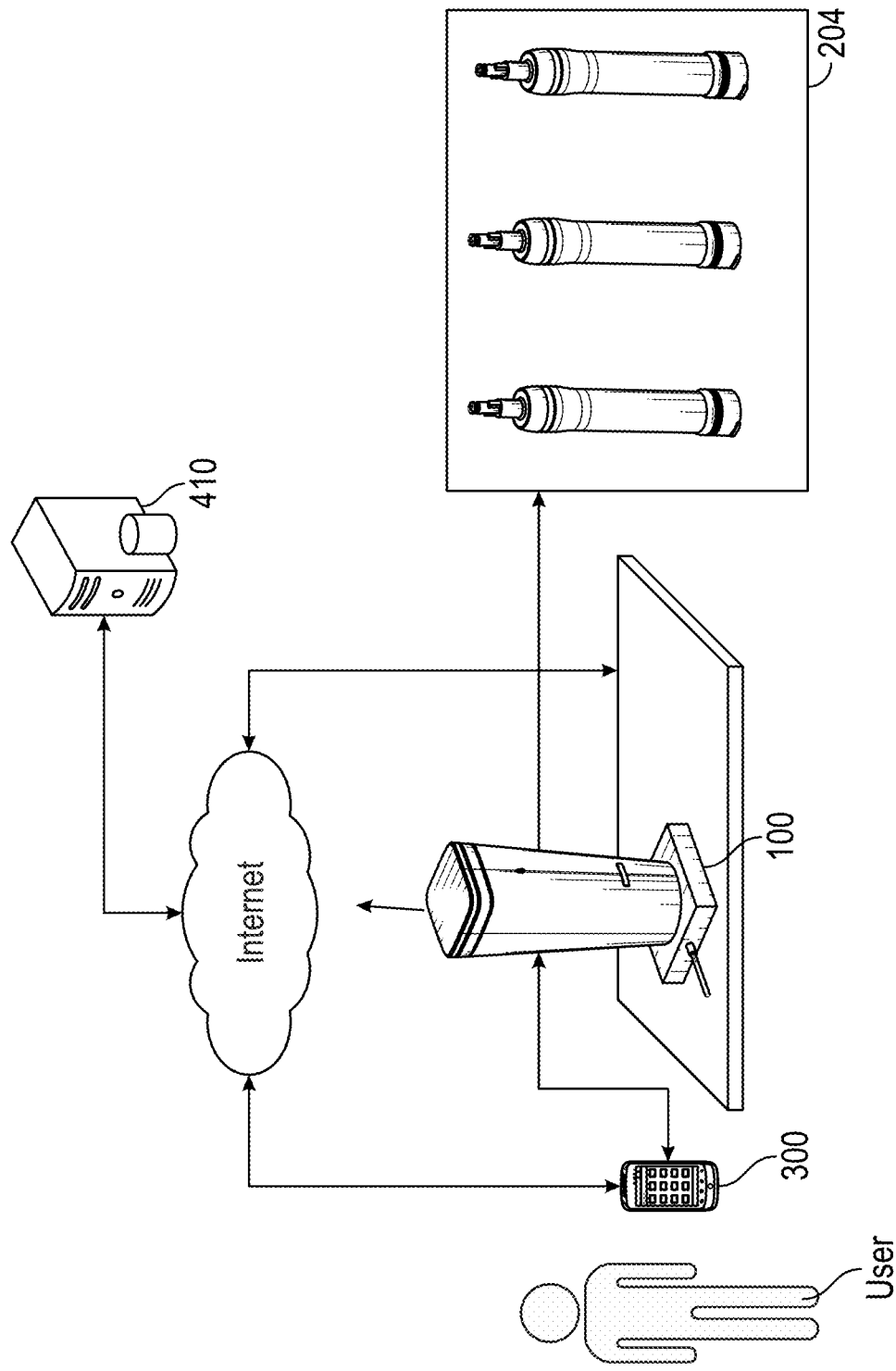
FIG. 14 is a diagram representing an example of a connected cosmetic dispensing system, according to one example.

FIG. 14 is a diagram representing an example of a connected cosmetic dispensing system, according to one example. A system 400, which implements the cosmetic dispenser 100 described above, includes at least the cosmetic dispenser 100 and a connected device 300. Optionally, the system may further include one or more external servers 410 which are implemented as part of a cloud-computing environment. Furthermore, the system may optionally include a cosmetic material inventory 204 which is an inventory of possible cosmetic material that may be inserted into the cosmetic device 100.

The connected device 300 may be a personal computer (PC), a laptop computer, a PDA (Personal Digital Assistants), a smart phone, a tablet device, a UMPC (Ultra Mobile Personal Computer), a net-book, or a notebook type personal computer. In the below examples, the connected device 300 is assumed to be a tablet device, such as an Apple iPad.

The connected device 300 is capable of performing wireless communication with the cosmetic dispenser 100 by way of a wireless communication interface circuitry 774 on the cosmetic dispenser 100. However, connected device 300 is also capable of having a wired connection to the cosmetic dispenser 100 by way of a USB interface 776 on the apparatus 100. Additionally, each device, including the cosmetic dispenser 100, may communicate with each other and the external one or more devices through an internet connection via an 802.11 wireless connection to a wireless internet access point, or a physical connection to the internet access point, such as through an Ethernet interface. Each connected device 300 is capable of performing wireless communication with other devices, such as through a Bluetooth connection or other wireless means as well.

The connected device 300 is configured to receive information from a user for use in generating a cosmetic formulation that will be used by the cosmetic dispenser 100 to dispense cosmetic material into the compact 108.

Figure 15:
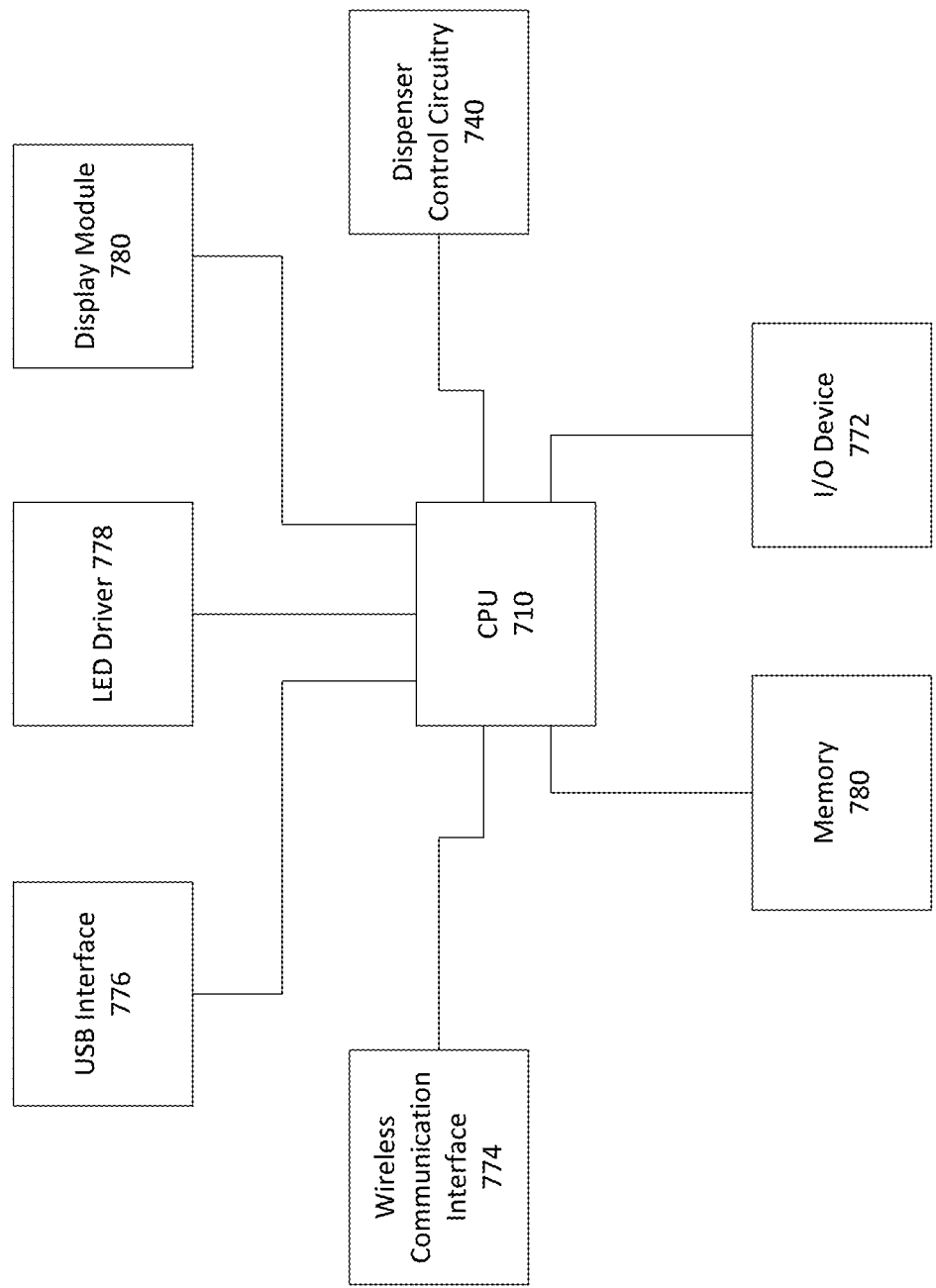
FIG. 15 is a diagram representing example circuitry of the controller and the cosmetic dispenser, according to one example.

FIG. 15 is a block diagram representing circuitry of the controller 150 and the cosmetic dispenser 100, according to one example. A central processing unit (CPU) 710 provides primary control over the separate circuitry components included in the apparatus, such as a dispenser control circuitry 740 (which may include control circuitry for the motors 112, circuitry for the optical encoder 192, and inductive sensor circuitry). The CPU 710 may also control an optional input/output device 772 (such as a keyboard or mouse), a memory 780, the wireless communication interface circuitry 774, the universal serial bus (USB) controller 776, an LED driver 778, and a display module 780. The LED driver 778 controls the pulsing of one or more indicator lights 122.

In an embodiment, circuitry includes, among other things, one or more computing devices such as a processor (e.g., a microprocessor, a quantum processor, qubit processor, etc.), a central processing unit (CPU), a digital signal processor (DSP), an application specific integrated circuit (ASIC), a field programmable gate array (FPGA), or the like, or any combinations thereof, and can include discrete digital or analog circuit elements or electronics, or combinations thereof.

In an embodiment, a module includes one or more ASICs having a plurality of predefined logic components.

In an embodiment, a module includes one or more FPGAs, each having a plurality of programmable logic components.

In an embodiment, circuitry includes one or more components operably coupled (e.g., communicatively, electromagnetically, magnetically, ultrasonically, optically, inductively, electrically, capacitively coupled, wirelessly coupled, or the like) to each other.

In an embodiment, circuitry includes one or more remotely located components.

In an embodiment, remotely located components are operably coupled, for example, via wireless communication, such as with a connected device 300.

In an embodiment, remotely located components are operably coupled, for example, via one or more communication modules, receivers, transmitters, transceivers, or the like.

In an embodiment, any of the CPU 710 or other components shown in FIG. 15 may be substituted with alternative circuitry elements. Examples of circuitry include memory that, for example, stores instructions or information. Non-limiting examples of memory include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of memory include Erasable Programmable Read-Only Memory (EPROM), flash memory, or the like.

In an embodiment, memory is coupled to, for example, one or more computing devices by one or more instructions, information, or power buses.

In an embodiment, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device.

In an embodiment, a module includes one or more user input/output components that are operably coupled to at least one computing device configured to control (electrical, electromechanical, software-implemented, firmware implemented, or other control, or combinations thereof) at least one parameter associated with, for example, determining one or more tissue thermal properties responsive to detected shifts in turn-ON voltage.

In an embodiment, circuitry includes a computer-readable media drive or memory slot that is configured to accept signal-bearing medium (e.g., computer-readable memory media, computer-readable recording media, or the like).

In an embodiment, a program for causing a system to execute any of the disclosed methods can be stored on, for example, a computer-readable recording medium, a signal-bearing medium, or the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital or an analog communication medium (e.g., a fiber optic cable, a waveguide, a wired communications link, a wireless communication link (e.g., receiver, transmitter, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

In an embodiment, circuitry includes acoustic transducers, electroacoustic transducers, electrochemical transducers, electromagnetic transducers, electromechanical transducers, electrostatic transducers, photoelectric transducers, radio-acoustic transducers, thermoelectric transducers, or ultrasonic transducers.

In an embodiment, circuitry includes electrical circuitry operably coupled with a transducer (e.g., an actuator, a motor, a piezoelectric crystal, a Micro Electro Mechanical System (MEMS), etc.).

In an embodiment, circuitry includes electrical circuitry having at least one discrete electrical circuit, electrical circuitry having at least one integrated circuit, or electrical circuitry having at least one application specific integrated circuit.

In an embodiment, circuitry includes electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs.

[Personalized Cosmetic Ecosystem]

Figure 16:
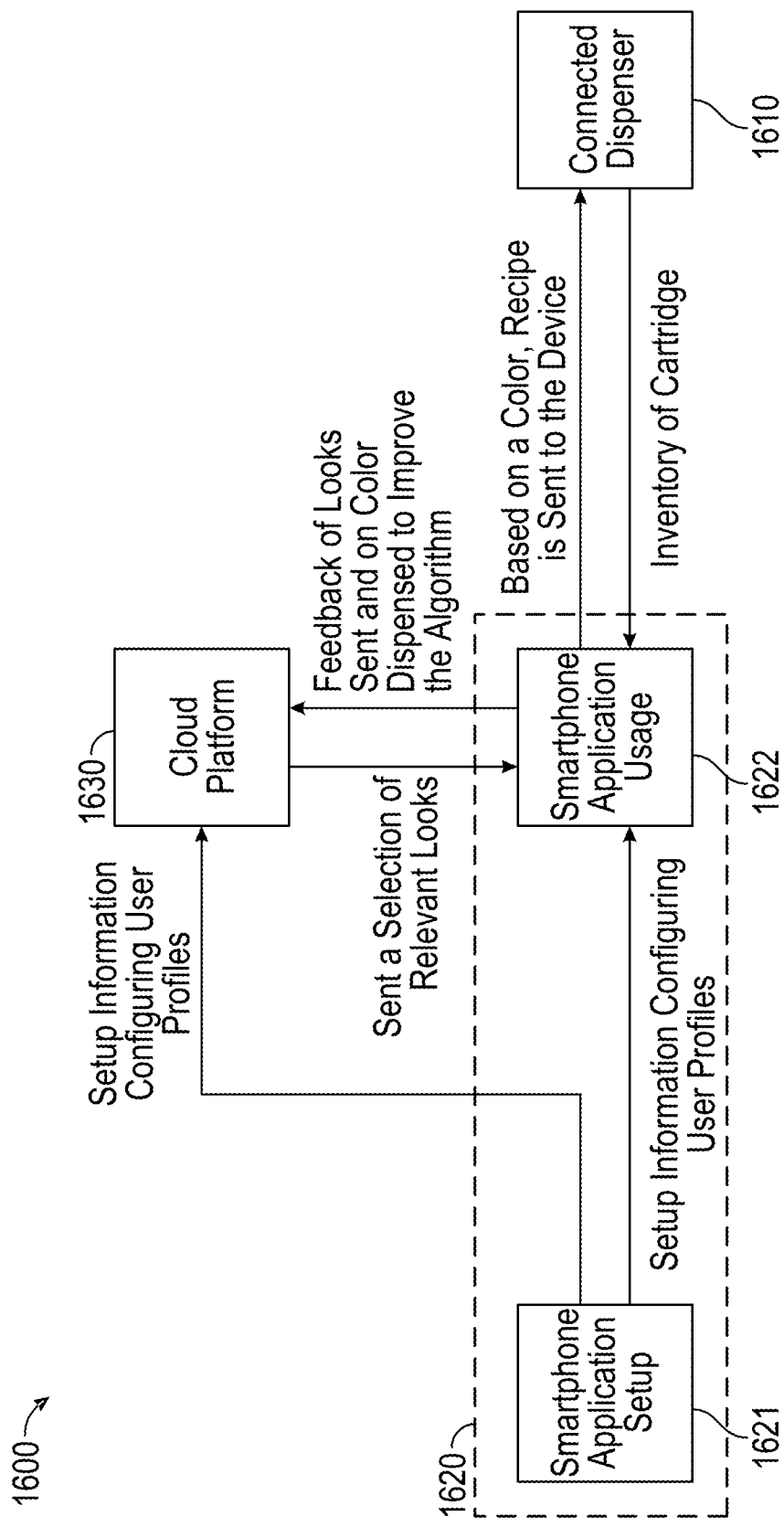
FIG. 16 shows components of an eco-system that utilizes the cosmetic dispenser to make personalized doses for a user.

FIG. 16 shows components of the ecosystem 1600 which are common to each type of product. The ecosystem includes the dispenser 1610, a user smartphone device 1620, and a cloud platform 1630. The smartphone is shown to include two functional blocks of the smartphone application ("app") setup 1621 and the smartphone application usage 1622. The smartphone application setup 1621 will be described in detail below with regard to the different personalization examples and it involves establishing the initial setup information for configuring a user profile of the user. The setup information can then be utilized when the smartphone application is being used and it can also be sent to the cloud platform 1630 for use in sending a selection of relevant looks for the user.

Usage of the smartphone application itself involves the user actually making selections that lead to the determination of a color, and performing interactive communication with the dispenser, such as sending the recipe to the dispenser and tracking the status of the dispenser (such as inventory and remaining volume of the cartridges in the dispenser). The smartphone application also performs interactive communication with the cloud platform. For instance, the smartphone application can receive the selection of relevant looks are described above, and it can also provide direct user feedback from the user on the looks the cloud platform previously sent and it can notify the cloud platform on the colors and recipes actually selected by the user and dispensed by the dispenser. Such feedback can provide a form of machine learning to the cloud platform and improve the algorithms used by the cloud platform.

[Personalized Lipstick Ecosystem]

Figure 17:
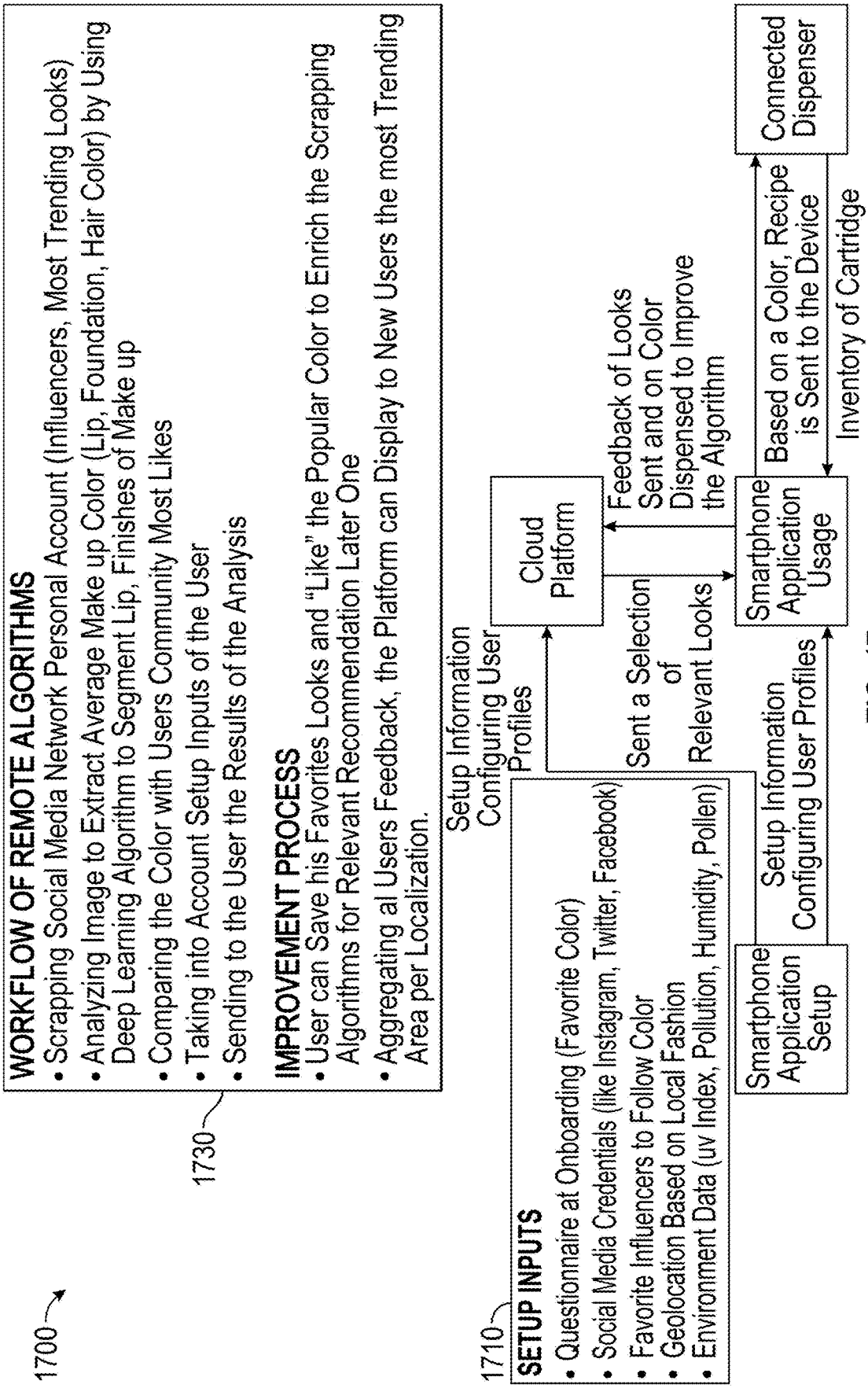
FIG. 17 shows an ecosystem that is built on proposing a trending lipstick color to a user.

FIG. 17 shows the above-described ecosystem (1700) that is built on proposing a trending lipstick color to the consumer after having analyzed trends on social media by combining favorite colors taste, geolocation, favorite influencers, past selection and likes. It gives the opportunity to the consumer to pick a color based on a look, virtually try it and adjust it if necessary to finally produce the formula on the spot with a connected dispenser. It is also possible to propose a color based on the user's outfit digitalized with a selfie picture. The consumer can save the most favorite colors and share it with his virtual community.

FIG. 17 shows that a user smartphone ultimately delivers a recipe to the dispensing device via a smartphone application ("app"). The smartphone app interacts with both the connected dispenser and a cloud platform. Prior to a user performing normal operations (usage) of the smartphone app, the app needs to be setup (1710) with setup information for configuring a user profile. The app setup can be based on the following setup inputs.

Questionnaire at onboarding (such as favorite color)
Social media credentials (like Instagram, twitter, Facebook)
Favorite influencers to follow color
Geolocation based on local fashion
Environment data (uv index, pollution, humidity, pollen)

The setup inputs are used during regular usage of the app on the smartphone, but they are also transmitted to a cloud platform, which may be an external server device that is connected via the Internet.

The actual usage of the smartphone app (1720) includes selecting a mode for lipstick selection. In the present example, the modes include a mode for selecting a social media trend recommendation by algorithms that are executed in the cloud platform (discussed later in more detail). Another mode allows the user to create their own lipstick color using a wide variety of color options.

Another mode may allow the user to match a lipstick color to their "look" based on selfie picture. In this example, the shade and finish selection on proposed picture is extracted. The user can virtually try on the lipstick in real time, the user can adjust the color presented. When the user is satisfied with the color, the user can touch a button displayed on the app to dispense the formula and an internal neural network will decompose the color requested into different color cartridge dose. After the recipe is sent to the dispenser and the lipstick shade is dispensed, the user can apply the lipstick.

Following use of the lipstick, the user can use the app to provide a feedback if she/he liked the rendering or not. The user can also save her favorite look and color to reuse later on, and the user can share the look and color on the web via a social media platform.

The cloud platform implements functions shown in 1730, such as a workflow of remote algorithms and an improvement process.

In the workflow performed by the cloud platform, social media network personal accounts (influencers, most trending looks) may be scraped for data related to lipstick colors. The cloud platform may perform analyzing of one or more collected images to extract average make up color (lip, foundation, hair color) by using a deep learning algorithm to segment lip finishes of make-up. For instance, the cloud platform may accomplish this by first detecting lips in a plurality of images using a known technique in the art (such as that described in U.S. Pat. No. 5,805,745, which is incorporated herein by reference). The cloud platform may then perform comparisons of an extracted color with colors most liked by one or more communities of users while also taking into account the setup inputs of the user received from the user's smartphone device. Taking into account all of the collected data, the final step is for the cloud platform to send to the user the results of the analysis in the form of the above-noted selection of relevant looks.

In the improvement process performed by the cloud platform and the smartphone app, the user can save her favorites looks and "like" the popular color to enrich the scraping algorithms for a relevant recommendation at a later time. The cloud platform can further aggregate all of the users' feedback, and the platform can send to new users the most trending area per localization.

The dispenser operations in block 1740 are already described in detail above, but they are summarized as follows. The dispenser receives a command to dispense a certain proportion of each cartridge. The dispenser dispenses on the top part and user can mix it to obtain the desired color. The dispenser send back inventory left of formula to the consumer app to make sure only dispensable colors are available in the UI when the user makes a selection.

Figure 18A:
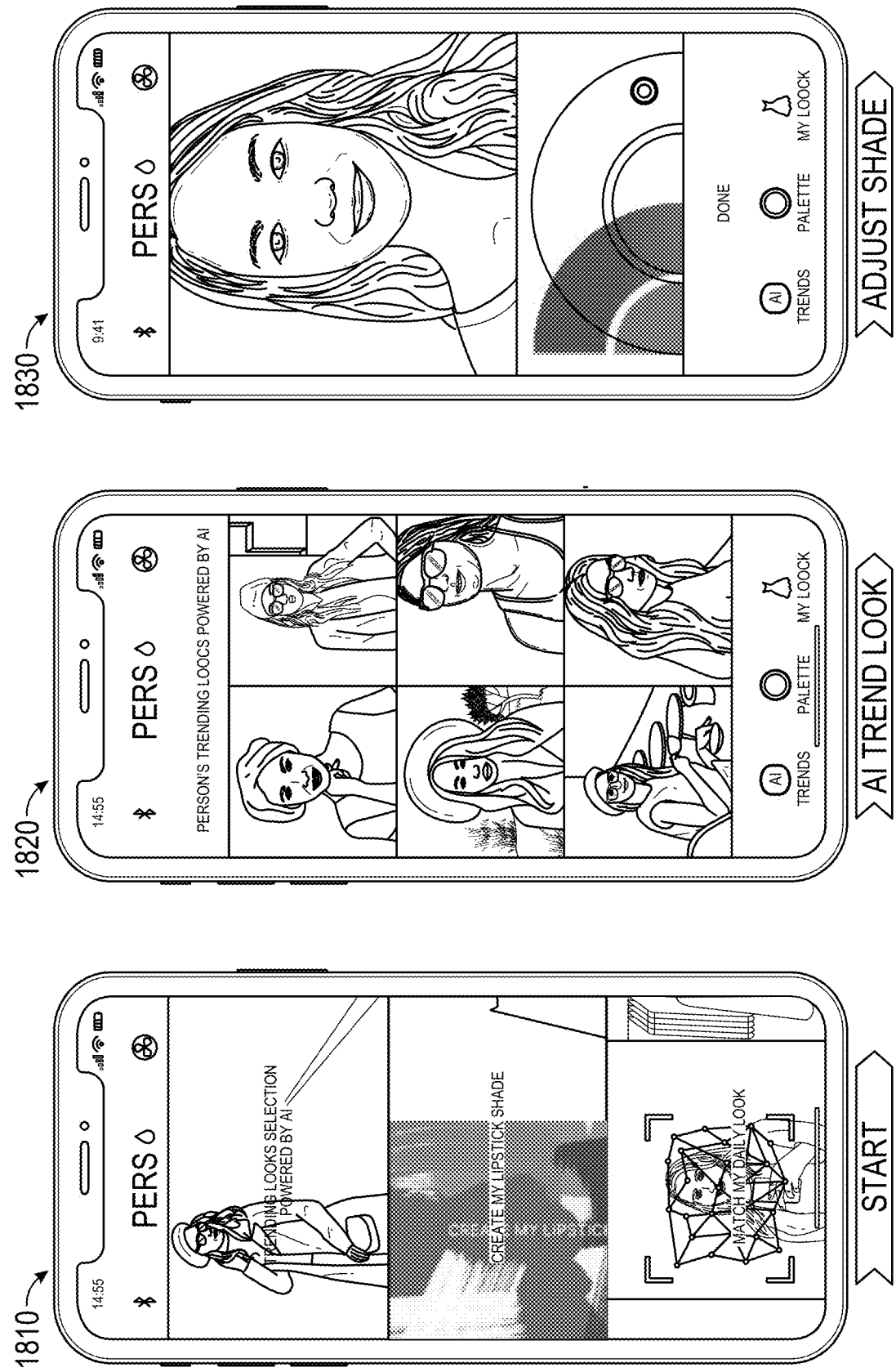
FIG. 18A shows an example flow of operations in the ecosystem for dispensing a personalized lipstick shade from the app perspective.
Figure 18A:
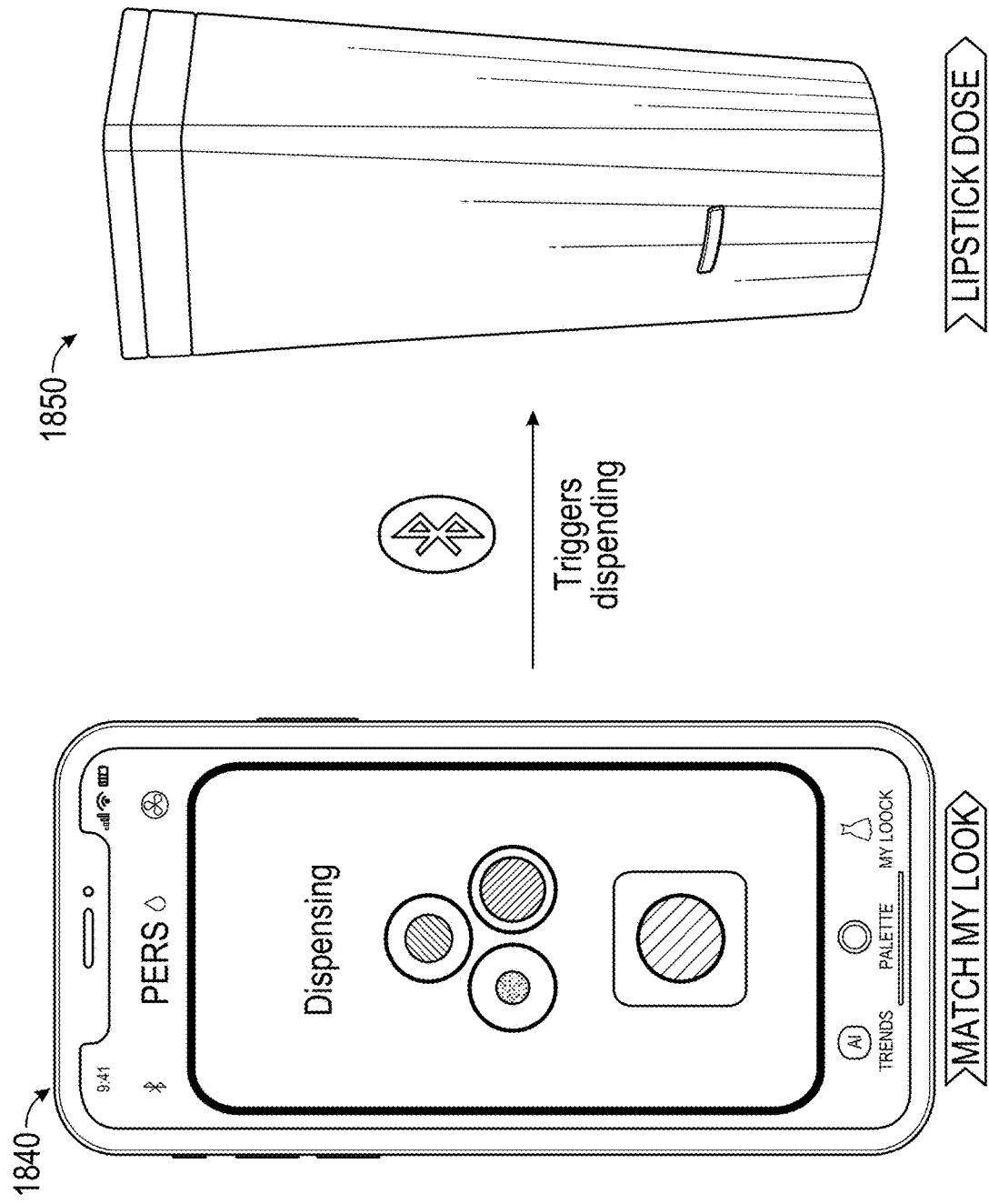

FIG. 18A shows an example flow of operations in the above-described ecosystem for dispensing a personalized lipstick shade from the app perspective. In step 1810, the user may select a "mode" as discussed above, which may be a mode for selecting a social media trend recommendation by the algorithms that are executed in the cloud; allow the user to create their own lipstick color using a wide variety of color options; or allow the user to match a lipstick color to their "look" based on selfie picture.

Step 1820 shows an example of a display when the mode is chosen for selecting a trending look powered by an AI algorithm of the cloud platform. Step 1820 also shows that a menu is provided at the bottom of the interface to allow the user to switch between the above-described modes.

Step 1830 shows an example of a display when the user has selected a potential shade and is allowed to adjust the shade using an appropriate adjusting mechanism such as a color palette or slider. The shade can be shown on the selfie of the user.

Step 1840 shows that after a color is ultimately selected by the user, the color is decomposed into a combination of the available colors contained in the cartridges of the dispensing device, and then the recipe is transmitted to the dispensing device for dispensing.

Figure 18B:
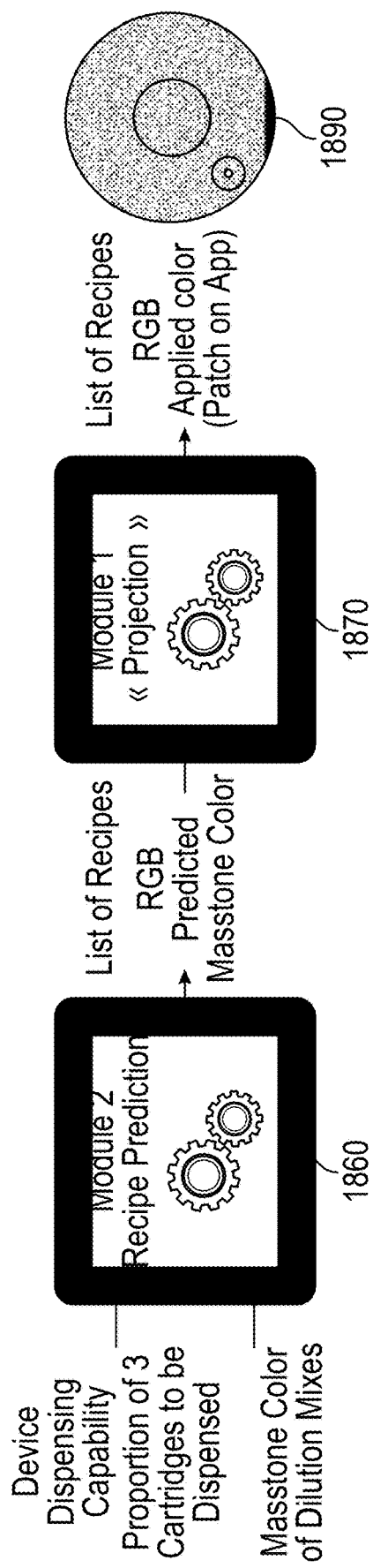
FIG. 18B shows an additional flowchart on how the algorithms of the smartphone app in the lipstick ecosystem may allow a user to view a shade of lipstick on the selfie of the user.

FIG. 18B shows an additional flowchart on how the algorithms of the smartphone app in the lipstick ecosystem may allow a user to view a shade of lipstick on the selfie of the user. A recipe prediction module 1860 ("Module 2) may receive as inputs the device dispensing capability, which is the set of three lipstick ingredient cartridges currently inside the dispensing device. Another input may be the masstone color of dilution mixes, which represent the actual color values that can be produced by the ingredients in the cartridge. The output from Module 2 is a list of recipes (actual dispensed amounts from each cartridge) and a corresponding RGB predicted masstone color resulting from each recipe. Module 1 (1870) can then perform projection of what the lipstick will look like on their actual lips based on the RGB masstone color in a recipe and the color of the user's lips (liptone), which results in a list of recipes and a corresponding RGB applied color. The relationship between the masstone color and the applied color based on the user's liptone may be predetermined and stored in advance. Thus, what may be presented to the user on the display is a palette based on a universe of RGB colors as shown in 1890.

Figure 18C:
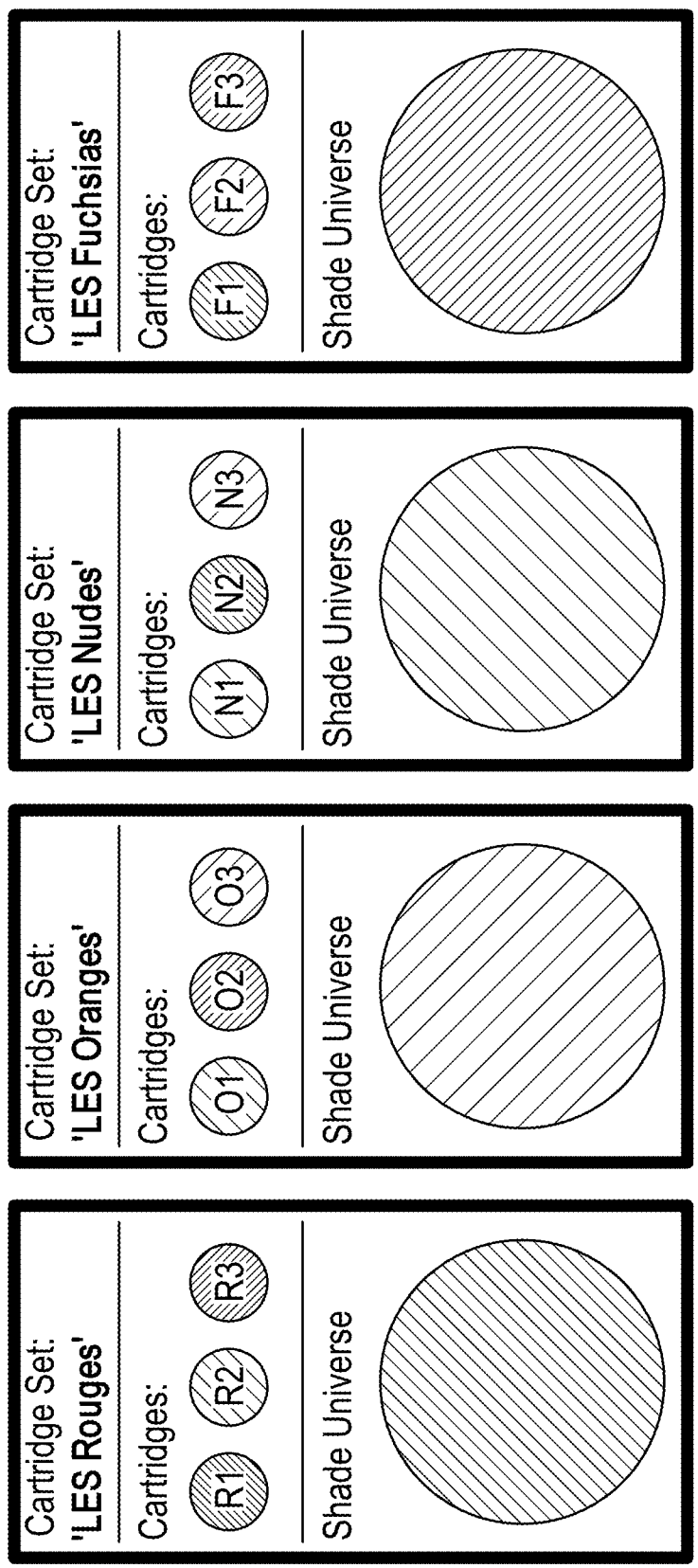
FIG. 18C further illustrates how the specific set of cartridges can result in different shade universes to present to the user.

FIG. 18C further illustrates how the specific set of cartridges can result in different shade universes to present to the user.

FIG. 18D shows how the "match my look" mode may operate on the app in the lipstick ecosystem. At state 1881, a user may input a selfie image that includes the user's outfit. A recommendation may be generated in different ways based on recognition of the colors and/or type of outfit in the image. For instance, a first approach ("Approach 1") at 1882 may use the 7 rules of color and harmony science to target forming a certain type of relationship between the lipstick shade and the colors of the outfit based on color wheel relationships as illustrated in Approach 1. Alternatively, in state 1883, a predetermine palette may be presented based on a make-up artist recommendation in view of a seasonal style of the outfit in combination with the color in the outfit.

Figure 18E:
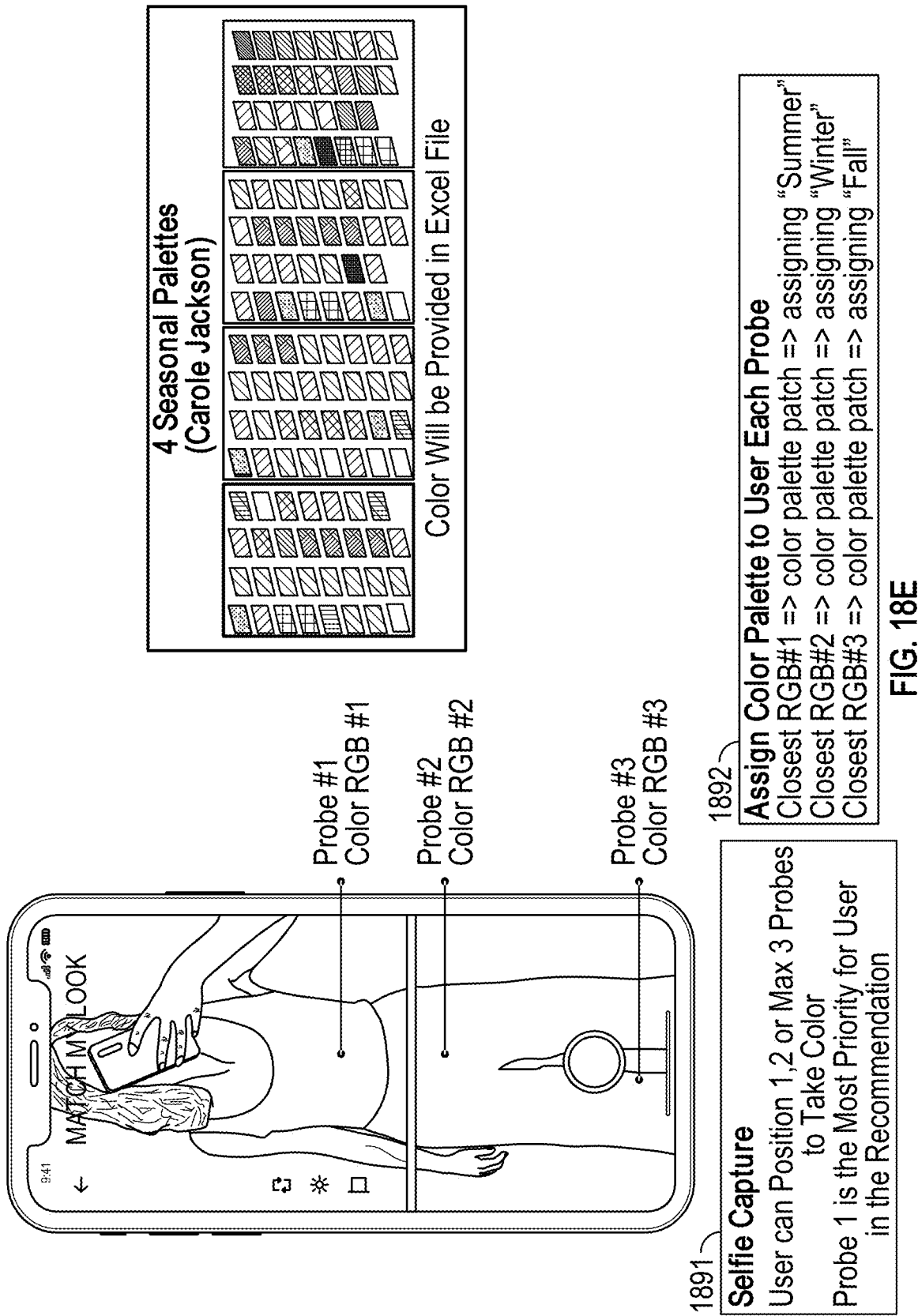
FIG. 18E shows details on how the recommendation engine for lipstick works based on the selfie of the user's outfit.
Figure 18E:
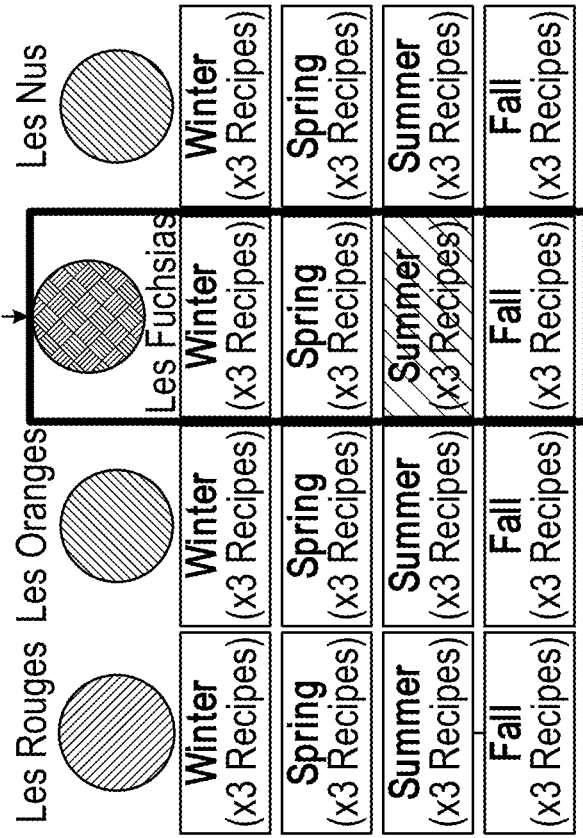

FIG. 18E shows more details on how the recommendation engine for lipstick works based on the selfie of the user's outfit. In state 1891, probes may be set by the user at different points on the outfit, where a single probe may have priority. In state 1892, a different color palette may be assigned to each probe based on the make-up artist recommendation palettes, or it could be based on a predetermined color wheel relationship as was shown in FIG. 18D. As seen in state 1893, the output may recommend colors based on the set of cartridges installed in the dispensing device, and based on the number and priority of the probes that the user decided to use. If desired, the user can also swipe to browse the options that would be available in other color wheels if other sets of cartridges were used. This may prompt the user to purchase a new set of cartridges.

[Personalized Skincare Ecosystem]

Figure 19:
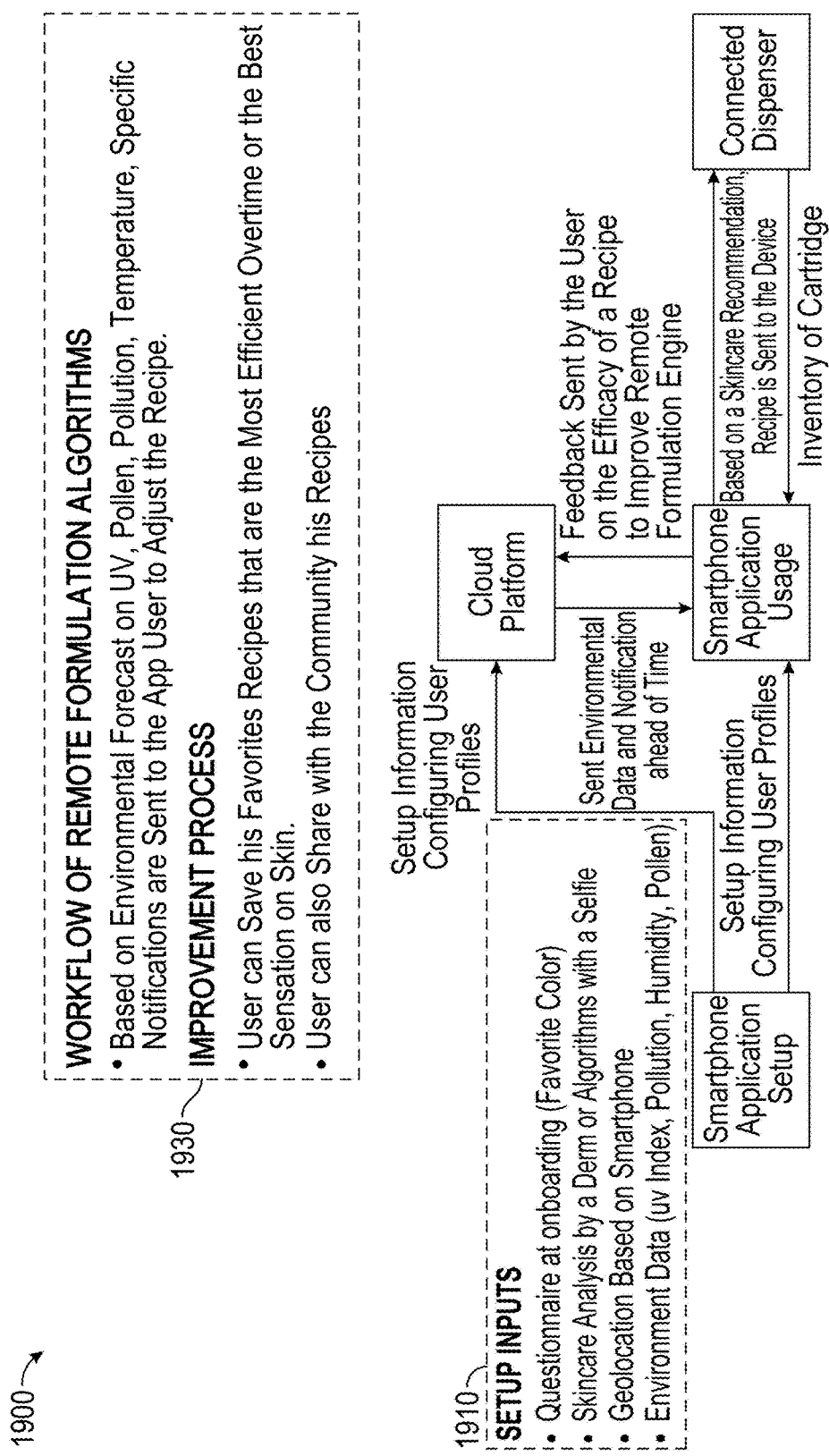
FIG. 19 shows an ecosystem that is built on proposing a skincare formulation to the user that is the most efficient for the user.

FIG. 19 shows the above-described ecosystem (1900) that is built on proposing a skincare formulation to the user that is the most efficient for the user based on the user's geolocation, environmental factor, UV cumulated exposure and clinical signed assessed with smartphone or dermatologist diagnosis. The system manages to adjust the actives proportion to obtain the most efficient recipe on a daily basis. The user can save their most favorite colors and share it with his virtual community.

FIG. 19 shows that a user smartphone ultimately delivers a recipe to the dispensing device via a smartphone application ("app"). The smartphone app interacts with both the connected dispenser and a cloud platform. Prior to a user performing normal operations (usage) of the smartphone app, the app needs to be setup (1910) with setup information for configuring a user profile. The app setup can be based on the following setup inputs.

Questionnaire at onboarding (such as favorite color)

Skincare analysis by a dermatologist or by AI algorithms with a selfie

Geolocation based on smartphone location detection function

Environment data (uv index, pollution, humidity, pollen)

The setup inputs are used during regular usage of the app on the smartphone, but they are also transmitted to a cloud platform, which may be an external server device that is connected via the Internet.

The actual usage of the smartphone app (1920) includes collecting environmental data based on geolocation and combine it with a smartphone diagnosis assessing clinical signs (wrinkles, dark spots, firmness, pores, fine lines, dullness).

The user can also collect data of a UV sensor, such as a wearable UV sensor as described in U.S. Pat. No. 10,060,787, incorporated herein by reference, that will actually give precise measurement of the cumulated UV exposure received. Based on historical data of skin assessment and environmental factor, the app will process the ideal formulation to fight against your skin aging signs and prevent from environment. When the user is satisfied with the formulation, the user can touch a button displayed on the app to dispense the formulation and an internal neural network will decompose the formulation requested into different cartridge ingredients. After the recipe is sent to the dispenser and the formulation is dispensed, the user can apply the formulation. The user can provide feedback on their favorite formulations for a specific period of time.

The cloud platform implements functions shown in 1930, such as a workflow of remote algorithms and an improvement process. In the workflow performed by the cloud platform, based on environmental forecast on UV, pollen, pollution, temperature, specific notifications are sent to the app user to adjust the recipe. For instance, there is a known correlation between environmental conditions and skin aging (see "*Assessing the impact of an aerial chronic urban pollution (UP) on some facial signs of differently-aged Chinese men*" at www.researchgate.net, and "*The skin aging exposome*" at www.jdsjournal.com). Additionally, giving an input of the geolocation of the user, which can provide an air quality determination using a tool such as Breezometer™ and a local UV index forecast (or the UV exposure can be obtained based on a UV sensor described above), the cloud platform can adjust the recipe to address environmental factors such as UV exposure and air quality. For instance, FIG. 20B below shows sample combinations of environmental factors and how they correlate to the ingredients in the cartridges.

In the improvement process performed by the cloud platform and the smartphone app, the user can save their favorites recipes that are the most efficient overtime or the best sensation on skin. The user can also share with the community their recipes.

The cloud platform can further aggregate all of the users' feedback, and the platform can send to new users the most trending formulizations area per localization.

The dispenser operations in block 1940 are already described in detail above, but they are summarized as follows. The dispenser receives a command to dispense a certain proportion of each cartridge. The dispenser dispenses on the top part and user can mix it to obtain the desired color. The dispenser send back inventory left of formula to the consumer app to make sure only dispensable ingredients are available in the UI when the user makes a selection.

Figure 20A:
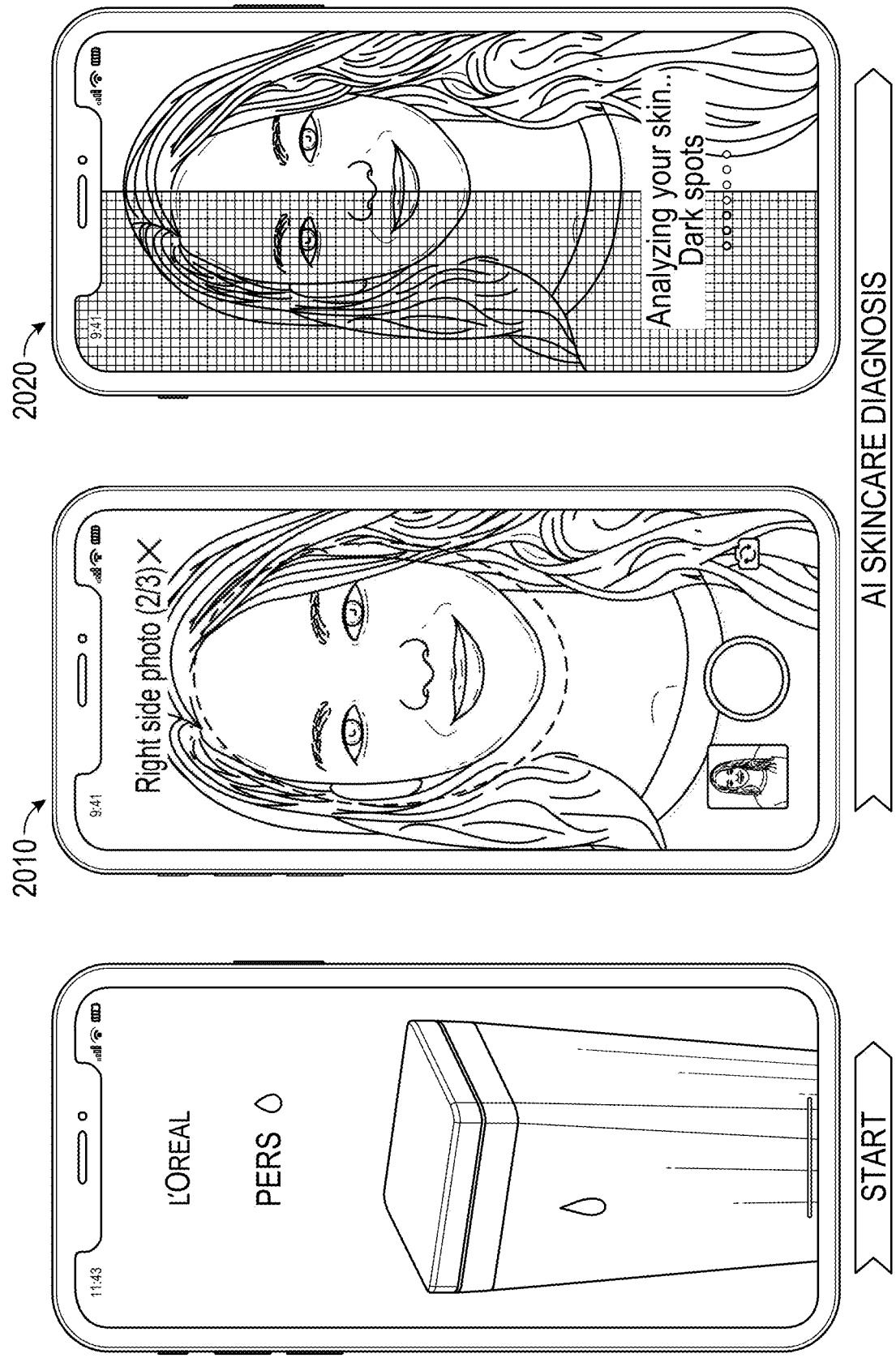
FIG. 20A shows an example flow of operations in the ecosystem for dispensing a personalized skincare formulation from the app perspective.
Figure 20A:
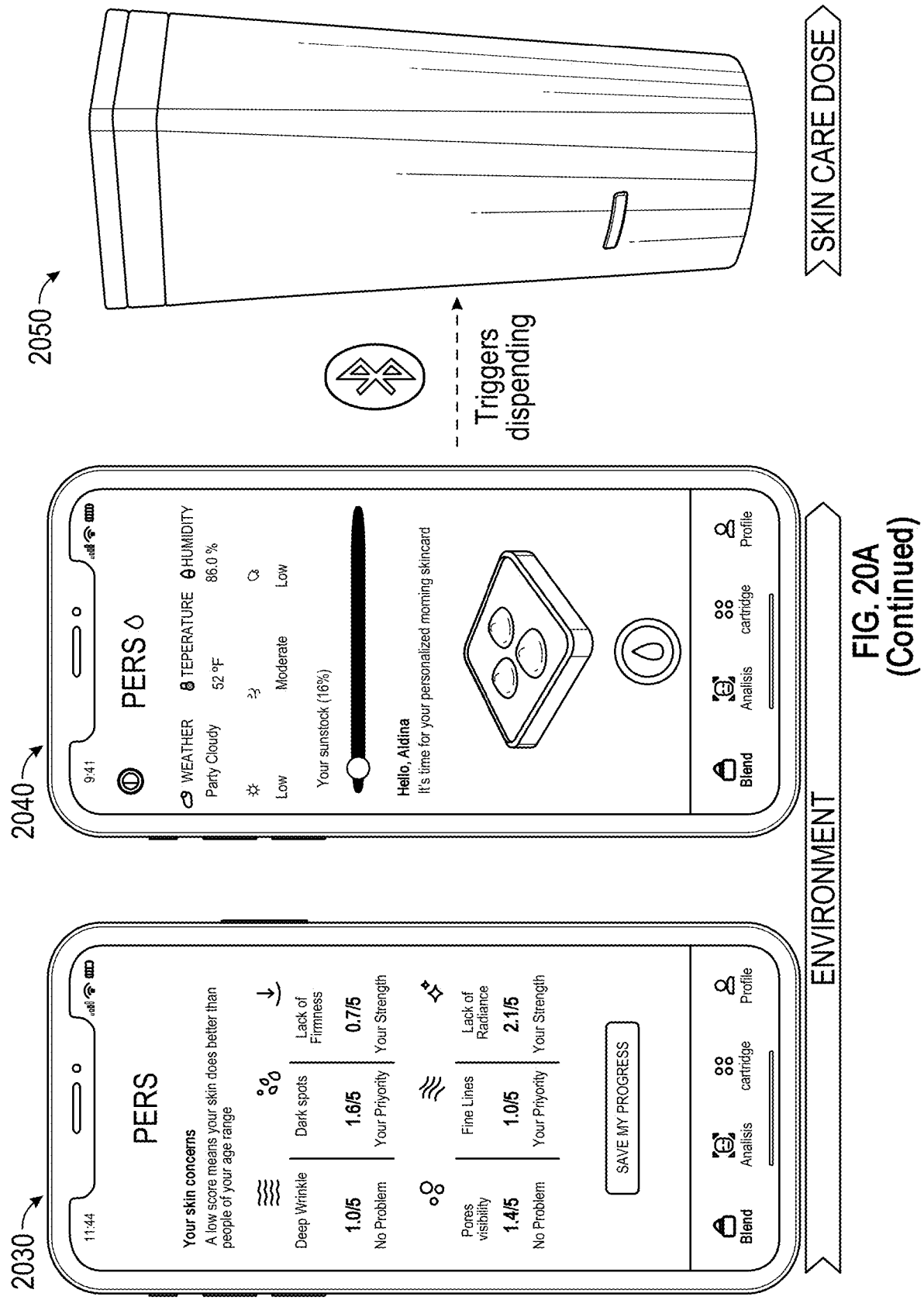

FIG. 20A shows an example flow of operations in the above-described ecosystem for dispensing a personalized skincare formulation from the app perspective. In step 2010, the user may perform a skincare diagnosis as discussed above, which may be performed by taking a 360° selfie picture, or a series of photos at different angles using the smartphone camera capability. In step 2020, the app performs an analysis of the user's skin to detect skin features, such as dark spots, wrinkles firmness, pores, fine lines, dullness, etc. A method for performing deep learning to perform training and execution of this type of detection is discussed in more detail below. Alternative known methods may be used as well, such as those described in U.S. Pat. Nos. 10,325,146 and 9,760,935, both of which are incorporated herein by reference.

Step 2030 shows the analysis results for one more of the skin features which are analyzed. The results may be shown as a score, which may be relative to people in the user's age range. For instance, each of the skin features may be presented on a five point scale, and features which represent a worse score than an average score may be highlighted as a priority for the user, while features which are better than the average may be presented as a strength.

Step 2040 shows that the app may present a recommended skincare formulation ("blend") which addresses the user's priority skincare concerns while taking into account the current environmental conditions. After the formulation is ultimately selected by the user, the formulation is decomposed into a combination of the available colors contained in the cartridges of the dispensing device, and then the recipe is transmitted to the dispensing device for dispensing at step 2050.

FIG. 20B shows an example of how a combination of different environmental factors determined to be present for a user can lead to different dosage amounts from three different cartridges. In this example, the cartridges respectively include ingredients director to deep damage recovery, cellular renewing, and daily skin aggressor protection (which may include an SPF ingredient and a pollution protection ingredient). In this example, a fixed dose of cartridge 1 may always be used for efficacy, while the proportions of the remaining cartridges vary based on the levels of UV or pollution that are present.

[Personalized Foundation Ecosystem]

Figure 21:
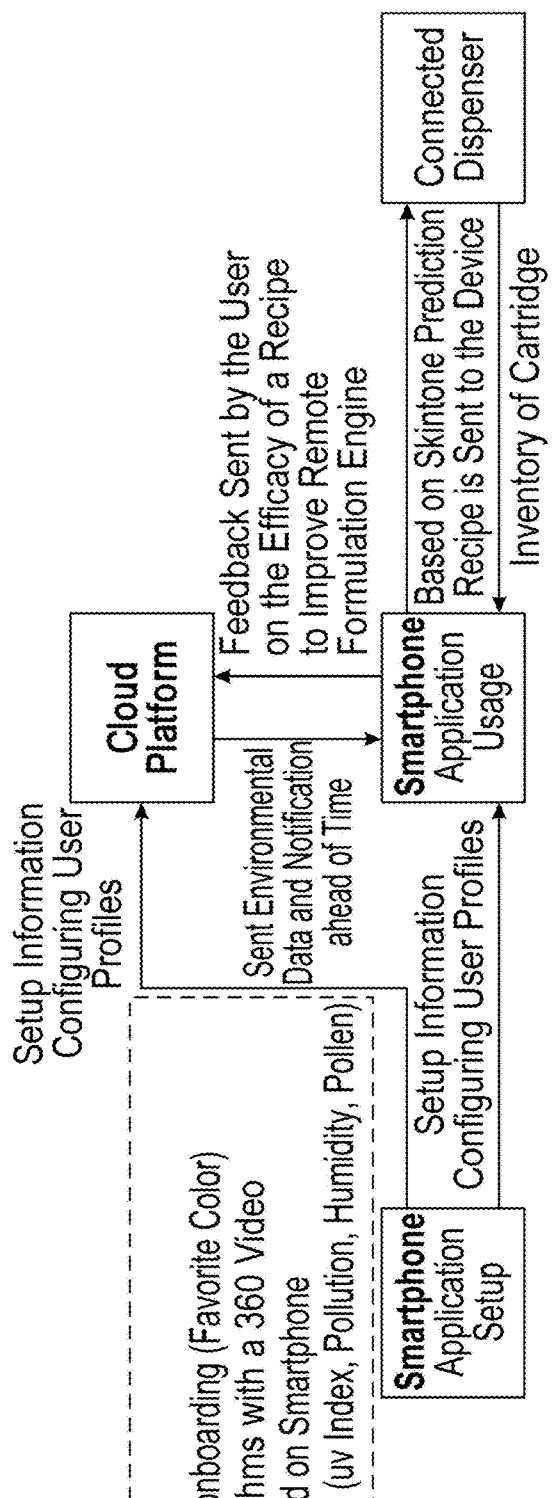
FIG. 21 shows an eco-system that is used to dispense a personalized foundation for a user.

FIG. 21 shows an eco-system 2100 that is used to dispense a personalized foundation for the user. The eco-system 2100 is using a deep learning algorithm to measure with a smartphone the user skintone. By combining with environmental information or make up tutorials, the system can adjust along the year to deliver to the consumer always the best foundation color that matches your tanning level/skintone variation. Based on weather forecast and UV exposure, the device can also increase skincare actives or SPF.

FIG. 21 shows that a user smartphone ultimately delivers a recipe to the dispensing device via a smartphone application ("app"). The smartphone app interacts with both the connected dispenser and a cloud platform. Prior to a user performing normal operations (usage) of the smartphone app, the app needs to be setup (2110) with setup information for configuring a user profile. The app setup can be based on the following setup inputs.

Questionnaire at onboarding (such as favorite color)
Detect the user's skintone with a 360° video and a skintone algorithm
Geolocation based on smartphone location detection function
Environment data (uv index, pollution, humidity, pollen)

The setup inputs are used during regular usage of the app on the smartphone, but they are also transmitted to a cloud platform, which may be an external server device that is connected via the Internet.

The actual usage of the smartphone app (2120) includes collecting environmental data based on geolocation and combine it with a smartphone diagnosis assessing the skintone of the user. While methods of determining a user's skintone for matching a foundation are known in the art, a method below related to a deep learning method will be discussed in detail. Depending on the user's skin condition, the app may determine to merge skincare actives with the foundation like SPF when the environmental conditions are not optimal. The app makes a determination based on the period of the year and the tanning level of the person to slightly adjust the foundation color to follow the skintone evolution. When the color is not perfecting the matching process, the user can send a feedback to the cloud to improve remotely the algorithms. In certain cases, the user may want to use the device to adjust primer color so as to achieve specific make up strategy by layering different colors.

The cloud platform implements functions shown in 2130, such as a workflow of remote algorithms and an improvement process. In the workflow performed by the cloud platform, based on environmental forecast on UV, pollen, pollution, temperature, specific notifications are sent to the app user to adjust the recipe by adding SPF. The cloud platform may shift the master skintone formula for the user that is sent when the tanning level of the consumer is different from the initial diagnosis.

In the improvement process performed by the cloud platform and the smartphone app, the user can save their favorites recipes that are the most efficient overtime or the best sensation on skin. The user can also share with the community their recipes. The cloud platform can further aggregate all of the users' feedback, and the platform can send to new users the most trending formulizations area per localization.

The dispenser operations in block 2140 are already described in detail above, but they are summarized as follows. The dispenser receives a command to dispense a certain proportion of each cartridge. The dispenser dispenses on the top part and user can mix it to obtain the desired color. The dispenser send back inventory left of formula to the consumer app to make sure only dispensable ingredients are available in the UI when the user makes a selection.

Figure 22A:
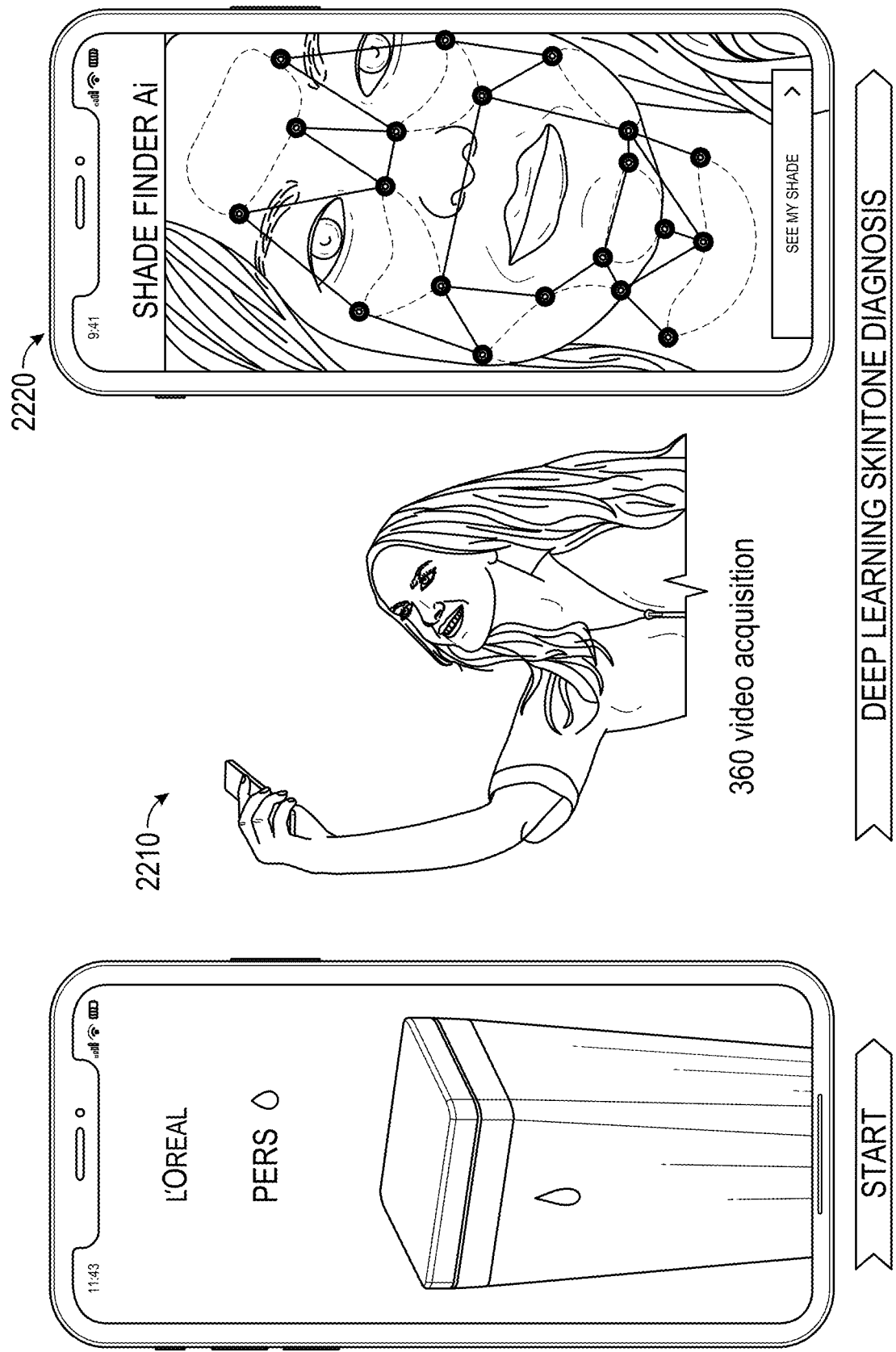
FIG. 22A shows an example flow of operations in the \ecosystem for dispensing a personalized foundation from the app perspective.

FIG. 22A shows an example flow of operations in the above-described ecosystem for dispensing a personalized foundation from the app perspective. In step 2210, the user may perform a skintone diagnosis as discussed above, which may be performed by taking a 360° selfie picture, or a series of photos at different angles using the smartphone camera capability. In step 2220, the app performs an analysis of the user's skin to detect the skintone and shade.

In step 2230, the app may present a recommended foundation ("blend") which matches the user's skintone while taking into account the current environmental conditions. After the foundation is ultimately selected by the user, the foundation is decomposed into a combination of the available ingredients contained in the cartridges of the dispensing device, and then the recipe is transmitted to the dispensing device for dispensing at step 2240.

Figure 22B:
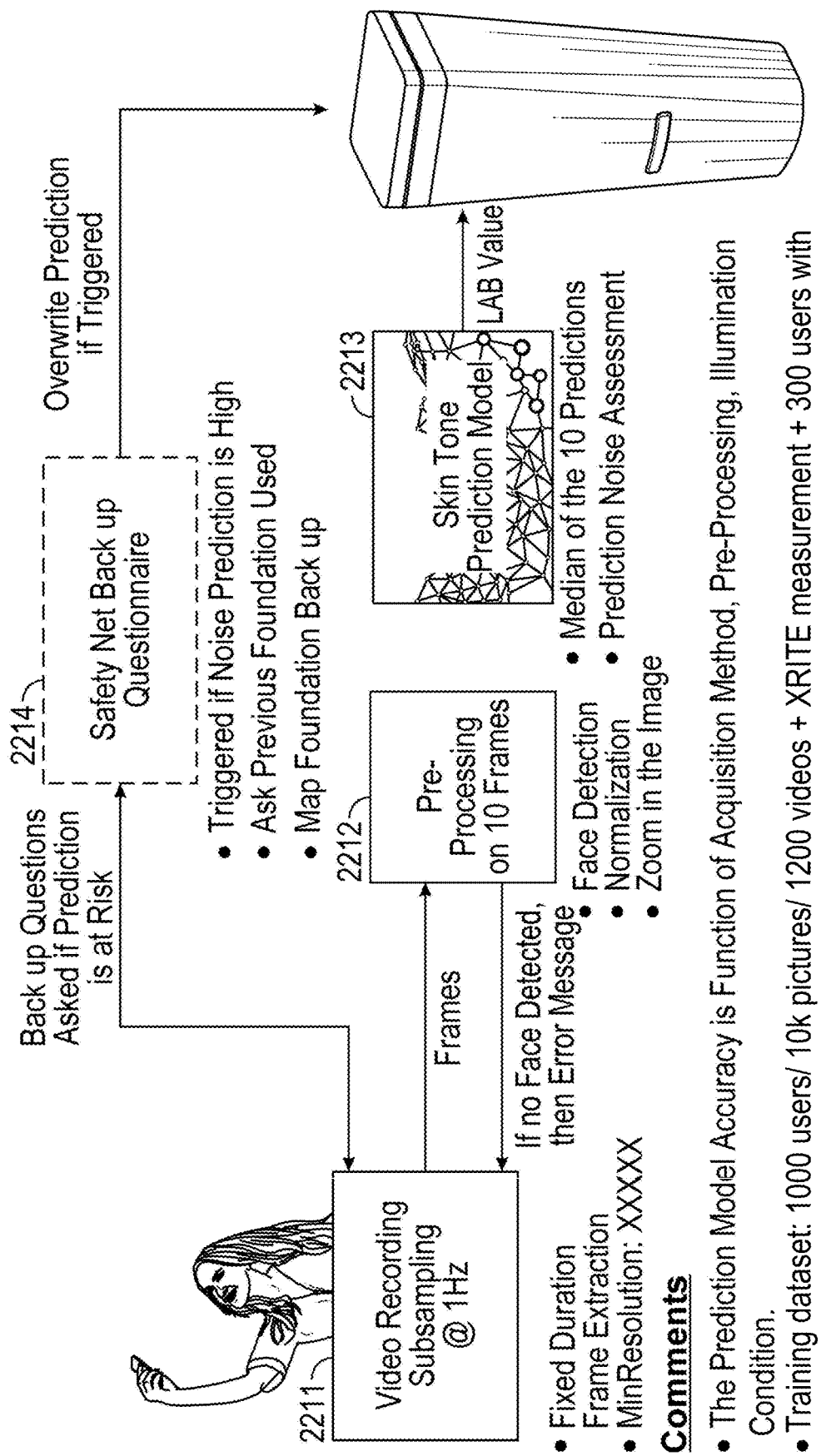
FIG. 22B provides details on a method of performing a skintone diagnosis.

FIG. 22B provides more details on the method of performing the above-described skintone diagnosis. At step 2211, the user performs video recording of themselves until face detection is achieved by the smartphone app. At step 2212, face detection is performed according to known methods. If no face is detected, an error message is displayed to the user, and it may request changing an angle or position of the camera relative to the user until face detection is achieved. Once face detection is performed, pre-processing is performed on 10 frames of video data, where a normalization process and zoom process is performed to assess the specific features on the user's face. Normalization is a process to align all frames according the same resolution, orientation width, lighting etc. Normalization is meant to make the frames comparable between each other and make sure that the main algorithm will be functioning in the validated condition/range of operation and avoid any outlier data points. A skin tone prediction model is then run in at step 2213 based on a median skin tone value detected in the 10 frames used for prediction. Additionally, a prediction noise assessment is performed using a median approach to filter/average noise. If the noise prediction is low, a LAB value of the skintone is used to determine the blend used to generate the foundation at the dispensing device. However, if the noise level is high, then a safety net backup questionnaire is triggered at step 2214, which asks a previous foundation that the user has used. Then the color of the previous foundation is mapped to a stored LAB value that is used to determine the blend used to generate the foundation at the dispensing device.

Figure 22C:
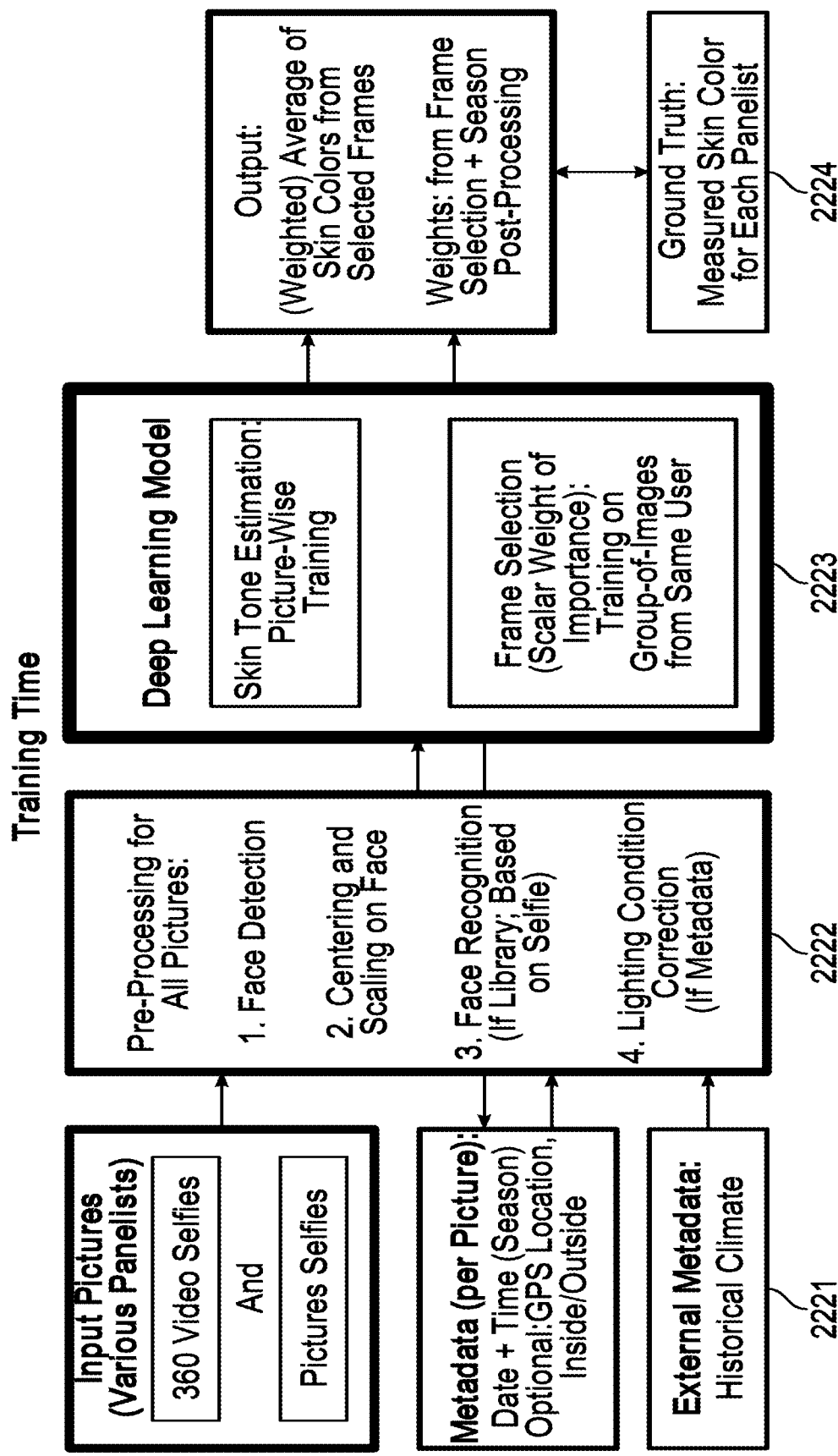
FIGS. 22C and 22D show details regarding how deep learning is utilized to estimate a skintone in an image.
Figure 22D:
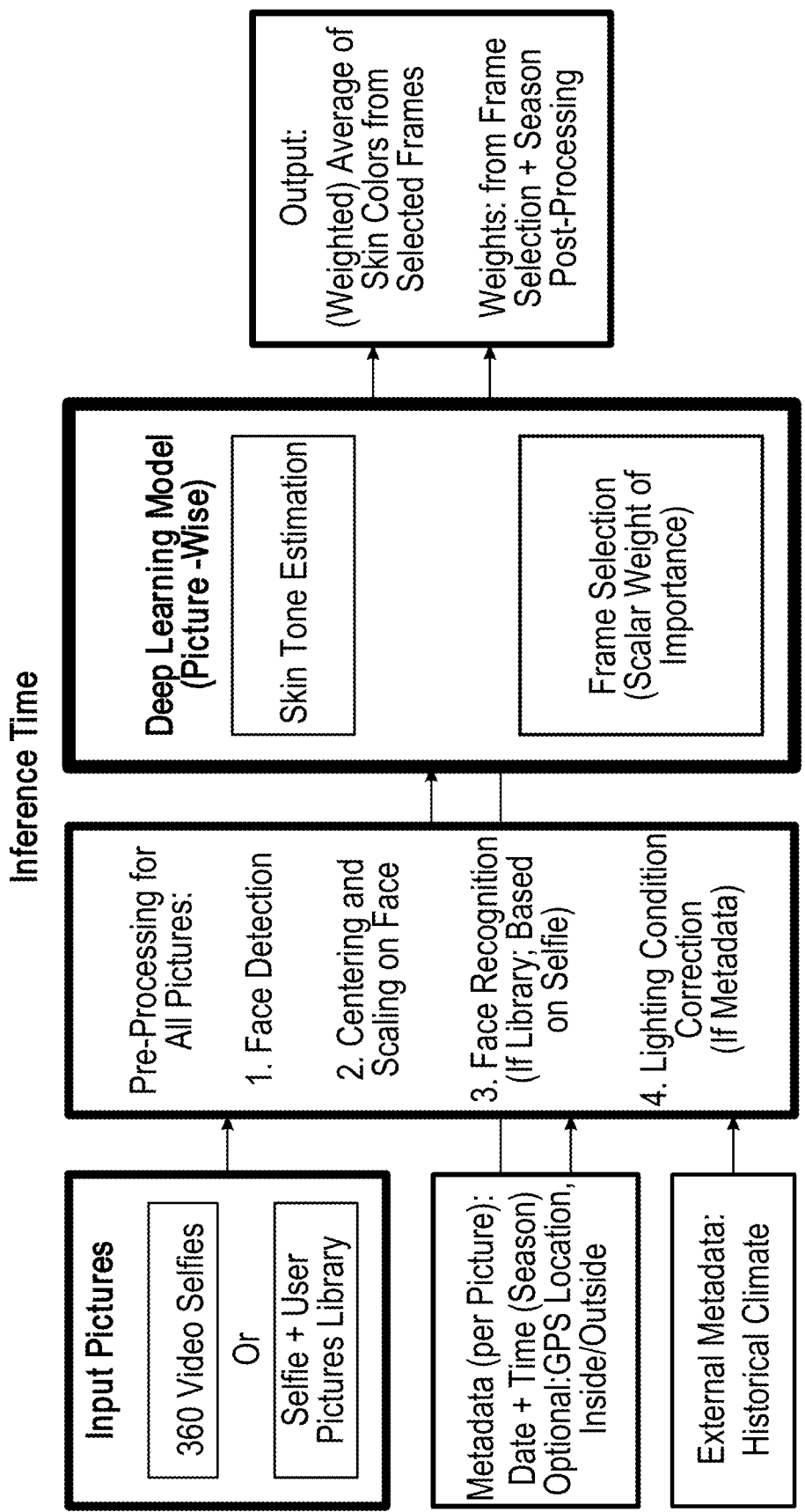

FIGS. 22C-D shows additional details regarding how deep learning is performed to cause the smartphone app (or the cloud platform) to estimate a skintone in an image. The same process may also be used to cause a device to estimate a skincare condition in an image. In FIG. 22C, training is performed for the deep learning model. The inputs are provided at stage 2221, where pictures (which could be 360 video selfies or picture selfies) are input along with metadata associated with the inputted picture and external metadata. The metadata associated with the picture may include a date and time (and/or season) along with an optional GPS location and an indication if the picture is taken inside or outside. The external metadata may be historical climate data. Pre-processing is performed on the input images at stage 2222, which may include face detection, centering and scaling, face recognition (depending on library availability), and lighting condition correction. At stage 2223, the deep learning model performs picture-wise training by learning the features for skin tone estimation. The deep learning model may also perform frame selection to determine the scalar weight of importance of selected frames based on a group of images from the same user. The output of the deep learning model (2224) provides a weighted average of skin colors from the selected frames and weights from frame selection and post-processing. To adjust the accuracy of the model, a measured skin color is input to the system for the actual user in the images to train the deep learning model.

FIG. 22D shows the usage of the deep learning model after training has reached an adequate level. This is referred to as "inference time" since the skin tone (or skin condition) will be inferred from images without being able to perform a truth measurement on the actual skin of the user. It can be seen that the stages in FIG. 22D is the same except that there is no measurement of the user's skin color in the final stage.

[Smart Swappable Cartridge System]

The dispensing device described above allows for swapping the consumable cartridges in a smart and efficient manner. The cartridges (consumables) used in the above-described dispensing device are preferably managed in sets (such as sets of three cartridges). For instance there could be separate sets of cartridges for each of the lipstick, skincare, and foundation applications described above. In the system, consumables sets equipped with smart chip or an electronic device configured to perform data storage and transmission/reception (such as NFC, RFID, or a contact chip). In the following description an NFC (Near Field Communication) tag will be mentioned, but the claims are not limiting to this example. Each cartridge has a different cosmetic attributes and a unique formula identifier that can identify attributes such as Shade/finish, Texture, and Skin/hair benefits. Attributes are stored on the integrated circuit at production and signed with an asymmetrical cryptographic algorithm.

As will be discussed in detail below, the NFC tag applied to the cartridges ensures the management of color universe for the user, multi device use cases, and traceability. The tag will have two zones of memory: one zone for the production data (encoded during the filling process); and one zone for the use where the device will encode the usage and follow up quantities. Additionally, the following security mechanism have been implemented: (i) ensure the non-modification of production data: sector edition are protected by password (secret password); (ii) ensure the non-duplication of the cartridge data in case of diversion: adding a signature mechanism using UIID (unique id of the tag, the data encoded, and the secret key of the manufacture). The app using the device to read cartridge will then check that the signature comes from the manufacturing entity before allowing dispensing.

Figure 23:
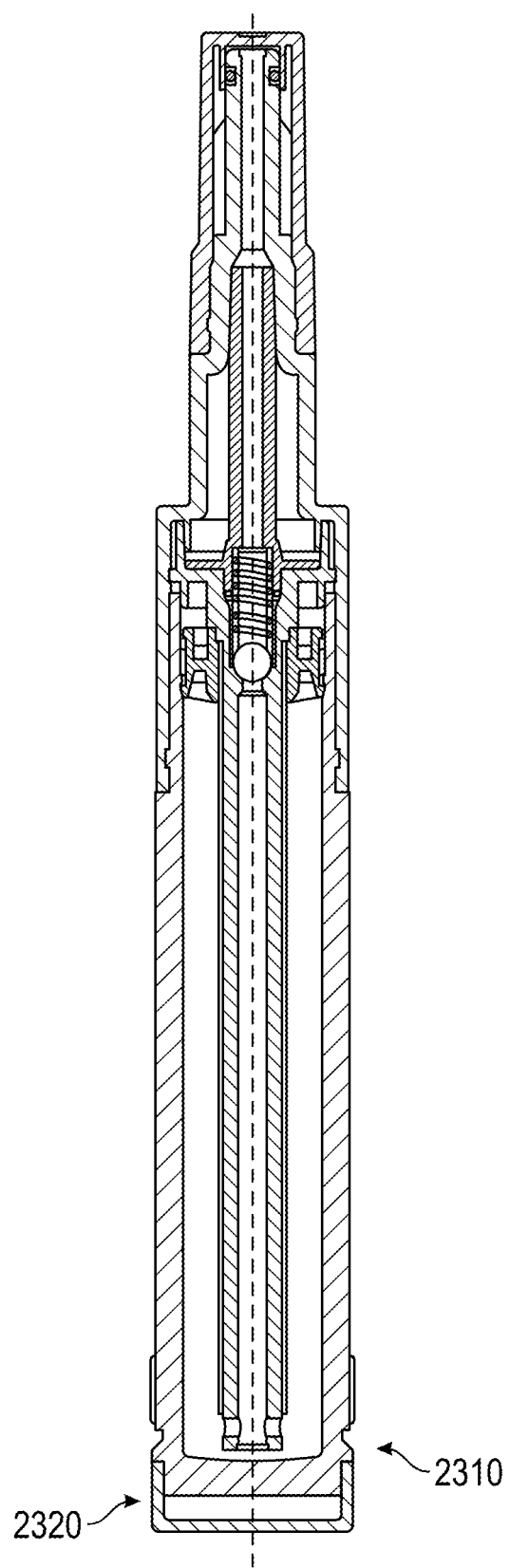
FIG. 23 shows a structure of a cartridge that has an NFC tag.

FIG. 23 shows a structure of the cartridge 2300, which is similar to the cartridge described above, but further includes a region 2310, which is an area where metallization is not allowed, and a NFC tag (smart chip) 2320 which is adhered to the bottom of the cartridge in a manner such that it is flat and without edges.

FIG. 24 shows a data format of the data stored on the NFC tag on the cartridge. The "OFF" column is for an "offset", which are the coordinates of the data coded in hexadecimal. The "Page" represents consecutive data array blocks because the system can only read/write entirely one page at a time. It can be seen that the format includes a tag identifier (Tag ID) and several fields. The data size for the data included on the NFC tag is 56 bytes in the present non-limiting example, but it can also be more or less. The data format shows that there is information fields directed to production information and other fields directed to usage tracking.

FIG. 25 shows a table that includes self-evident descriptions of the various fields contained in the data format of the NFC tag. Additionally, "base type" means the type of data: for example: u8 means unsigned integer one 8 bits. "Ule16" means unsigned integer of 16 bits. "Length" and "page" are the coordinates and allocation required in the memory page of the NFC tag. For example "u8" is unsigned integer that is coded on 8 bits that will require 8 bits memory space in the page 0 location.

FIG. 26 shows a structure of the dispensing device 2600 that is equipped for the smart swappable cartridge system. It can be seen that the dispensing device 2600 includes a contact/hall effect sensor 2610 that detects and counts a lid opening/closing cycle to trigger consumable reading and change detection operations. The device further includes a communication interface 2620, which in this case is a specific NFC antenna, for each cartridge canal that can read and write information onto the NFC tag of the cartridge at each dispensing.

Figure 27:
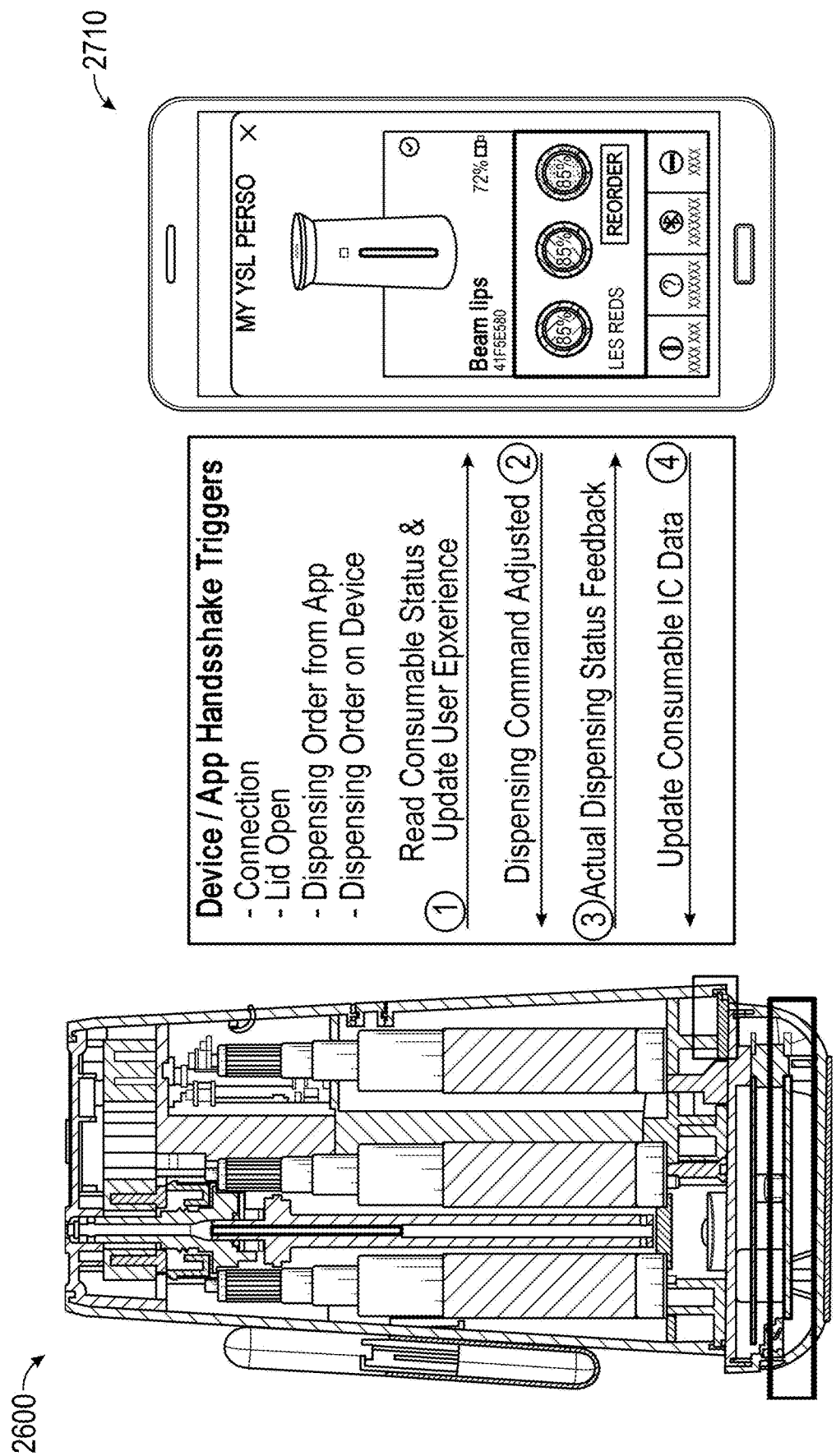
FIG. 27 shows a handshake between the dispensing device and a user smartphone device.

FIG. 27 shows a handshake between the dispensing device 2600 and the user smartphone device 2710. The various triggers for initiating communication between the dispensing device and the smartphone may include a connection being established between the devices (such as a Bluetooth pairing), the lid of the dispensing device being opened, a dispensing order from the smartphone app (such as one of the apps described above), or a dispensing order directly input on the dispensing device. In response to the trigger, the handshake includes in step 1, reading a consumable status of the cartridges stored on the dispensing device and sending the status to the smartphone. At the same time, the user experience is updated and sent to the smartphone. The "user experience" refers to a context of the device with respect to the user viewing a specific interface displaying to the user a pop up when the lid is open, cartridge being empty, or the color wheel has the correct color available. In step 2, the smartphone may transmit or adjust a dispensing command to the dispensing device. In step 3, the dispensing device may transmit the actual dispensing feedback to the smartphone. In step 4, the smartphone may transmit an instruction to update the NFC tags on the cartridges when a dispensing session is complete.

Figure 28:
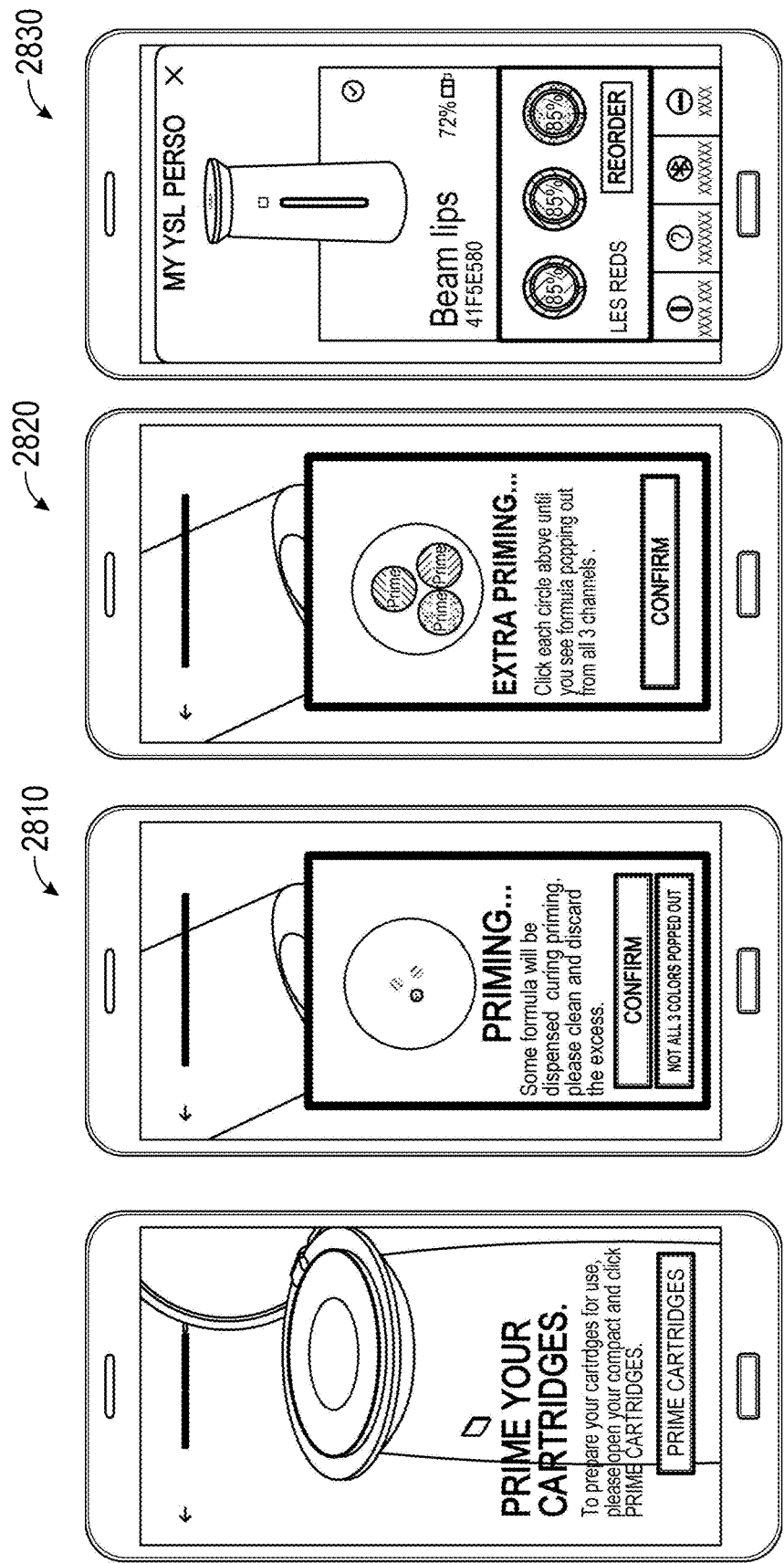
FIG. 28 shows consumer app state machine which shows a process from the app perspective of priming the cartridges before any use of the dispensing device.

FIG. 28 shows consumer app state machine which shows a process from the app perspective of priming the cartridges before any use of the dispensing device. In an initial priming step 2810, some formula may be dispensed in a predetermined sequence and/or simultaneously from each of the cartridges to verify that dispensing can be performed from each cartridge. In an extra priming step 2820, the user can practice clicking on a displayed color to control individual dispensing on command. This may be performed to assure that the correct color is detected in the correct canal within the device such that recipes can be assigned automatically to the correct canal. Step 2830 shows a display, when priming is complete, of the status of the cartridges in the dispensing device.

Accordingly, the priming process can detect when a new cartridge has been installed and it allows proper engagement with the plunger of the dispensing device and the formula contained in the cartridge so that a proper dose can be dispensed when an actual blend is being created.

Additionally, by detecting the exact cartridges that are installed, the set of cartridges (such as the set of three cartridges) can be determined, and the color attributes (or skincare attributes) that are possible with the current set are automatically updated on the app.

Also, the app can perform consumable management by suggesting or automatically performing cleaning of the pipes when a cartridge is changed. The app can further adapt the formula universe in the user interface function depending on what type of set of cartridges are installed.

Furthermore, the app state machine can detect inconsistent sets or missing cartridges. It can propose to buy missing set to reach a result. It can automatically detect expiration dates of any cartridges. Also, since safety information is stored on the cartridge, it allows natively multi-user and multi-device capability since each separate user smartphone will detect the information on the cartridge independently.

During priming, the cartridges can also be authenticated. A 32 bit hash code is generated at production using a secret key of the manufacturer and the code is encoded onto the NFC tag of the cartridge. The smartphone includes a hard-coded secret key, which may be included in a software developer kit (SDK), to verify the hash code upon reading data from the NFC tag transmitted from the dispensing device. The smartphone may also be hardcoded with the secret key if possible. A Unique Item Identification (UIID) tag may also be physically added to the cartridge or NFC tag (in the form of a barcode for example) and read by the dispending device. If the process of authentication of the cartridge fails, the dispensing device may transmit the notification to the smartphone.

In some rare cases, the user may encounter a cartridge where the NFC tag is not read by the machine (encoding error, tag destruction, device not in range, other defect). In this case the user has to be still able to dispense formula and use his device as normal as possible. To ensure this tolerant default mode, a recovery cartridge mode requiring the user to enter information of the cartridge will take over the operation. The application relying on THE SDK will then create a virtual cartridge to continue the algorithm to dispense. This automatic triggered recovery mode will be turned off at the moment a new cartridge is inserted or the NFC is again in range.

Figure 29:
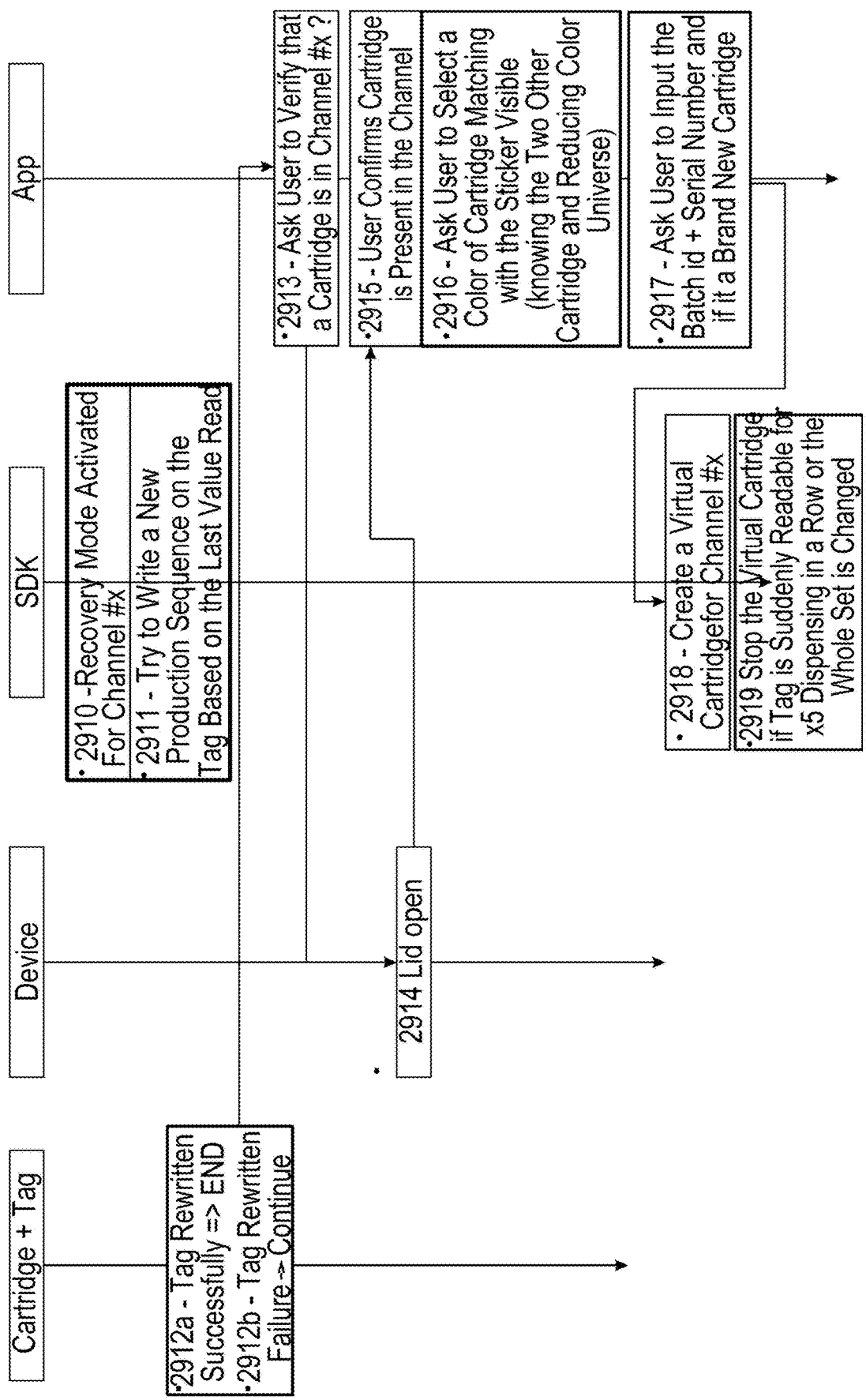
FIG. 29 shows a method of managing a faulty cartridge NFC tag in the afore-mentioned scenario.

FIG. 29 shows a method of managing a faulty cartridge NFC tag in the afore-mentioned scenario. If there is an error in reading data from the NFC tag, the process is started at step 2910 where the SDK installed on the smartphone actives a recovery mode for a particular canal in the dispensing device. At step 2911, the SDK attempts to write a new production sequence (by a transmission to the tag via the dispensing device) on the tag based on the last value read. At step 2912*a*, if the tag is written successfully, the process ends. However, at step 2912*b*, if the tag fails to be rewritten, the process proceeds to step 2940. At step 2913, the app displays a message asking the user to verify that a cartridge is in a proper channel (canal) and the dispensing device automatically opens the lid at step 2914. In other words, if the problem was that no cartridge was inserted, then this step will remedy this possibility. At step 2915, the user confirms that a cartridge is in the channel. If reading is still impossible, at step 2916, the user is asked to select a color of the cartridge matching with a sticker on the cartridge. At step 2917, the user is asked to input the batch ID and the serial number of the cartridge, and asked to verify if the cartridge is brand new. At step 2918, the SDK creates a virtual cartridge for the channel number. Dispensing operations can proceed based on the virtual cartridge being used a proxy for properly read NFC tag on the actual cartridge. At step 2919, the virtual cartridge will be stopped if the cartridge becomes suddenly readable for a predetermined number of dispensing operations in a row, or if the whole set of cartridges is changed.

[Dispensing and Auto-Cleansing System]

As the above-described system includes swapping cartridges of many different types, a special cleaning mechanism that integrates with the structure of the removable compact has been developed to provide a unique cleaning capability to enhance the user experience.

Figure 30:
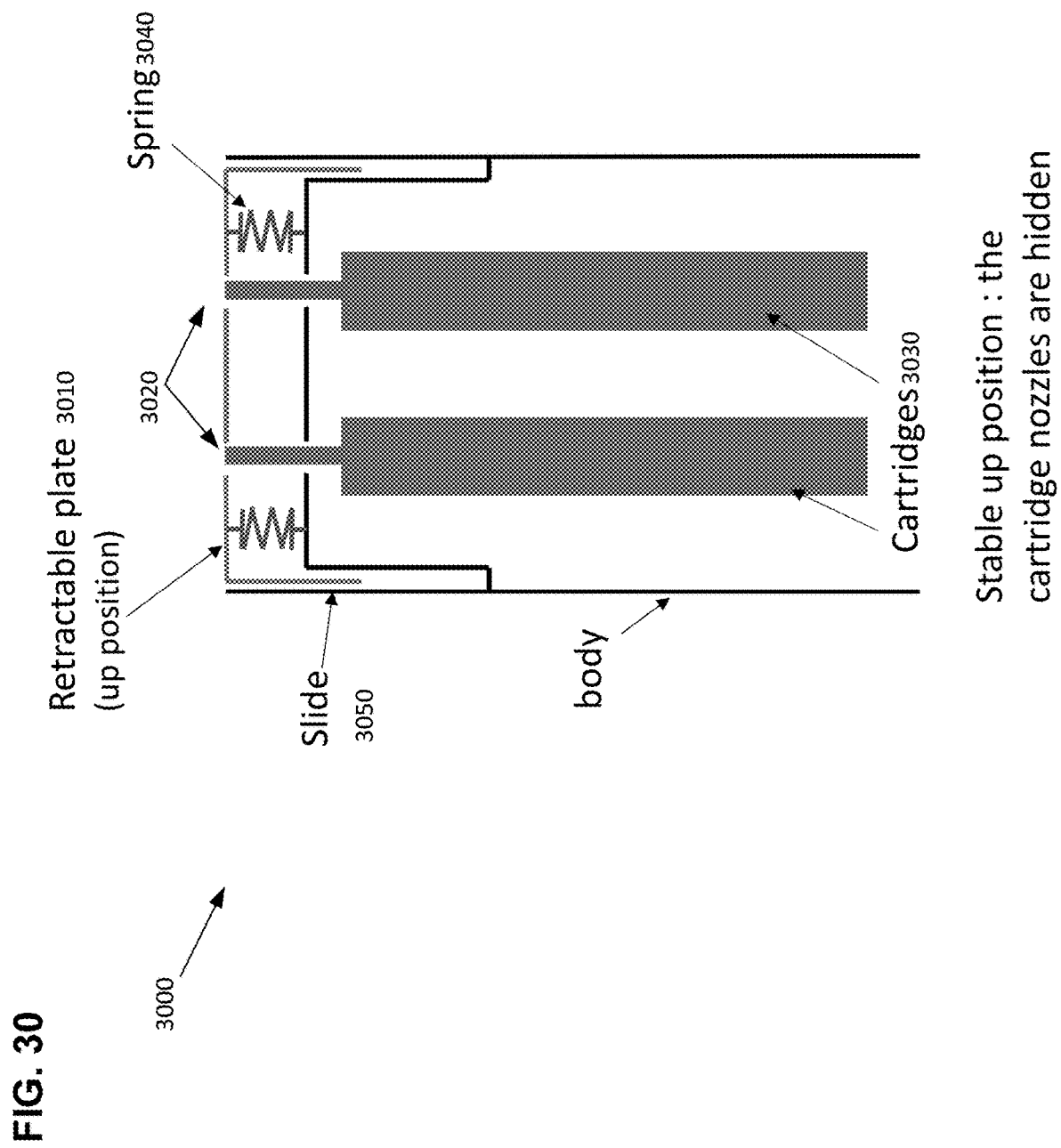
FIG. 30 shows a side-view of a dispensing device that includes a retractable plate.

FIG. 30 shows a simplified side-view of an embodiment of the dispensing device 3000 shows that the dispensing device includes a retractable plate 3010 with holes 3020 for accommodating the dispensing ends of the cartridges 3030. The device includes a spring 3040 that when the spring is uncompressed, the retractable plate in the "stable up position" and the cartridge nozzles are hidden. The stable up position hides the nozzle tip and also reduces dust or contamination getting into the nozzle.

It can be seen that the retractable plate includes a side surface that is bent at approximately 90 degrees to the top surface, which allows the plate to move downward into a slide groove 3050 of the body of the dispensing device.

Figure 31B:
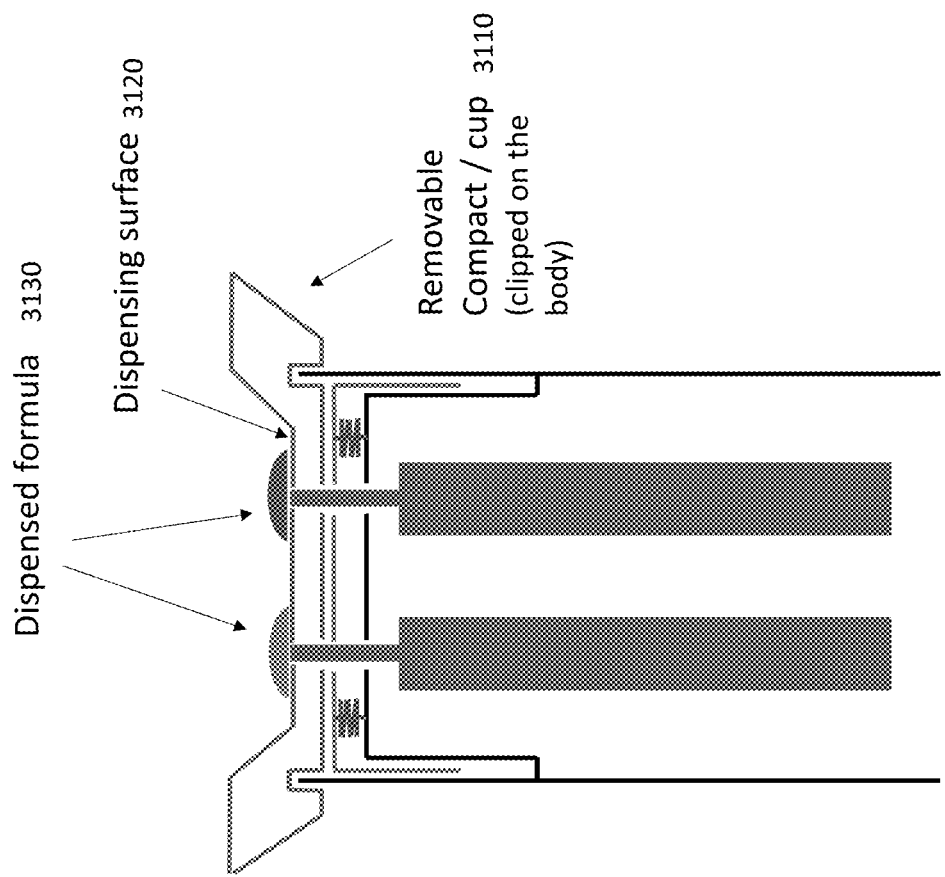
FIGS. 31A and 31B show different states of the retractable plate when it is at different heights.
Figure 31A:
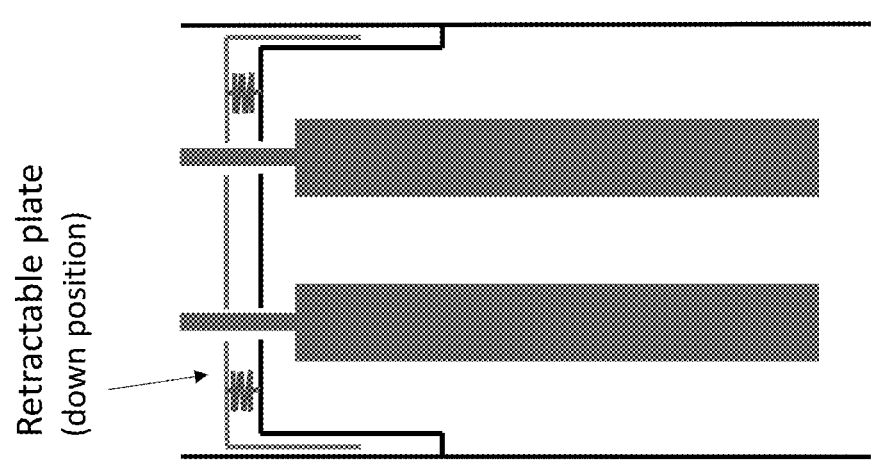

FIG. 31A shows that when force is pushed down on the retractable plate, the spring is compressed and the retractable plate is in the "down position."

FIG. 31B then shows that when the removable compact/cup 3110 is placed atop the retractable plate, the "down position" allows the cartridge nozzles to be flush with the dispensing surface 3120 of the compact/cup such that the dispensed formula 3130 dispenses in a smooth manner onto the dispensing surface.

With the above retractable plate mechanism in place, the method of cleaning the surface of the compact will be described with reference to FIG. 32.

Figure 32:
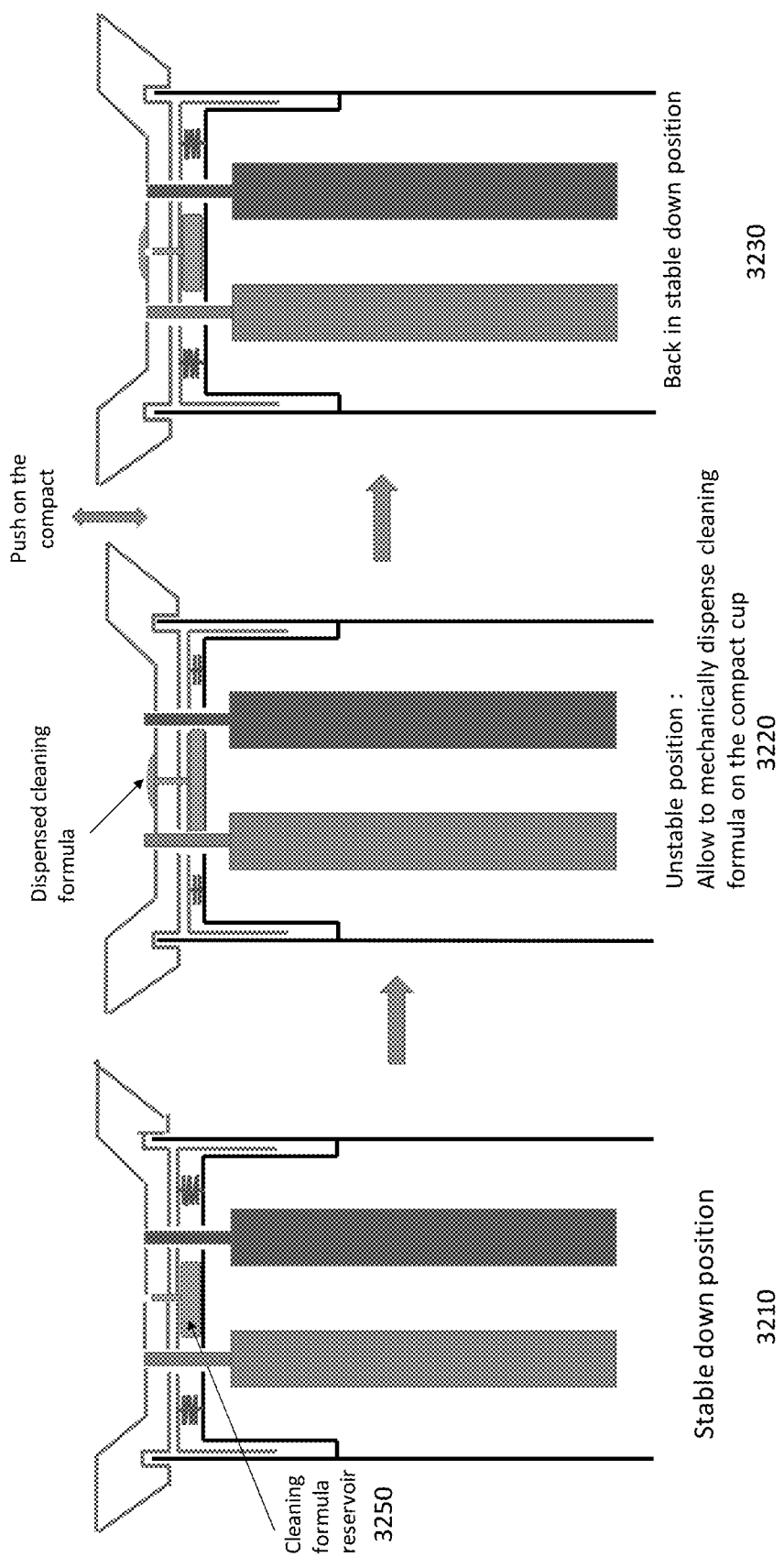
FIG. 32 shows a cleaning formula reservoir disposed between the body of the dispensing device and the retractable plate.

FIG. 32 shows that a cleaning formula reservoir 3250 is disposed between the body of the dispensing device and the retractable plate. In the "stable down position" at state 3210, the dispensing end of the cleaning reservoir is below an opening in the retractable plate. When additional force is applied to the retractable plate at state 3220, the dispensing end of the cleaning reservoir becomes flush with the surface of the compact and compression on the reservoir causes the cleaning formula to be dispensed onto the surface of the compact as shown in state 3230.

Examples of the cleaning formula include soap, alcohol, or other known cleaning solutions.

Each position described above may be achieved by manual force provided by the user. Alternatively, each position may be achieved by electromechanical means such as a motorized actuator device as is understood in the art. The cleaning formula may be manually wiped, spread, and/or brushed and removed by the user.

Figure 33:
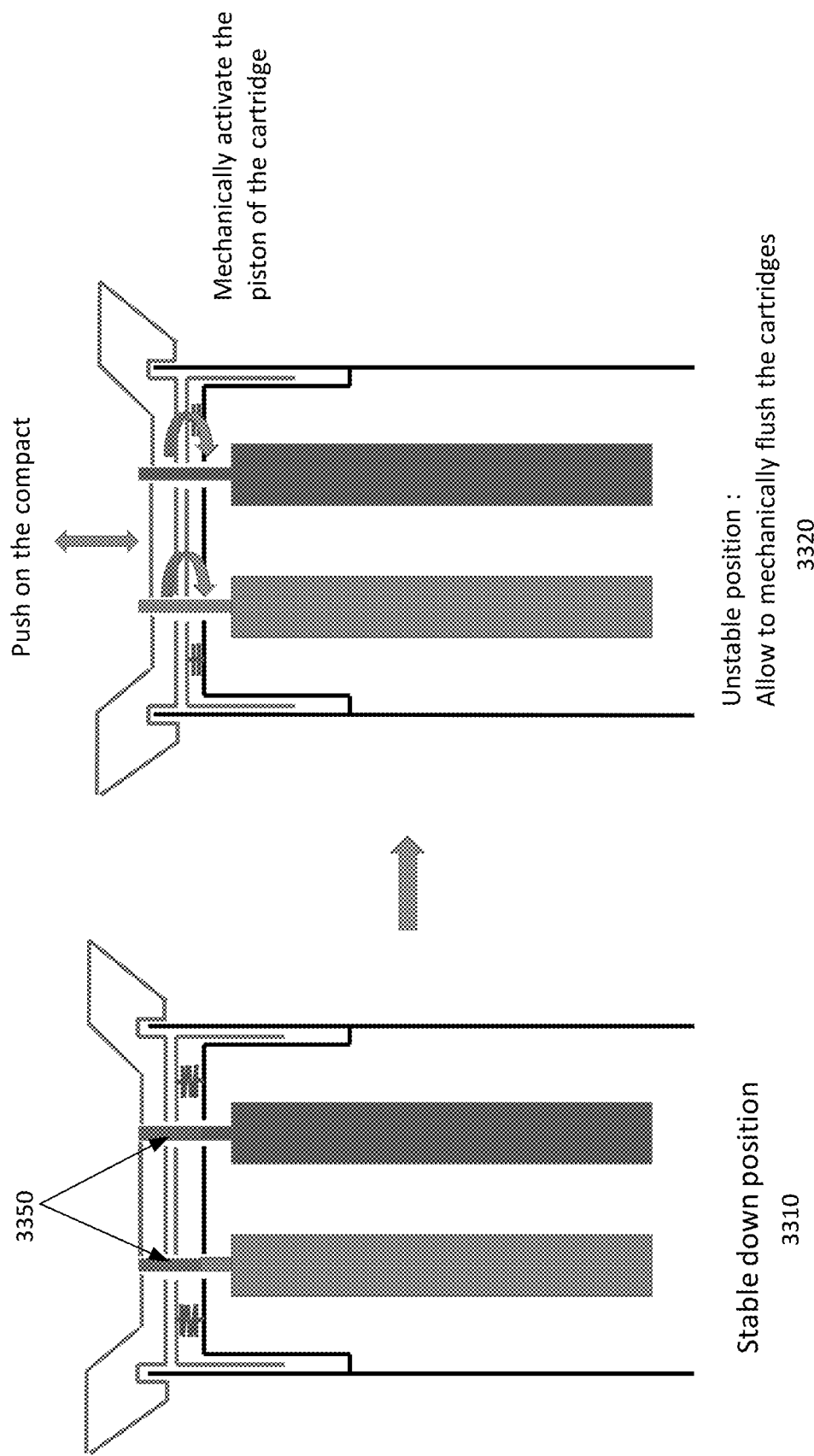
FIG. 33 shows an alternative use of the retractable plate describe above to provide a method of flushing the cartridges of any remaining ingredients or residues.

FIG. 33 shows an alternative use of the retractable plate describe above to provide a method of flushing the cartridges of any remaining ingredients or residues (shown as 3350 in state 3310). In state 3310, the dispensing device is shown in the stable down position. In state 3320, when the compact is pushed down, the downward motion can be translated to activation of the piston of the cartridge. This may allow the user to use/flush the last remaining ingredients in the cartridges if desired.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernable variants of the teachings herein, define, in part, the scope of the foregoing claim terminology such that no inventive subject matter is dedicated to the public.

What is claimed is:

1. An apparatus for dispensing cosmetic material, comprising:

a dispensing device configured to receive at least one cartridge that contains a cosmetic material and to dispense a specified amount of the cosmetic material from the cartridge onto a dispensing surface;

wherein the dispensing surface is configured to be part of a detachable portion of the apparatus, and the dispensing device further includes a retractable plate disposed beneath the detachable portion, wherein a dispensing end of the at least one cartridge is configured to penetrate the retractable plate and the detachable portion, such that (i) when the retractable plate is at a stable highest position, the dispensing end of the at least one cartridge is flush with the surface of the retractable plate, (ii) when the retractable plate is moved to a predetermined stable downward position below the highest position, and the detachable portion is placed on the retractable surface, the dispensing end of the at least one cartridge is flush with the dispensing surface and the retractable plate is configured to move even further downward to an unstable position in response to a downward force on the detachable portion.

2. The apparatus according to claim 1, further comprising a cleaning formula reservoir disposed between a body of the dispensing device and the retractable plate, and the cleaning formula reservoir has a dispensing end that is configured to penetrate the retractable plate and the detachable portion and is configured to dispense a cleaning formula onto the dispensing surface when the retractable plate is configured to move even further downward to the unstable position.

3. The apparatus according to claim 1, further comprising a spring mechanism that is coupled to a bottom surface of the retractable plate at one end and a body of the dispensing device at another end.

4. The apparatus according to claim 1, wherein the at least one cartridge is configured to dispense a remaining amount of the cosmetic material from the cartridge onto the dispensing surface when the retractable plate is configured to move even further downward to the unstable position.

* * * * *